United States Patent
Yang et al.

(10) Patent No.: US 10,568,516 B2
(45) Date of Patent: Feb. 25, 2020

(54) METHODS AND DEVICES FOR IMAGING AND/OR OPTOGENETIC CONTROL OF LIGHT-RESPONSIVE NEURONS

(71) Applicant: The Board of Trustees of the Leland Stanford Junior University, Stanford, CA (US)

(72) Inventors: Samuel Yang, Stanford, CA (US); Karl A. Deisseroth, Stanford, CA (US); William E. Allen, Stanford, CA (US); Isaac V. Kauvar, Stanford, CA (US); Aaron S. Andalman, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 108 days.

(21) Appl. No.: 15/735,550

(22) PCT Filed: Jun. 13, 2016

(86) PCT No.: PCT/US2016/037271
§ 371 (c)(1),
(2) Date: Dec. 11, 2017

(87) PCT Pub. No.: WO2016/209654
PCT Pub. Date: Dec. 29, 2016

(65) Prior Publication Data
US 2018/0177401 A1    Jun. 28, 2018

Related U.S. Application Data

(60) Provisional application No. 62/183,012, filed on Jun. 22, 2015.

(51) Int. Cl.
*A61B 5/00* (2006.01)
*G01N 21/47* (2006.01)
(Continued)

(52) U.S. Cl.
CPC .......... *A61B 5/0071* (2013.01); *A61B 5/0048* (2013.01); *A61B 5/4064* (2013.01);
(Continued)

(58) Field of Classification Search
CPC ... A61B 5/0071; A61B 5/0048; A61B 5/4064; G01N 21/4788; G01N 21/6428;
(Continued)

(56) References Cited

U.S. PATENT DOCUMENTS

| 2,968,302 | A | 1/1961 | Fry et al. |
| 3,131,690 | A | 5/1964 | Innis et al. |

(Continued)

FOREIGN PATENT DOCUMENTS

| CN | 1079464 A | 12/1993 |
| CN | 1558222 A | 12/2004 |

(Continued)

OTHER PUBLICATIONS

Broxton et al. ("Wave Optics Theory and 3-D Deconvolution for the Light Field Microscope", Optics Express, vol. 21 Issue 21, pp. 25418-25439, (2013) (Year: 2013).*

(Continued)

*Primary Examiner* — Leon Viet Q Nguyen
(74) *Attorney, Agent, or Firm* — Rudy J. Ng; Paula A. Borden; Bozicevic, Field & Francis LLP

(57) ABSTRACT

A method for measuring the activity of one or more excitable cells, such as neurons, in a target tissue is provided. The present method may include measuring the activity of individual, selected excitable cells by projecting one or more three dimensional (3D) multi-focal laser light patterns into a target tissue containing excitable cells adapted to emit cellular electrical activity—sensitive fluorescence, to generate a multiplexed 2D diffraction pattern of fluorescence emitted by the neurons, and resolving the multiplexed 2D
(Continued)

diffraction pattern. Also provided herein is a system configured to perform the present method, the system including a microscope configured to project one or more 3D multifocal laser light patterns into a target tissue using a spatial light modulator and a mirror galvanometer, and a microlens array and an image detector to record individual and multiplexed 2D diffraction patterns of light emitted from the target tissue.

33 Claims, 12 Drawing Sheets

(51) Int. Cl.
    *G01N 21/64*           (2006.01)
    *G02B 21/06*           (2006.01)
    *G02B 21/16*           (2006.01)
    *G06T 7/00*            (2017.01)

(52) U.S. Cl.
    CPC ..... *G01N 21/4788* (2013.01); *G01N 21/6428* (2013.01); *G01N 21/6458* (2013.01); *G02B 21/06* (2013.01); *G02B 21/16* (2013.01); *G06T 7/0012* (2013.01); *G01N 2021/6478* (2013.01); *G01N 2201/0675* (2013.01); *G01N 2201/06113* (2013.01); *G06T 2207/10056* (2013.01); *G06T 2207/10064* (2013.01); *G06T 2207/10152* (2013.01); *G06T 2207/30016* (2013.01)

(58) Field of Classification Search
    CPC ..... G01N 21/6458; G01N 2201/06113; G01N 2201/0675; G01N 2021/6478; G02B 21/06; G02B 21/16; G06T 7/0012; G06T 2207/10056; G06T 2207/10064; G06T 2207/10152; G06T 2207/30016
    See application file for complete search history.

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,734,578 A | 3/1988 | Horikawa |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,348,990 B1 | 2/2002 | Igasaki et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,662,039 B2 | 12/2003 | Yuste et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,932,873 B2 | 4/2011 | Smith et al. |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |

(56) References Cited

U.S. PATENT DOCUMENTS

| | | |
|---|---|---|
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Schneider et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,284,353 B2 | 3/2016 | Deisseroth et al. |
| 9,308,392 B2 | 4/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,360,472 B2 | 6/2016 | Deisseroth et al. |
| 9,365,628 B2 | 6/2016 | Deisseroth et al. |
| 9,394,347 B2 | 7/2016 | Deisseroth et al. |
| 9,421,258 B2 | 8/2016 | Deisseroth et al. |
| 9,453,215 B2 | 9/2016 | Deisseroth et al. |
| 9,458,208 B2 | 10/2016 | Deisseroth et al. |
| 9,505,817 B2 | 11/2016 | Deisseroth et al. |
| 9,522,288 B2 | 12/2016 | Deisseroth et al. |
| 9,604,073 B2 | 3/2017 | Deisseroth et al. |
| 9,615,789 B2 | 4/2017 | Deisseroth et al. |
| 9,636,380 B2 | 5/2017 | Deisseroth et al. |
| 9,693,692 B2 | 7/2017 | Deisseroth et al. |
| 9,757,587 B2 | 9/2017 | Deisseroth et al. |
| 9,829,492 B2 | 11/2017 | Deisseroth et al. |
| 9,840,541 B2 | 12/2017 | Deisseroth et al. |
| 9,850,290 B2 | 12/2017 | Deisseroth et al. |
| 9,855,442 B2 | 1/2018 | Deisseroth et al. |
| 9,878,176 B2 | 1/2018 | Deisseroth et al. |
| 9,968,652 B2 | 5/2018 | Deisseroth et al. |
| 9,969,783 B2 | 5/2018 | Deisseroth et al. |
| 9,992,981 B2 | 6/2018 | Deisseroth et al. |
| 10,018,695 B2 | 7/2018 | Deisseroth et al. |
| 10,035,027 B2 | 7/2018 | Deisseroth et al. |
| 10,036,758 B2 | 7/2018 | Deisseroth et al. |
| 10,046,174 B2 | 8/2018 | Deisseroth et al. |
| 10,052,383 B2 | 8/2018 | Deisseroth et al. |
| 10,052,497 B2 | 8/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1* | 12/2002 | Tsao ............... G02B 27/2271 345/32 |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060015 A1 | 3/2007 | Kucklick |
| 2007/0060984 A1 | 3/2007 | Webb et al. |
| 2007/0128662 A1* | 6/2007 | Isacoff ............ C07K 14/70571 435/7.1 |
| 2007/0135875 A1 | 6/2007 | Demarais et al. |
| 2007/0156180 A1 | 7/2007 | Jaax et al. |
| 2007/0171502 A1 | 7/2007 | Birk et al. |
| 2007/0191906 A1 | 8/2007 | Lyer et al. |
| 2007/0196815 A1* | 8/2007 | Lappe ............... G01N 21/6408 435/4 |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |

(56) References Cited

U.S. PATENT DOCUMENTS

| | | |
|---|---|---|
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Zhang et al. |
| 2010/0209352 A1 | 8/2010 | Hultman et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0224095 A1 | 9/2011 | Zoller et al. |
| 2011/0233046 A1 | 9/2011 | Nikolenko et al. |
| 2011/0249866 A1 | 10/2011 | Piestun et al. |
| 2011/0279893 A1 | 11/2011 | Vizi et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0190629 A1 | 7/2012 | Tomita et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0066402 A1 | 3/2013 | Lin et al. |
| 2013/0144359 A1 | 6/2013 | Kishawi et al. |
| 2013/0286181 A1* | 10/2013 | Betzig .................. H04N 7/18 |
| | | 348/79 |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0313315 A1* | 10/2014 | Shoham ............... G02B 21/002 |
| | | 348/80 |
| 2014/0324133 A1 | 10/2014 | Deisseroth et al. |
| 2015/0040249 A1 | 2/2015 | Deisseroth et al. |
| 2015/0112411 A1 | 4/2015 | Beckman et al. |
| 2015/0165227 A1 | 6/2015 | Deisseroth et al. |
| 2015/0217128 A1 | 8/2015 | Deisseroth et al. |
| 2015/0301028 A1* | 10/2015 | Eggan ................ G01N 33/5058 |
| | | 435/29 |
| 2016/0015996 A1 | 1/2016 | Deisseroth et al. |
| 2016/0038761 A1 | 2/2016 | Deisseroth et al. |
| 2016/0038764 A1 | 2/2016 | Deisseroth et al. |
| 2016/0045599 A1 | 2/2016 | Deisseroth et al. |
| 2016/0194624 A1 | 7/2016 | Deisseroth et al. |
| 2016/0199663 A1 | 7/2016 | Deisseroth et al. |
| 2016/0252524 A1 | 9/2016 | Deisseroth et al. |
| 2016/0258929 A1 | 9/2016 | Deisseroth et al. |
| 2016/0279267 A1 | 9/2016 | Deisseroth et al. |
| 2016/0316730 A1 | 11/2016 | Deisseroth et al. |
| 2016/0316732 A1 | 11/2016 | Deisseroth et al. |
| 2016/0317658 A1 | 11/2016 | Deisseroth et al. |
| 2016/0331995 A1 | 11/2016 | Deisseroth et al. |
| 2017/0056467 A1 | 3/2017 | Deisseroth et al. |
| 2017/0072219 A1 | 3/2017 | Deisseroth et al. |
| 2017/0157269 A1 | 6/2017 | Deisseroth et al. |
| 2017/0160360 A1 | 6/2017 | Deisseroth et al. |
| 2017/0198017 A1 | 7/2017 | Deisseroth et al. |
| 2017/0202912 A1 | 7/2017 | Lammel et al. |
| 2017/0211040 A1 | 7/2017 | Deisseroth et al. |
| 2017/0348545 A1 | 12/2017 | Deisseroth et al. |
| 2018/0020921 A1 | 1/2018 | Deisseroth et al. |

FOREIGN PATENT DOCUMENTS

| | | |
|---|---|---|
| CN | 101288768 A | 10/2008 |
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |

(56) References Cited

FOREIGN PATENT DOCUMENTS

| | | |  |
|---|---|---|---|
| WO | WO 2011/005978 | 1/2011 | |
| WO | WO 2011/066320 | 6/2011 | |
| WO | WO 2011/106783 | 9/2011 | |
| WO | WO 2011/116238 | 9/2011 | |
| WO | WO 2011116238 | 9/2011 | |
| WO | WO 2011/127088 | 10/2011 | |
| WO | WO 2012/032103 | 3/2012 | |
| WO | WO 2012/061676 | 5/2012 | |
| WO | WO 2012/061681 | 5/2012 | |
| WO | WO 2012/061684 | 5/2012 | |
| WO | WO 2012/061688 | 5/2012 | |
| WO | WO 2012/061690 | 5/2012 | |
| WO | WO 2012/061741 | 5/2012 | |
| WO | WO 2012/061744 | 5/2012 | |
| WO | WO 2012/106407 | 8/2012 | |
| WO | WO 2012/134704 | 10/2012 | |
| WO | WO 2013/003557 | 1/2013 | |
| WO | WO 2013/016486 | 1/2013 | |
| WO | WO 2013/090356 | 6/2013 | |
| WO | WO 2013/126521 | 8/2013 | |
| WO | WO 2013/126762 | 8/2013 | |
| WO | WO2013/126762 A1 * | 8/2013 | ............ G02B 21/00 |
| WO | WO 2013/142196 | 9/2013 | |
| WO | WO 2014020513 | 4/2014 | |
| WO | WO 2014/081449 | 5/2014 | |
| WO | WO 2014/117079 | 7/2014 | |
| WO | WO 2014117079 | 7/2014 | |
| WO | WO 2015/148974 | 10/2015 | |
| WO | WO 2015148974 | 12/2015 | |
| WO | WO 2016/019075 | 2/2016 | |
| WO | WO 2016/090172 | 6/2016 | |
| WO | WO 2017/087542 | 5/2017 | |
| WO | WO 2017087542 | 5/2017 | |

OTHER PUBLICATIONS

Nargeot et al.; Molecular basis of the diversity of calcium channels in cardiovascular tissues European Heart Journal, 1997, Supplemental A, A15-A26.

Ahmad, et al. "Heterplogous expression of bovine rhodopsin in *Drosophila* photoreceptor cells" Invest Ophthalmol Vis Sci. 2006, 3722-3728.

Clare "Targeting Ion Channels for Drug Discovery" Discov Med. 2010 vol. 9 No. 46 pp. 1-6.

Clare "Functional Expression of Ion Channels in Mammalian Systems" Protein Science Encyclopedia A.R. Fersht (Ed.) 2008 pp. 79-109.

Reeves et al., "Structure and function in rhodosin: A tetracycline-inducible system in stable mammalian cell lines for high-level expression of opsin mutants" PNAS, 2002 vol. 99 No. 21 pp. 13413-13418.

Erbguth et al. "Bimodal Activation of Different Neuron Classes with Spectrally Red-Shifted Channelrhodopsin Chimera C1V1 in Caenorhabditis elegans," *PLOS ONE*, 2012, vol. 7 No. 10, pp. e46827/1-9.

Li et al.; "Role of a Helix B Lysine Residue in the Photoactive Site in Channelrhodopsins," Biophysical Journal, 2014, vol. 106, pp. 1607-1617.

Prigge et al.: "Functional Studies of Volvox Channelrhodopsin Chimeras," Biophysical Journal, 2010, vol. 98, No. 3, Suppl. 1, 3694 Poster, 1 page.

Prigge et al.; Color-tuned Channelrhodopsins for Multiwavelength Optogenetics, J. Biol. Chem. 2012, vol. 287, No. 38, pp. 31804-31812.

Tsunoda & Hegemann "Glu 87 of Channelrhodopsin-1 Causes pH-dependent Color Tuning and Fast Photocurrent Inactivation," Photochemistry and Photobiology, 2009, vol. 85, No. 2, pp. 564-569.

Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.

Aebischer, et al. "Long-Term Cross-Species Brain Transplantation of a Polymer-Encapsulated Dopamine-Secreting Cell Line", Experimental Neurology, 1991, vol. 111, pp. 269-275.

Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

Ahmad, et al. "The *Drosophila rhodopsin* cytoplasmic tail domain is required for maintenance of rhabdomere structure." The FASEB Journal, 2007, vol. 21, p. 449-455.

Airan, et al., "Temporally Precise in vivo Control of Intracellular Signaling", 2009, Nature, vol. 458, No. 7241, pp. 1025-1029.

Airan, et al.; "Integration of light-controlled neuronal firing and fast circuit imaging"; Current Opinion in Neurobiology; vol. 17, pp. 587-592 (2007).

Akirav, et al. "The role of the medial prefrontal cortex-amygdala circuit in stress effects on the extinction of fear", Neural Plasticity, 2007: vol. 2007 Article ID:30873, pp. 1-11.

Ali; "Gene and stem cell therapy for retinal disorders"; vision-research.en—The Gateway to European Vision Research; accessed from http://www.vision-research.eu/index.php?id=696, 10 pages (accessed Jul. 24, 2015).

Alilain, et al.; "Light-Induced Rescue of Breathing after Spinal Cord Injury"; The Journal of Neuroscience; vol. 28, No. 46, pp. 11862-11870 (Nov. 12, 2008).

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Arenkiel, et al. "In vivo light-induced activation of neural circuitry in transgenic mice expressing Channelrhodopsin-2", Neuron, 2007, 54:205-218.

Argos, et al. "The integrase family of site-specific recombinases: regional similarities and global diversity", The EMBO Journal, 1986, vol. 5, No. 2, pp. 433-440.

Asano, et al.; "Optically Controlled Contraction of Photosensitive Skeletal Muscle Cells"; Biotechnology & Bioengineering; vol. 109, No. 1, pp. 199-204 (Jan. 2012).

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.

Azizgolshani, et al.; "Reconstituted plant viral capsids can release genes to mammalian cells"; Virology; vol. 441, No. 1, pp. 12-17 (2013).

Babin et al. "Zebrafish Models of Human Motor Neuron Diseases: Advantages and Limitations", Progress in Neurobiology (2014), 118:36-58.

Balint et al., "The Nitrate Transporting Photochemical Reaction Cycle of the Pharanois Halorhodopsin", Biophysical Journal, 2004, 86:1655-1663.

Bamberg et al. "Light-driven proton or chloride pumping by halorhodopsin." Proc. Natl. Academy Science USA, 1993, vol. 90, No. 2, p. 639-643.

Banghart, et al. "Light-activated ion channels for remote control of neuronal firing". Nature Neuroscience, 2004, vol. 7, No. 12 pp. 1381-1386.

Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).

Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).

Bebbington et al., "The use of vectors based on gene amplification for the expression of cloned genes in mammalian cells in DNA cloning" vol. 3, Academic Press, New York, 1987.

(56) References Cited

OTHER PUBLICATIONS

Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Bibel, et al.; "Differentiation of mouse embryonic stem cells into a defined neuronal lineage"; Nature Neuroscience; vol. 7, No. 9, pp. 1033-1009 (Sep. 2004).
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al.; "A history of optogenetics: the development of tools for controlling brain circuits with light"; F1000 Biology Reports; vol. 3, No. 11, 12 pages (May 3, 2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga Volvox carteri", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-7.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; Vol . 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cannon, et al.; "Endophenotypes in the Genetic Analyses of Mental Disorders"; Annu. Rev. Clin. Psychol.; vol. 2, pp. 267-290 (2006).
Cardin, et al. "Driving Fast spiking Cells Induces Gamma Rhythm and Controls Sensory Responses", 2009, Nature, vol. 459, vol. 7247, pp. 663-667.
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Chow et al., "Optogenetics and translation medicine", Sci Transl Med., 2013, 5(177):177.
Chow, et al.; "High-performance genetically targetable optical neural silencing by light-driven proton pumps"; Nature; vol. 463, pp. 98-102 (Jan. 7, 2010).
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Coleman, et al.; "Assessing Anxiety in Nonhuman Primates"; Ilar Journal; vol. 55, No. 2, pp. 333-346 (2014).
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol. , 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.

(56) References Cited

OTHER PUBLICATIONS

Daniel, et al.; "Stress Modulation of Opposing Circuits in the Bed Nucleus of the Stria Terminalis"; Neuropsychopharmacology Reviews; vol. 41, pp. 103-125 (2016).
Date, et al. "Grafting of Encapsulated Dopamine-Secreting Cells in Parkinson's Disease: Long-Term Primate Study", Cell Transplant, 2000, vol. 9, pp. 705-709.
Davidson, et al.; "Viral Vectors for Gene Delivery to the Nervous System"; Nature Reviews Neuroscience; vol. 4, pp. 353-364 (May 2003).
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. " Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Implant; Merriam-Webster Dictionary; retrieved Nov. 7, 2016 (http://www.merriam-webster.com/dictionary/implant).
Definition of integral. Merriam-Webster Dictionary, retrieved on Mar. 20 2017; Retrieved from the internet: <http://www.merriam-webster.com/dictionary/integral>.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Deonarain; "Ligand-targeted receptor-mediated vectors for gene delivery"; Exp. Opin. Ther. Patents; vol. 8, No. 1, pp. 53-69 (1998).
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.

EBI accession No. EMBL: J05199; "N. pharaonis halorhodopsin (hop) gene, complete cds"; (Nov. 22, 1990).
EBI accession No. Uniprot: A7UOY6; "SubName: Full=Bacteriorhodopsin"; (Aug. 10, 2010).
EBI accession No. Uniprot: B0R5N9; "Subname: Full=Bacteriorhodopsin"; (Apr. 8, 2008).
EBI accession No. Uniprot: B4Y103; "SubName: Full=Channelrhodopsin-1"; (Sep. 23, 2008).
EBI accession No. Uniprot: P15647; "RecName: Full=Halorhodopsin; Short=HR; Alt Name: Full=NpHR"; (Apr. 1, 1990).
Edelstein, et al.; "Gene therapy clinical trials worldwide 1989-2004—an overview"; The Journal of Gene Medicine; vol. 6, pp. 597-602 (2004).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Fanselow, et al.; "Why We Think Plasticity Underlying Pavlovian Fear Conditioning Occurs in the Basolateral Amygdala"; Neuron; vol. 23, pp. 229-232 (Jun. 1999).
Farber, et al. "Identification of Presynaptic Neurons by Laser Photostimulation", Science, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.
Ferenczi, et al.; "Optogenetic approaches addressing extracellular modulation of neural excitability"; Scientific Reports; vol. 6, 20 pages (Apr. 5, 2016).
Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Friedman, et al.; "VTA Dopamine Neuron Bursting is Altered in an Animal Model of Depression and Corrected by Desipramine"; J. Mol. Neurosci.; vol. 34, pp. 201-209 (2008).
Garrido et al., "A targeting motif involved in sodium channel clustering at the axonal initial segment", Science, 2003, vol. 300, No. 5628, pp. 2091-2094.

(56) References Cited

OTHER PUBLICATIONS

Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gerits, et al.; "Optogenetically Induced Behavioral and Functional Network Changes in Primates"; Current Biology; vol. 22, pp. 1722-1726 (Sep. 25, 2012).
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gong, et al.; "Enhanced Archaerhodopsin Fluorescent Protein Voltage Indicators"; Plos One; vol. 8, Issue 6, 10 pages (Jun. 2013).
Gonzalez, et al., "Cell-Based Assays and Instrumentation for Screening Ion-Channel Targets", DDT, 1999, vol. 4, No. 9, pp. 431439.
Gordon, et al. "Regulation of Thy- 1 Gene Expression in Transgenic Mice", Cell, 1987, vol. 50, pp. 445-452.
Gorelova et al. , "The course of neural projection from the prefrontal cortex to the nucleus accumbens in the rat ", Neuroscience, 1997, vol. 76, No. 3, pp. 689-706.
Goshen et al. "Dynamics of Retrieval Strategies for Remote Memories", Cell, 2011, Col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.
Grady, et al.; "Age-Related Reductions in Human Recognition Memory Due to Impaired Encoding"; Science; vol. 269, No. 5221, pp. 218-221 (Jul. 14, 1995).
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Han, et al.; "Millisecond-Timescale Optical Control of Neural Dynamics in the Nonhuman Primate Brain"; Neuron; vol. 62, pp. 191-198 (Apr. 30, 2009).
Han, et al.; "Multiple-Color Optical Activation, Silencing, and Desynchronization of Neural Activity with Single-Spike Temporal Resolution", PLoS One, 2007, vol. 2, No. 3, pp. 1-12.
Han, et al.; "Optogenetics in the nonhuman primate"; Prog. Brain Res.; vol. 196, pp. 215-233 (2012).
Han, et al.; "Two-color, bi-directional optical voltage control of genetically-targeted neurons", CoSyne Abstract Presentation, Presented Feb. 24, 2007.
Han, et al.; "Virogenetic and optogenetic mechanisms to define potential therapeutic targets in psychiatric disorders"; Neuropharmacology; vol. 62, pp. 89-100 (2012).
Hausser, et al. "Tonic Synaptic Inhibition Modulates Neuronal Output Pattern and Spatiotemporal Synaptic Integration", Neuron, 1997, vol. 19, pp. 665- 678.
Hegemann et al., "All-trans Retinal Constitutes the Functional Chromophore in *Chlamydomonas rhodopsin*", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.

(56) References Cited

OTHER PUBLICATIONS

Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in *Schizosaccharomyces pombe* pumps protons through the plasma membrane, " PNAS, 1993, vol. 90, pp. 3578-3582.
Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Johnson-Saliba, et al.; "Gene Therapy: Optimising DNA Delivery to the Nucleus"; Current Drug Targets; vol. 2, pp. 371-399 (2001).
Johnston et al. "Isolation of the yeast regulatory gene GAL4 and analysis of its dosage effects on the galactose/melibiose regulon," PNAS, 1982, vol. 79, pp. 6971-6975.
Jones, et al.; "Animal Models of Schizophrenia"; British Journal of Pharmacology; vol. 164, pp. 1162-1194 (2011).
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. and Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β32-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-10.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.

(56) References Cited

OTHER PUBLICATIONS

Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Knopfel, et al.; "A comprehensive concept of optogenetics"; Progress in Brain Research; vol. 196, pp. 1-28 (2012).
Knopfel, et al.; "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "Remote control of cells"; Nature Nanotechnology; vol. 5, pp. 560-561 (Aug. 2010).
Knox, et al.; "Heterologous Expression of *Limulus* Rhodopsin"; The Journal of Biological Chemistry; vol. 278, No. 42, pp. 40493-40502 (Oct. 17, 2003).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kravitz, et al.; "Regulation of parkinsonian motor behaviours by optogenetic control of basal ganglia circuitry"; Nature; vol. 466, No. 622, 8 pages (Jul. 29, 2010).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Li et al., "Surface Expression of Kv1 Channels is Governed by a C-Terminal Motif", J. Biol. Chem. (2000), 275(16):11597-11602.

Li, et al.; "A Method for Activation of Endogenous Acid-sensing Ion Channel 1 a (ASIC1a) in the Nervous System with High Spatial and Temporal Precision"; The Journal of Biological Chemistry; vol. 289, No. 22, pp. 15441-15448 (May 30, 2014).
Lim et al., "A Novel Targeting Signal for Proximal Clustering of the Kv2.1 K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Lin, et al.; "Characterization of Engineered Channelrhodopsin Variants with Improved Properties and Kinetics"; Biophysical Journal; vol. 96, No. 5, pp. 1803-1814 (Mar. 2009).
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Luo, et al.; "Synthetic DNA delivery systems"; Nature Biotechnology; vol. 18, pp. 33-37 (Jan. 2000).
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Maestripieri, et al.; "A modest proposal: displacement activities as an indicator of emotions in primates"; Anim. Behav.; vol. 44, pp. 967-979 (1992).
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Masaki, et al.; "β2-Adrenergic Receptor Regulation of the Cardiac L-Type Ca2+ Channel Coexpressed in a Fibroblast Cell Line"; Receptor; vol. 5, pp. 219-231 (1996).
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.

(56) References Cited

OTHER PUBLICATIONS

Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using Drosophila Rh1-bovine rhodopsin chimeras," Vision Res., 2006, vol. 46, No. 27: pp. 4575-4581.
Nelson, et al.; "Non-Human Primates: Model Animals for Developmental Psychopathology"; Neuropsychopharmacology; vol. 34, No. 1, pp. 90-105 (Jan. 2009).
Nieh et al., "Optogenetic dissection of neural circuits underlying emotional valence and motivated behaviors", Brain Research, E-pub 2012, 1511:73-92.

Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Palu, et al.; "In pursuit of new developments for gene therapy of human diseases"; Journal of Biotechnology; vol. 68, pp. 1-13 (1999).
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.

(56) References Cited

OTHER PUBLICATIONS

Pfeifer, et al.; "Gene Therapy: Promises and Problems"; Annu. Rev. Genomics Hum. Genet.; vol. 2, pp. 177-211 (2001).
Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Powell, et al.; "Schizophrenia-Relevant Behavioral Testing in Rodent Models: A Uniquely Human Disorder?"; Biol. Psychiatry; vol. 59, pp. 1198-1207 (2006).
Qiu et al. " Induction of photosensitivity by heterologous expression of melanopsin", Nature, 2005, vol. 433: pp. 745-749.
Racaniello; "How many viruses on Earth?"; Virology Blog; 6 pages; http://www.virology.ws/2013/09/06/how-many-viruses-on-earth/ (Sep. 6, 2013).
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl- cotransporter KCC2 and Impairs Neuronal Cl-Extrusion", The Journal of Cell Biology, 2002, vol. 159: pp. 747-752.
Rogers, et al.; "Effects of ventral and dorsal CA1 subregional lesions on trace fear conditioning"; Neurobiology of Learning and Memory; vol. 86, pp. 72-81 (2006).
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.

Salzman, et al."Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Shimizu, et al.; "NMDA Receptor-Dependent Synaptic Reinforcement as a Crucial Process for Memory Consolidation"; Science; vol. 290, pp. 1170-1174 (Nov. 10, 2000).
Shoji, et al.; "Current Status of Delivery Systems to Improve Target Efficacy of Oligonucleotides"; Current Pharmaceutical Design; vol. 10, pp. 785-796 (2004).
Sigmund; "Viewpoint: Are Studies in Genetically Altered Mice Out of Control?"; Arterioscler Thromb Vasc Biol.; vol. 20, No, 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Sineshchekov et al.; "Intramolecular Proton Transfer in Channelrhodopsins"; Biophysical Journal; vol. 104, No. 4, pp. 807-817 (Feb. 2013).
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).

(56) References Cited

OTHER PUBLICATIONS

Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Smith, et al.; "Proton binding sites involved in the activation of acid-sensing ion channel ASIC2a"; Neuroscience Letters; vol. 426, pp. 12-17 (2007).
Sofuoglu, et al.; "Cholinergic Functioning in Stimulant Addiction: Implications for Medications Development"; CNS Drugs; vol. 23, No. 11, pp. 939-952 (Nov. 1, 2009).
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Steimer; "The biology of fear- and anxiety-related behaviors"; Dialogues in Clinical Neuroscience; vol. 4, No. 3, pp. 231-249 (Sep. 2002).
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Stuber; "Dissecting the neural circuitry of addiction and psychiatric disease with optogenetics"; Neuropsychopharmacology; vol. 35, No. 1, pp. 341-342 (2010).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.

Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
Tsuchida; "Nervous Control of Micturition"; The Japanese Journal of Urology; vol. 80, No. 9, pp. 1257-1277 (1989).
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Uniprot Accession No. P02945, integrated into the database on Jul. 21, 1986.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Verma, et al.; "Gene therapy—promises, problems and prospects"; Nature; vol. 389, pp. 239-242 (Sep. 1997).
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.I-19.39.
Wall, "Transgenic livestock: Progress and prospects for the future", Theriogenology, 1996, vol. 45, pp. 57-68.
Wang, et al. "Direct-current Nanogenerator Driven by Ultrasonic Waves," Science, 2007, vol. 316, pp. 102-105.
Wang, et al., "High-speed mapping of synaptic connectivity using photostimulation in Channelrhodopsin-2 transgenic mice", PNAS, 2007, vol. 104, No. 19, pp. 8143-8148.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

(56) References Cited

OTHER PUBLICATIONS

Wang, et al., "Mrgprd-Expressing Polymodal Nociceptive Neurons Innervate Most Known Classes of Substantia Gelatinosa Neurons", J Neurosci, 2009, 29(42):13202-13209.
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Wang, et al.; "Simultaneous phase and size control of upconversion nanocrystals through lanthanide doping"; Nature; vol. 463, No. 7284, pp. 1061-1065 (Feb. 25, 2010).
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Weiss, et al.; "Galanin: A Significant Role in Depression?"; Annals New York Academy of Sciences; vol. 863, No. 1, pp. 364-382 (1998).
Wells et al. "Application of Infrared light for in vivo neural stimulation," Journal of Biomedical Optics, 2005, vol. 10(6), pp. 064003-1-064003-12.
Williams et al., "From optogenetic technologies to neuromodulation therapies", Sci Transl Med., 2013, 5(177):177.
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Witten et. al., "Cholinergic Interneurons Control Local Circuit Activity and Cocaine Conditioning", Science, 2010, vol. 330, No. 6011: pp. 1677-1681.
Witten et. al., Supporting Online Material for: "Cholinergic Interneurons Control Local Circuit Activity and Cocaine Conditioning", Science, 2010, vol. 330: 17 pages.
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Written opinion of PCT Application No. PCT/US2011/059383 (dated May 9, 2012).
Xiong et al., "Interregional connectivity to primary motor cortex revealed using MRI resting state images", Hum Brain Mapp, 1999, 8(2-3):151-156.
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et al., "Optogenetics in neural systems", Neuron Primer, vol. 71, No. 1, pp. 9-34 (Jul. 14, 2011).
Yizhar et. al., "Neocortical excitation/inhibition balance in information processing and social dysfunction", Nature, 2011, vol. 477, pp. 171-178; and Supplemental Materials; 41 pages.

Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Zhang "Multimodal fast optical interrogation of neural circuitry," Nature, 2007, vol. 446, pp. 633-641.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang, et al., "The Microbial Opsin Family of Optogenetic Tools", Cell, 2011, vol. 147, No. 7, pp. 1146-1457.
Zhang, et al.; "Optogenetic interrogation of neural circuits: Technology for probing mammalian brain structures"; Nature Protocols; vol. 5, No. 3, pp. 439-456 (Feb. 18, 2010).
Zhao, et al., "Improved Expression of Halorhodopsin for Light-Induced Silencing of Neuronal Activity", Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Duvarci, et al "The bed Nucleus of the Stria Terminalis Mediates inter-individual variations in anxiety and fear", J. Neurosci., 29(33) 10357-10361 (2009).
Matsuda "Bed nucleus of stria terminalis (BNST)" Benshi Seishin Igaku (Molecular Psychiatric Medicine), 2009, vol. 9 No. 3, p. 46-49.
Neuropsychopharmacology, 2011, vol. 36 No. Suppl.1, p. S110 (Abstract No. 67).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).
Packer et al., (2015) "Simultaneous all-optical manipulation and recording of neural circuit activity with cellular resolution in vivo," Nature Methods 12(2):141-149.
Co-pending U.S. Appl. No. 15/861,433, filed Jan. 3, 2018.
Co-pending U.S. Appl. No. 15/957,608, filed Apr. 19, 2018.
Co-pending U.S. Appl. No. 15/962,773, filed Apr. 25, 2018.
Co-pending U.S. Appl. No. 16/037,974, filed Jul. 17, 2018.
Co-pending U.S. Appl. No. 16/039,176, filed Jul. 18, 2018.
Co-pending U.S. Appl. No. 16/041,647, filed Jul. 20, 2018.
Co-pending U.S. Appl. No. 16/052,482, filed Aug. 1, 2018.
Co-pending U.S. Appl. No. 16/112,202, filed Aug. 24, 2018.
Belzung et al., "Optogenetics to study the circuits of fear- and depresssion-like behaviors: A critical analysis," Pharmacology, Biochemistry and Behavior, 2014, 122: 144-157.
Bernstein & Boyden "Optogenetic tools for analyzing the neural circuits of behavior," Trends Cogn Sci., 2011 15(12): 592-600.

\* cited by examiner

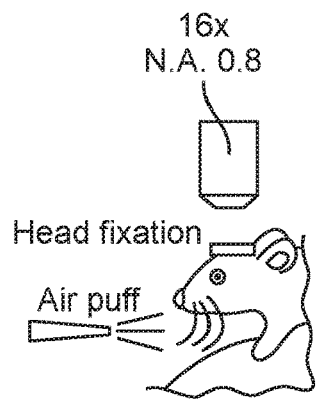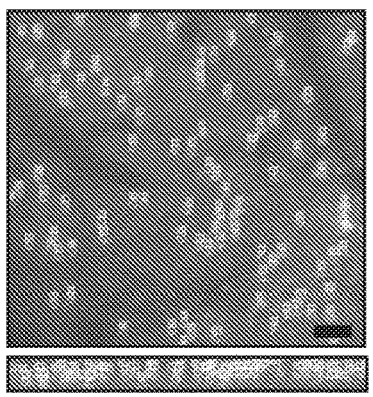
FIG. 4A          FIG. 4B
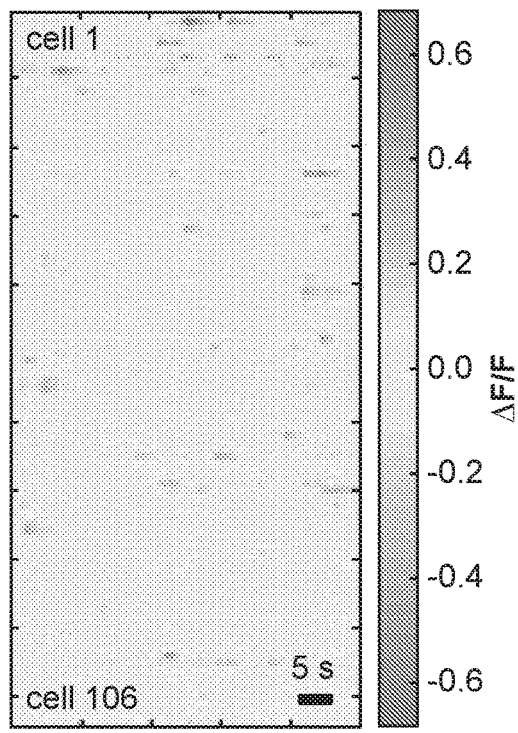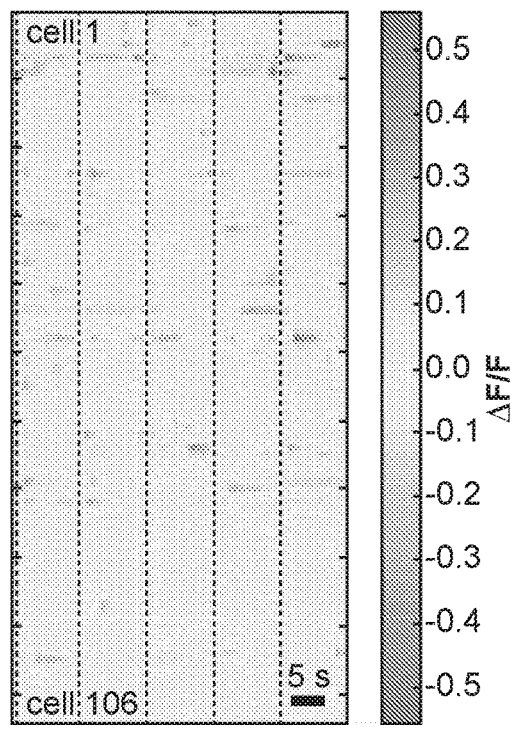
FIG. 4C          FIG. 4D
FIG. 4E

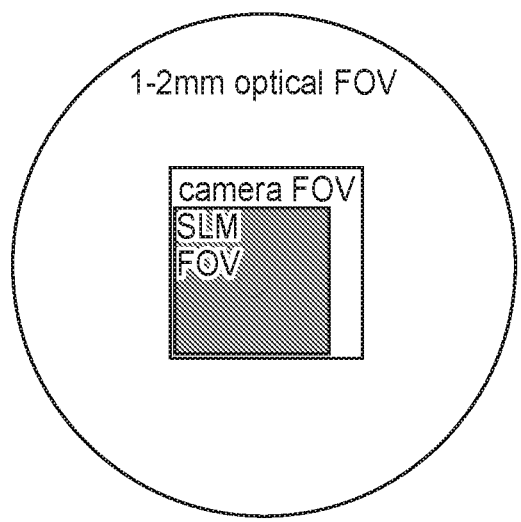
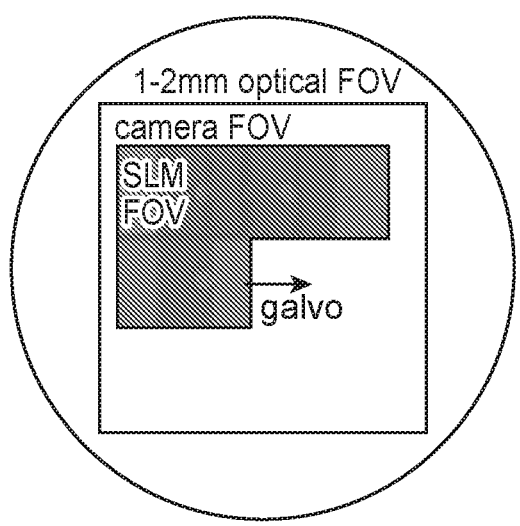
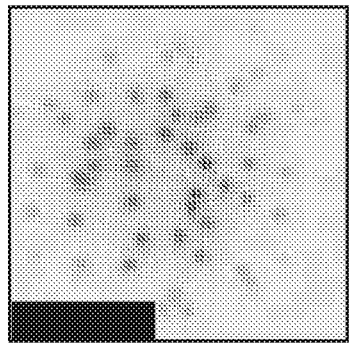
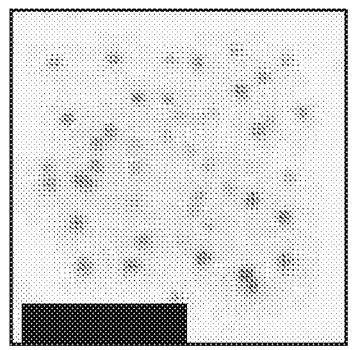
FIG. 5A                    FIG. 5B

FIG. 9A                    FIG. 9B

METHODS AND DEVICES FOR IMAGING AND/OR OPTOGENETIC CONTROL OF LIGHT-RESPONSIVE NEURONS

CROSS-REFERENCE TO RELATED APPLICATIONS

Pursuant to 35 U.S.C. § 119(e), this application claims the benefit of U.S. Provisional Patent Application No. 62/183,012, filed Jun. 22, 2015, which application is incorporated herein by reference in its entirety.

INTRODUCTION

Fluorescent indicators of neuronal activity and optogenetic tools are increasingly used to optically measure and control neuronal activity, respectively, in neurons. Methods for optical recording of neural activity at single cell resolution in three dimensions include serial scanning techniques such as two photon microscopy and wide field detection techniques such as light sheet and light field microscopy.

Two-photon microscopy is a multiphoton fluorescence technique, in which red-shifted excitation light is used to excite fluorescent molecules in a sample. In two-photon microscopy, two photons of light are absorbed for each excitation.

In carrying out light sheet microscopy, a thin slice of the sample is illuminated perpendicularly to the direction of observation, where the illumination is provided by a laser beam that is focused only in one direction (i.e., a light sheet). In light field microscopy, a microlens array is inserted in to the optical path of a conventional microscope, which allows creation of focal stacks from a single image.

SUMMARY

A method for measuring the activity of one or more individual excitable cells, e.g., neurons, in a target tissue is provided. The present method may include measuring the activity of selected excitable cells by projecting one or more three dimensional (3D) multi-focal laser light patterns into a target tissue containing excitable cells adapted to emit cellular electrical activity-sensitive fluorescence, to generate a multiplexed 2D diffraction pattern of fluorescence emitted by the neurons, and resolving the multiplexed 2D diffraction pattern.

Another aspect of the present disclosure includes a method including the steps of obtaining individual two-dimensional (2D) diffraction patterns of multiple fluorescent excitable cells in a target tissue, and measuring the activity of individual excitable cells by projecting one or more three dimensional (3D) multi-focal laser light pattern into the target tissue to generate a multiplexed 2D diffraction pattern of fluorescence emitted by the neurons, and resolving the multiplexed 2D diffraction pattern using the individual 2D diffraction patterns. Also provided herein is a system configured to perform the present methods, the system including a microscope configured to project a 3D multi-focal laser light pattern into a target tissue using a spatial light modulator and a mirror galvanometer, and a microlens array and an image detector to record individual and multiplexed 2D diffraction patterns.

An implementation of the present method may include the steps of i) selecting a first subset of excitable cells in a target tissue for analysis, wherein the target tissue is in a field of view of a microscope and wherein the target tissue comprises a plurality of excitable cells that are adapted to emit fluorescence sensitive to cellular electrical activity, ii) obtaining individual two-dimensional (2D) diffraction patterns for each excitable cell in the first subset of excitable cells by a) contacting an excitable cell in the first subset with a laser light, thereby causing the excitable cell to emit fluorescence, b) directing the emitted fluorescence from the contacted excitable cell through a microlens array to create a 2D diffraction pattern, and c) recording the 2D diffraction pattern, and iii) measuring the activity of individual excitable cells in the first subset by a) projecting one or more three-dimensional (3D) multi-focal laser light patterns into the target tissue, thereby causing at least a subset of excitable cells in the first subset of excitable cells in the target tissue to emit fluorescence, b) directing the fluorescence emitted from the target tissue in response to the one or more 3D multi-focal laser light patterns through the microlens array to generate a multiplexed 2D diffraction pattern, c) recording the multiplexed 2D diffraction pattern, and d) resolving the multiplexed 2D diffraction pattern using the individual 2D diffraction patterns of each individual excitable cell in the at least a subset of excitable cells in the first subset to determine the activity of each individual excitable cell illuminated by the one or more 3D multi-focal laser light patterns. The excitable cell may be a neuron and/or a muscle cell. In some embodiments, the target tissue is an in vivo neuronal tissue. In some cases, the target tissue is a light-scattering tissue. In some embodiments, the at least a subset of excitable cells in the first subset includes 20 or more excitable cells.

In any embodiment, the one or more 3D multi-focal laser light patterns may be configured to illuminate the at least a subset of excitable cells in the first subset with a laser light. In some embodiments, the one or more 3D multi-focal laser light patterns are configured to illuminate all individual excitable cells in the first subset with a laser light.

In any embodiment, the measuring the activity of an individual excitable cell may be performed at a frequency of from about 10 Hz to about 100 Hz.

In any embodiment, resolving the multiplexed 2D diffraction pattern may include deconvolving the multiplexed 2D diffraction pattern using the individual 2D diffraction patterns of each individual excitable cell in the at least a subset of excitable cells in the first subset, thereby resolving the contribution of fluorescence emitted from an individual excitable cell to the multiplexed 2D diffraction pattern. In some embodiments, deconvolving the multiplexed 2D diffraction pattern comprises determining individual point spread functions (PSFs) for each of the individual 2D diffraction patterns of each individual excitable cell in the at least a subset of excitable cells in the first subset and using the individual PSFs to deconvolve the multiplexed 2D diffraction pattern.

In any embodiment, projecting the one or more 3D multi-focal laser light patterns may include splitting a laser beam and projecting the one or more 3D multi-focal laser light patterns using a spatial light modulator. In some embodiments, the measuring step includes sequentially projecting each set of a plurality of sets of one or more 3D multi-focal laser light patterns into the target tissue. In some embodiments, each set of the plurality of sets of one or more 3D multi-focal laser light patterns is sequentially projected into the target tissue at a rate of from about 0.3 to about 0.8 times the maximum switching rate of the spatial light modulator. In some embodiments, each set of the plurality of sets of one or more 3D multi-focal laser light patterns is configured to contact a subset of excitable cells in the first subset of excitable cells, and wherein the method further comprises selecting members of each subset of excitable cells based on the individual 2D diffraction patterns. In some embodiments, the selecting step includes comparing the individual 2D diffraction patterns among each other, and selecting members of each subset such that the difference in the individual 2D diffraction pattern between any two excitable cells within the subset of excitable cells is above a threshold. In some embodiments, sequentially projecting each set of the plurality of sets of one or more 3D multi-focal laser light patterns into the target tissue includes horizontally translating the field of view of the spatial light modulator using a mirror galvanometer to project each set of the plurality of sets of one or more 3D multi-focal laser light patterns into at least two distinct sites in the target tissue. In some embodiments, the plurality of sets of one or more 3D multi-focal laser light patterns collectively illuminates excitable cells in a volume of the target tissue at least 1.5 times larger than the maximum volume of the target tissue that can be illuminated without horizontally translating the field of view of the spatial light modulator.

In any embodiment, the laser beam may be pulsed at a frequency of from about 100 kHz to about 500 kHz. In any embodiment, the laser beam may have an average power of from about 1.0 watts (W) to about 3.0 W. In any embodiment, the laser beam may have a pulse duration of from about 100 femtoseconds (fs) to about 500 fs. In any embodiment, the laser light may have a wavelength in the near-infrared range.

In any embodiment, recording the 2D diffraction pattern may include recording an image of the 2D diffraction pattern using an image detector. In some embodiments, the image detector may be a Complementary Metal Oxide Semiconductor (CMOS) detector, e.g., a CMOS camera.

In any embodiment, the method may include, before step i), placing the target tissue in the field of view of the microscope.

In any embodiment, each excitable cell of the first subset of the excitable cells may include an activity-regulated fluorescent dye or fluorescent protein. In some embodiments, each excitable cell of the first subset of the excitable cells expresses a genetically encoded fluorescent protein. In some embodiments, the activity-sensitive fluorescent dye or fluorescent protein is calcium-sensitive or voltage-sensitive.

In any embodiment, the method may include the steps of stimulating the target tissue, and measuring the activity of individual excitable cells in the first subset in response to the stimulation. In some embodiments, the target tissue includes a plurality of excitable cells in the first subset of excitable cells that are adapted to hyperpolarize and/or depolarize in response to a laser light stimulus, and the stimulating includes contacting the plurality of excitable cells with a laser light stimulus. In some embodiments, an excitable cell that is adapted to hyperpolarize and/or depolarize in response to a laser light stimulus is genetically modified to express one or more light-responsive polypeptides that hyperpolarize or depolarize the excitable cell when contacted by a laser light.

Also provided herein is a method of regulating the activity of a plurality of excitable cells in a target tissue, including: i) measuring the activity of a plurality of activity-sensitive fluorescence-emitting excitable cells in a target tissue containing a plurality of excitable cells, according to any method described above, and ii) modulating the activity of a plurality of excitable cells in the target tissue in response to the measured activity of the plurality of activity-sensitive fluorescence-emitting excitable cells. In some embodiments, the plurality of excitable cells are genetically modified to hyperpolarize and/or depolarize in response to a laser light stimulus, and the modulating includes contacting at least a subset of the plurality of genetically modified excitable cells with a laser light stimulus using one or more 3D multi-focal laser light pattern stimuli, wherein the one or more 3D multi-focal laser light pattern stimuli are controlled in response to the measured activity of the at least a subset of the plurality of activity-sensitive fluorescence-emitting excitable cells.

Also provided herein is a system for measuring the activity of one or more excitable cells in a target tissue, the system, including a light microscope, one or more laser light sources, one or more spatial light modulators, one or more mirror galvanometers, a microlens array, an image detector, a controller, a processor, and a computer-readable medium comprising instructions that, when executed by the processor, cause the controller to perform any method described above. In certain embodiments, the microscope is configured to project one or more 3D multi-focal laser light patterns generated by a spatial light modulator and reflected off a mirror galvanometer into a target tissue that is in the field of view of the microscope, and is configured to direct light emitted from the target tissue through a microlens array onto an image detector.

In any embodiment, the one or more laser light sources may include a regenerative amplifier.

In any embodiment, the one or more laser light sources may be configured to produce a laser beam pulsed at a frequency of from about 100 kHz to about 100 MHz. In any embodiment, the one or more laser light sources may be configured to produce pulses of a laser beam having a duration of from about 100 fs to about 500 fs. In any embodiment, the one or more laser light sources may be configured to produce pulses of a laser beam having a wavelength in the near-infrared range.

In any embodiment, the spatial light modulator may be configured to split a laser beam generated by the one or more laser light sources into a plurality of laser lights and to generate the one or more 3D multi-focal laser light patterns projected into the target tissue.

In any embodiment, the one or more mirror galvanometers may be configured to project the one or more 3D multi-focal laser light patterns into the sample across a plurality of spatially distinct fields of view of the spatial light modulator.

In any embodiment, the image detector may be a Complementary Metal Oxide Semiconductor (CMOS) detector, e.g., a CMOS camera.

In any embodiment, the system further includes a zero order beam block configured to block zero order undiffracted laser light projected from the one or more spatial light modulators.

In any embodiment, the controller may measure the activity of each individual excitable cell among a plurality of excitable cells measured collectively at a frequency of from about 10 Hz to about 100 Hz.

Also provided herein is a method for collectively and specifically illuminating a plurality of individual excitable cells in a target tissue, the method including the steps of i) selecting a first subset of excitable cells in a target tissue for analysis, wherein the target tissue is in a field of view of a microscope and wherein the target tissue includes a plurality of excitable cells that are adapted to emit fluorescence, and ii) sequentially projecting each 3D multi-focal laser light pattern of a plurality of 3D multi-focal laser light patterns generated by a spatial light modulator into the target tissue, wherein the plurality of 3D multi-focal laser light patterns is projected into at least two distinct sites in the target tissue, thereby collectively and specifically illuminating the plurality of excitable cells in the target tissue. In some embodiments, the method includes horizontally translating the field of view of the spatial light modulator using a mirror galvanometer to project the 3D multi-focal laser light patterns into the at least two distinct sites in the target tissue. In some embodiments, the target tissue includes a plurality of excitable cells that are adapted to hyperpolarize and/or depolarize in response to illumination by the laser light. In some embodiments, an excitable cell that is adapted to hyperpolarize and/or depolarize in response to a laser light stimulus is genetically modified to express one or more light-responsive polypeptides that hyperpolarize or depolarize the excitable cell when illuminated by the laser light.

BRIEF DESCRIPTION OF THE DRAWINGS

The present disclosure may be best understood from the following detailed description when read in conjunction with the accompanying drawings. Included in the drawings are the following figures:

FIGS. 4A-4E are collection of images and graphs showing simultaneous 3D recording of activity in multiple neurons in an in vivo, neuronal target tissue, according to embodiments of the present disclosure.

FIGS. 5A-5B are collection of images showing the increased field of view achieved by spatial-temporal multiplexing, according to embodiments of the present disclosure.

DEFINITIONS

Figure 1A:
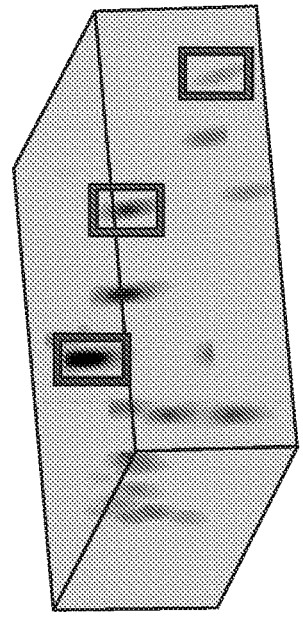
FIGS. 1A-1D are a collection of images depicting a scanless three-dimensional (3D) two-photon imaging system and the steps of using the system according to embodiments of the present disclosure.

The term "about" as used herein when referring to a measurable value such as a physical quantity, a temporal duration, a frequency and the like, is meant to encompass variations of ±20%, such as ±10%, such as ±5%, ±1%, including ±0.1% from the specified value, as such variations are typical of measurements characterizing the disclosed systems or appropriate to perform the disclosed methods.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

The terms "polypeptide", "peptide" and "protein" are used interchangeably herein to refer to polymers of amino acids of any length. The polymer may be linear, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product," depending on the context.

The term "genetic modification" refers to a permanent or transient genetic change induced in a cell following introduction into the cell of a heterologous nucleic acid (i.e., nucleic acid exogenous to the cell). Genetic change ("modification") can be accomplished by incorporation of the heterologous nucleic acid into the genome of the host cell, or by transient or stable maintenance of the heterologous nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The terms "light-activated," "light-responsive" in reference to a polypeptide or protein that is light-responsive, are used interchangeably and include light-responsive ion channels or opsins, and ion pumps as described herein. Such light-responsive proteins may have a depolarizing or hyperpolarizing effect on the cell on whose plasma membrane the protein is expressed depending on the ion permeability of the activated protein, and the electrochemical gradients present across the plasma membrane.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Excitable cell," as used herein, refers to electrically excitable cells, such as neurons and muscle cells. Excitable cells typically use changes in their membrane potential to transmit signals within the cell. Thus, an excitable cell may be characterized in having a resting state, where the membrane potential is at the resting membrane potential, and an excited state, where rapid depolarization of the membrane potential is transmitted across the cell as an action potential. The "cellular electrical activity" of an excitable cell may refer to the changes in the membrane potential or may refer to any indirect measure of the changes in membrane potential, such as the changes in intracellular calcium concentration or any other biochemical changes that is a functional measure of the change in the membrane potential.

"Target tissue," as used herein, includes any tissue or portion thereof that is of interest and suitable for performing the present method. The target tissue may be an in vivo tissue, e.g., a part of the brain of a moving or immobilized animal, or may be an in vitro tissue sample, e.g., a brain slice tissue. The target tissue may be from any suitable subject, including fish, amphibian, reptile, bird, and mammal (including human, non-human primate, mouse, rat, etc.), etc.

"Field of view," as used herein, refers to the maximum area over the surface of a target tissue that can be accessed optically by a component of the present microscope system when the relative position of the target tissue and the component is fixed. In some cases, the field of view of a spatial light modulator is within the field of view of the image detector, which is in turn in the field of view of the microscope.

"Adapted," as used in reference to a neuron adapted to perform a particular function, refers to the neuron being modified, e.g., genetically modified and/or otherwise being made to associate with a functional moiety, such as a fluorescent dye, to carry out the function.

"Fluorescence sensitive to cellular electrical activity," as used herein, refers to one or more properties of the fluorescence emitted by an excitable cell, where changes in the membrane potential of the excitable cell can be measured, directly or indirectly, by a change in the fluorescence emitted. Indirect measures of cellular electrical activity may include changes in the intracellular calcium or other ion concentration, changes in biochemical activity caused by changes in the membrane potential, etc. The change in fluorescence may be a change in the intensity, wavelength, etc., of the fluorescence. (e.g., changes in).

"Distinct," as used herein, includes a difference in whole or in part. As such, "distinct" includes "overlapping but different". In some cases, something that is distinct from another may be measurably distinct in that particular system.

"Image detector," as used herein, refers to any device that includes an optical sensor for detecting a two dimensional image formed by the incident electromagnetic radiation. Thus the image detector may detect in two dimensions the electromagnetic radiation impinging upon a focal plane positioned on the optical sensor. In certain cases, an image detector excludes devices, e.g., photomultiplier tubes (PMTs), that are configured to detect electromagnetic radiation without regard to the location of the source of radiation within the imaged target.

"Collectively," as used herein, modifies an action taken or property to refer to the action taken by, or the property obtained by an ensemble of multiple individual parts. In some cases, multiple actions are taken at least substantially simultaneously with respect to the time scale of a functional output of the system, e.g., relative to the time scale of change in the measured fluorescence that is sufficient to characterize the cellular electrical activity, e.g., neuronal activity, or relative to the time scale of the cellular electrical activity that leads to a behavioral or therapeutic output. In some cases, the actions may be simultaneous or quasi-simultaneous, and may be effectively simultaneous within a given time point of measurement (e.g., as represented by the exposure time of an image detector). Thus in some cases, a collectively measured activity of multiple neurons includes the neuronal activity-sensitive fluorescence of each neuron measured simultaneously for all the neurons, quasi-simultaneously for all the neurons, or sequentially over different subsets of the neurons, at each time point, e.g., as defined by a single exposure of an image detector.

"Pattern," as used herein, refers to a distribution of a signal, e.g., laser light, fluorescence, etc., projected on a two-dimensional (2D) area or into a three-dimensional (3D) space. The signal may be modulated in one or more properties (e.g., amplitude, frequency, polarity, etc.) across the 2D area or 3D space. In some instances, a pattern may exclude a distribution that is substantially uniform throughout the space or area.

DETAILED DESCRIPTION

A method for measuring the activity of one or more individual excitable cells, e.g., neurons, in a target tissue is provided. The present methods and systems employ spatiotemporal multiplexing of 3D holographic illumination, and 3D imaging using a microlens array to extend the field of view and maintain a desirable time-averaged signal for imaging. The present method may include measuring the activity of individual, selected excitable cells by projecting one or more three dimensional (3D) multi-focal laser light patterns into a target tissue containing excitable cells adapted to emit cellular electrical activity-sensitive fluorescence, to generate a multiplexed 2D diffraction pattern of fluorescence emitted by the neurons, and resolving the multiplexed 2D diffraction pattern.

Another aspect of the present disclosure includes a method including obtaining individual two-dimensional (2D) diffraction patterns of multiple fluorescent excitable cells, e.g., neurons, in a target tissue, and measuring the activity of individual excitable cells by projecting one or more three dimensional (3D) multi-focal laser light patterns into the target tissue to generate a multiplexed 2D diffraction pattern of fluorescence emitted by the excitable cells, and resolving the multiplexed 2D diffraction pattern using the individual 2D diffraction patterns.

Also provided herein is a system configured to perform methods of the present disclosure, the system including a microscope configured to project a 3D multi-focal laser light pattern into a target tissue using a spatial light modulator and a mirror galvanometer, and a microlens array and an image detector to record individual and multiplexed 2D diffraction patterns of light emitted from the target tissue.

The present methods and systems may achieve the extended field of view and/or desirable time-averaged signal with a suitable illumination power at the target tissue. In some cases, the power at the target tissue of the 3D multi-focal laser light patterns (e.g., the power of 5 3D multi-focal laser light patterns) used to illuminate all of the selected excitable cells (e.g., total of about 100 cells) is about 500 milliwatts (mW) or less, e.g., about 250 mW or less, about 200 mW or less, about 150 mW or less, about 100 mW or less, including about 80 mW or less. In some embodiments, the power at the target tissue of the 3D multi-focal laser light patterns used to illuminate all of the selected excitable cells is from about 50 mW to about 500 mW, e.g., from about 55 mW to about 250 mW, from about 60 mW to about 200 mW, from about 65 mW to about 150 mW, including from about 70 mW to about 100 mW.

Before the present disclosure is described in greater detail, it is to be understood that embodiments of the present disclosure are not limited to particular examples described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges are presented herein with numerical values being preceded by the term "about." The term "about" is used herein to provide literal support for the exact number that it precedes, as well as a number that is near to or approximately the number that the term precedes.

Unless defined otherwise, all technical and scientific terms used herein have the same meaning as commonly understood by one of ordinary skill in the art to which the subject matter of the present disclosure belongs. Although any methods and materials similar or equivalent to those described herein can also be used in the practice or testing of the present disclosure, representative illustrative methods and materials are now described.

The practice of various embodiments of the present disclosure employs, unless otherwise indicated, conventional techniques of biochemistry, chemistry, molecular biology, microbiology, cell biology, genomics and recombinant DNA, which are within the skill of the art. See Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), and CELL AND TISSUE CULTURE: LABORATORY PROCEDURES IN BIOTECHNOLOGY (Doyle & Griffiths, John Wiley & Sons 1998), the disclosures of which are incorporated herein by reference.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the subject matter of the present disclosure is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

In further describing various aspects of embodiments of the present disclosure in greater detail, aspects of the systems and devices of various embodiments are reviewed first in greater detail, followed by a discussion of methods and kits according to certain embodiments of the present disclosure.

Systems

Figure 13A:
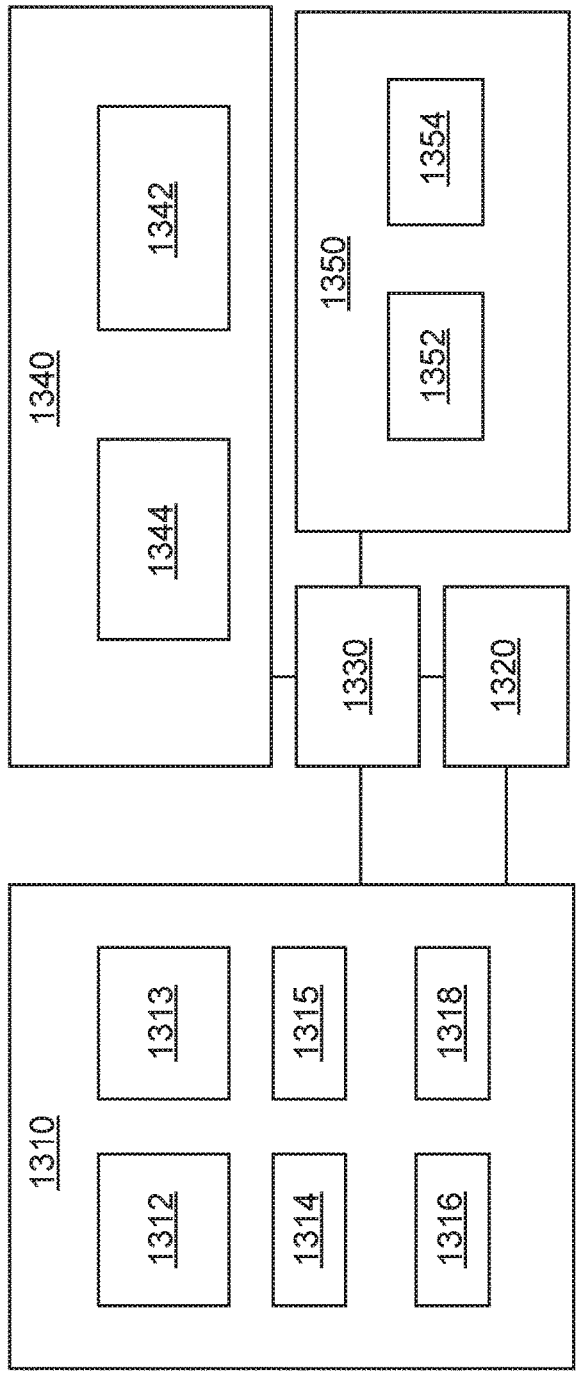
FIGS. 13A-13B are a collection of schematic diagrams depicting a system for illuminating and/or measuring the activity of excitable cells in a target tissue, according to embodiments of the present disclosure.

Aspects of the present disclosure include systems and devices thereof configured for imaging and/or optogenetic control of light-responsive excitable cells, e.g., neurons. With reference to FIG. 13A, the present system may include i) a light microscope 1310 having an excitation path and an emission path with respect to a target tissue, wherein the excitation path includes: a spatial light modulator 1312 for projecting a 3D multi-focal laser light pattern into the target tissue; and a pair of mirror galvanometers 1314, 1315 configured to spatially translate a field of view of the spatial light modulator on the target tissue, and wherein the emission path includes a microlens array 1316 configured to modify fluorescence emitted by the target tissue such that a 2D diffraction pattern is projected onto an image detector 1318, ii) a controller 1320; and iii) a processor 1330. The processor may be configured to execute instructions 1352 that cause the controller to: illuminate the target tissue with different 3D multi-focal light patterns over different fields of view of the spatial light modulator, thereby causing the excitable cells to emit fluorescence, and record a multiplexed 2D diffraction pattern of the emitted fluorescence, and that cause the processor to resolve the recorded multiplexed 2D diffraction pattern.

The spatial light modulator 1312 may be configured to modify light generated from a light source 1313, to generate the 3D multi-focal laser light pattern projected into the target tissue.

In some embodiments, the system further includes input/output interfaces 1340 for a user of the system to enter input parameters and for the system to present outputs (e.g., recorded images, resolved images, measured activity of excitable cells, etc.) to the user. Input interfaces 1342 include, without limitation, a keyboard, mouse, touch pad, touch screen etc. Output interfaces 1344 include, without limitation, a screen, touch screen, speaker, indicator lights, etc. The system may further include a suitable computer-readable medium 1350 (e.g., a non-transient memory) storing the instructions 1352 as well as any input parameters 1354 that may be entered into the system by a user.

Figure 13B:
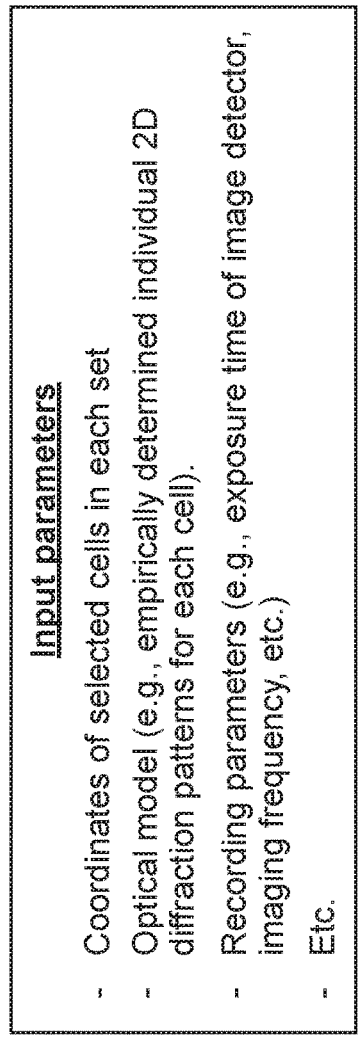

The input parameters may be any parameter that may be desirable to specify for illuminating and/or measuring activity of excitable cells in a particular target tissue, as described herein. Input parameters may include, without limitation, the coordinates of selected excitable cells in the target tissue for each set representing a field of view of the spatial light modulator; the optical model that can be used for resolving the multiplexed 2D diffraction patterns (such as an empirically determined 2D diffraction patterns for each individual cell that is selected for illumination; parameters for recording the multiplexed 2D diffraction patterns (e.g., exposure time of the image detector), etc. (see also, FIG. 13B).

In some embodiments, the subject systems include a light microscope, one or more laser light sources, one or more spatial light modulators, one or more mirror galvanometers, a microlens array, an image detector, a controller, a processor, and a computer-readable medium comprising instructions that, when executed by the processor, cause the controller to carry out one or more of the subject methods, described further herein. Each of these components is now described in greater detail, with further reference made to FIG. 1A or FIG. 8.

As summarized above, aspects of the present disclosure include a system that includes a light microscope. The light microscope may be configured to optically probe in three dimensions, using one or more three-dimensional (3D) multi-focal laser light patterns, a target tissue that is in the field of view of the microscope. The target tissue may contain excitable cells, e.g., neurons, that are adapted to emit fluorescence, e.g., a two-photon excited fluorescence emission, when illuminated by an appropriate laser light. Thus, the light microscope may include a multi-focal near-infrared (NIR) excitation path and a visible detection path.

Figure 8:
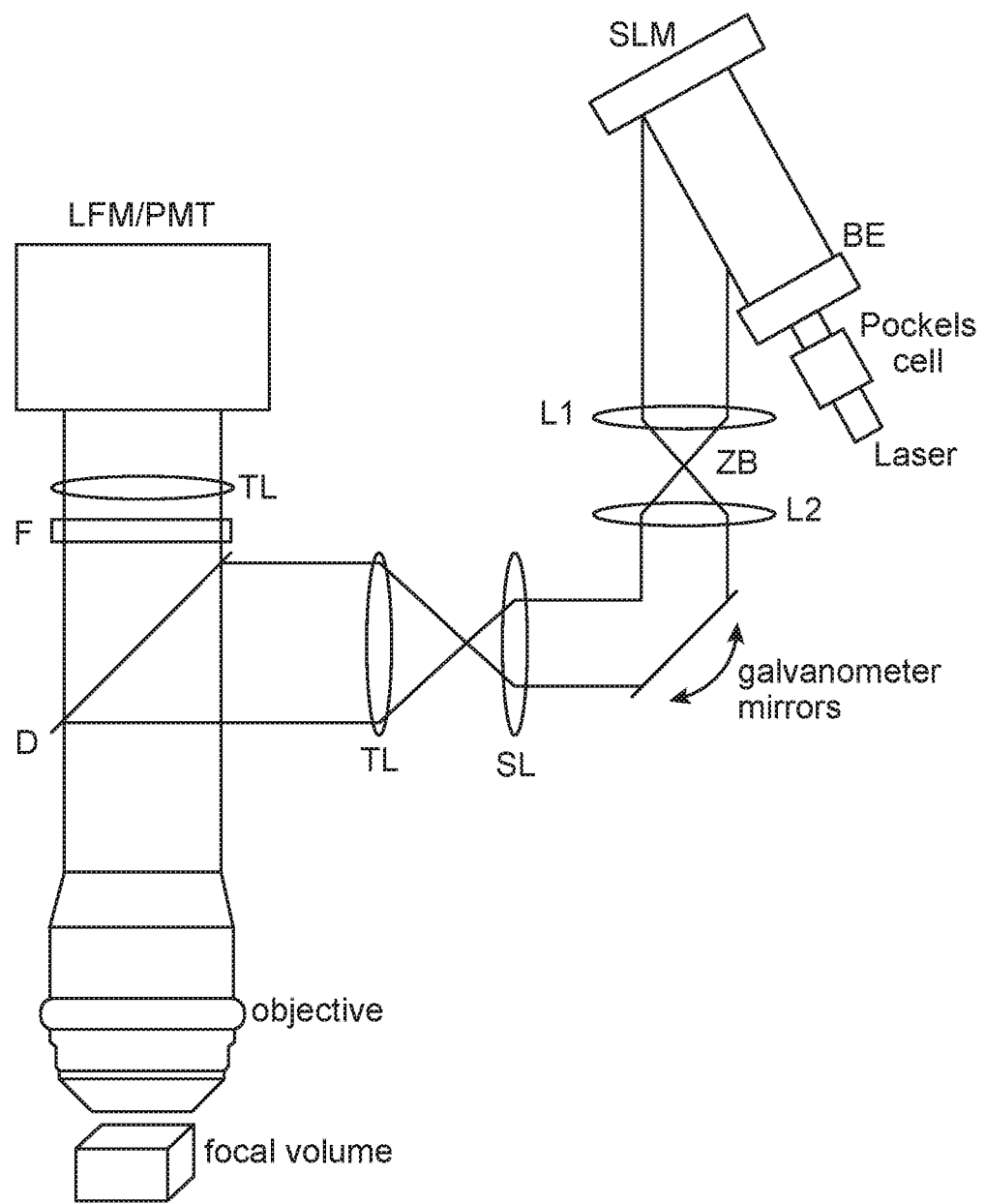
FIG. 8 is a schematic diagram showing an optical layout of a microscope setup for performing 3D Holographic Illumination with Time-Division Multiplexing, according to embodiments of the present disclosure.

The multi-focal near-infrared (NIR) excitation path includes one or more laser light sources, one or more spatial light modulators (FIG. 1A and FIG. 8, "SLM") and one or more mirror galvanometers (FIG. 1A, "GM"). The laser light source produces a laser beam with wavelength in the NIR range (from about 700 nm to about 2500 nm) and the laser beam is directed to a spatial light modulator (SLM), e.g., a phase spatial light modulator. The system may include a beam expander (as shown in FIG. 8, "BE"), e.g., an achromatic doublet, to expand the laser beam to cover the spatial light modulator. The spatial light modulator may be programmed with a phase mask that causes the laser beam to split into multiple beamlets (i.e., causes the laser beam to be spatially modulated in phase and/or amplitude) and thereby project any arbitrary 3D multi-focal laser light pattern into the target tissue placed in the focal volume. The beamlets are reflected off of a pair of mirror galvanometers (GM) positioned between the spatial light modulator and the target tissue. The mirror galvanometers are configured such that the 3D multi-focal laser light pattern may be projected into multiple distinct locations within the target tissue. In some cases, the spatially modulated laser beam is projected and focused onto a midpoint between the two mirror galvanometers which are spaced about 1 cm apart. The mirror galvanometers may have a mirror of any suitable size to hold the laser beam diameter over the angular range used (e.g., the mirror aperture may be in the range of about 3 mm to about 50 mm, e.g., about 3 mm to about 20 mm, about 3 mm to about 10 mm, including about 3 mm to about 7 mm).

The light microscope is configured to direct fluorescence emitted from the excitable cells in the target tissue upon illumination of the target tissue by the 3D multi-focal laser light pattern through the visible detection path. The visible detection path may include a diffractive optical element, e.g., a microlens array (FIG. 1A, "MLA"), that forms a two-dimensional (2D) diffraction pattern of the fluorescence emitted from the target tissue onto the optical sensor of an image detector, e.g., a scientific Complementary Metal Oxide Semiconductor (sCMOS) camera (FIG. 1A, "sCMOS").

The laser light source may be any convenient laser light source for use in the present system and method. In certain embodiments, the laser light source generates a laser beam having a wavelength in the near-infrared (NIR) range (e.g., about 700 nm to about 2500 nm, 800 nm to 1500 nm, including 850 nm to 1000 nm). In some embodiments, the wavelength of the laser beam produced by the laser light source is tunable within its operating range. In certain embodiments, the laser light source generates a laser beam having a pulse duration in the range of about 10 fs to about 1000 fs, e.g., about 50 fs to about 800 fs, about 100 fs to about 500 fs, about 100 fs to about 350 fs, including about 150 fs to about 250 fs.

The laser light source may be any suitable laser light source for use in the present system. In certain embodiments, the laser light source is a solid state laser, e.g., a mode-locked Titanium (Ti):Sapphire laser, such as those manufactured by Spectra-Physics of Mountain View Calif. or by Coherent, Inc. of Santa Clara, Calif. Other suitable laser sources may include a dye laser, semiconductor laser (e.g., a diode laser), or a fiber laser, as described in, e.g., PCT Pub. No. WO2014/20513, which is incorporated herein by reference.

In certain embodiments, the laser light source includes a regenerative amplifier. The regenerative amplifier may be configured to receive a first seed laser beam and generate a second laser beam that has a higher pulse energy but lower average power than the first seed laser beam. In some cases, the laser light source includes a multipass amplifier as an alternative to the regenerative amplifier, or in conjunction with the regenerative amplifier. Any convenient regenerative amplifier and/or multipass amplifier may be used in the present system, as described in, e.g., U.S. Pat. No.

RE042499; and U.S. App. Pub. No. 20070053401, which are incorporated herein by reference, and provided by Coherent (Santa Clara, Calif.).

In certain embodiments, the laser light source generates a laser beam pulsed at a frequency of about 100 MHz or less, including about 1 MHz or less, e.g., about 500 kHz or less, about 400 kHz or less, including about 300 kHz or less. In certain embodiments, the laser light source generates a laser beam pulsed at a frequency in the range of about 100 kHz to about 100 MHz, e.g., about 50 MHz to about 90 MHz, about 100 kHz to about 500 kHz, about 150 kHz to about 350 kHz, including about 200 kHz to about 300 kHz.

In some cases, the light source, e.g., laser light source, is configured to generate light, e.g., laser beam, having different properties, such as different pulse frequencies. A removable mirror (FIG. 1A, "RM1") may be used to select between a first light and a second light having different properties, based on the position of the removable mirror.

In certain embodiments, the laser light source generates a laser beam with an average power in the range of about 1.0 W to 6.0 W, e.g., about 2.0 W to 5.5 W, about 1.4 W to 2.5 W, including about 1.6 to 2.0 W.

In certain embodiments, the system includes at least two laser light sources, at least one for use in measuring the activity of a plurality of activity-sensitive fluorescence-emitting excitable cells, e.g., neurons, in a target tissue, and at least one for use in performing standard two-photon scanning microscopy and/or photo-stimulation of excitable cells, as described below.

The system may include a Pockels cell (FIG. 1A, "PC") configured to receive the laser beam that leaves the laser light source and stabilize the intensity of the laser beam. The Pockels cell may be configured to modify the power of the light, e.g., laser beam, from the light source, e.g., laser light source, such that the 3D multi-focal light patterns collectively have a power at the target tissue of about 500 milliwatts (mW) or less, e.g., about 250 mW or less, about 200 mW or less, about 150 mW or less, about 100 mW or less, including about 80 mW or less, and in some cases, collectively have a power at the target tissue of about 10 mW or more, e.g., about 20 mW or more, about 30 mW or more, about 40 mW or more, about 50 mW or more, including about 70 mW or more. In some cases, the 3D multi-focal light patterns collectively have a power at the target tissue of from about 10 mW to about 500 mW, e.g., about 20 mW to about 250 mW, from about 20 mW to about 200 mW, from about 30 mW to about 200 mW, from about 30 mW to about 150 mW, from about 40 mW to about 100 mW, including from about 50 mW to about 80 mW.

The system may further include half wave plates (FIG. 1A, "HWP") that matches the polarization of the laser beam with that required by the spatial light modulator (FIG. 1A, "SLM").

The spatial light modulator (SLM) may be any suitable spatial light modulator for use in the present system and method. In certain embodiments, the spatial light modulator is a phase spatial light modulator. The phase spatial light modulator may be capable of 0-2π phase modulation of the incident laser light. In certain embodiments, the spatial light modulator may have a resolution of 2000 pixels or less× 2000 pixels or less, e.g., 1500 pixels or less×1500 pixels or less, 1000 pixels or less×1000 pixels or less, including 800 pixels or less×800 pixels or less, and may have a resolution in the ranges of 200 pixels or more×200 pixels or more, e.g., 256 pixels or more×256 pixels or more, 350 pixels or more×350 pixels or more, including 500 pixels or more×500 pixels or more. In certain embodiments, the spatial light modulator has a resolution in the ranges of 200 pixels-2000 pixels×200 pixels-2000 pixels, e.g., 256 pixels-1000 pixels× 256 pixels-1000 pixels, 400 pixels-1000 pixels×400 pixels-1000 pixels, including 500 pixels-800 pixels×500 pixels-800 pixels.

The volume of the tissue in which excitable cells are collectively illuminated by a series of 3D multi-focal laser light patterns (i.e., 3D holographic illumination patterns) according to methods of the present disclosure may depend on the transition time of the spatial light modulator. Thus, the faster the transition time of the spatial light modulator, the more distinct 3D multi-focal laser light patterns may be projected into the tissue over a larger volume, within the exposure time of the image detector. In some cases, the spatial light modulator has a maximum switching rate of at least about 40 Hz, e.g., at least about 50 Hz, at least about 75 Hz, at least about 100 Hz, at least about 120 Hz, at least about 150 Hz, including at least about 200 Hz, In certain embodiments, the spatial light modulator has a maximum switching rate in the range of about 10 Hz to about 200 Hz, e.g., about 15 Hz to about 150 Hz, about 20 Hz to about 120 Hz, including about 20 Hz to about 100 Hz. In certain embodiments, the spatial light modulator has a maximum switching rate of from about 40 Hz about 200 Hz, e.g., about 50 Hz to about 150 Hz, about 100 Hz to about 150 Hz, including about 120 Hz to about 150 Hz. The "maximum switching rate" as used herein, refers to the fastest rate at which the spatial light modulator can transition between spatially modulating a laser light beam to project two or more distinct, predetermined 3D patterns. The rate may be determined based on the time ($t_{SLM}$) taken by the spatial light modulator to achieve about 97% power when transitioning from one illumination pattern to another. Suitable spatial light modulators are provided by, e.g., Meadowlark Optics (Frederick, Colo.) and Hamamatsu (Bridgewater, N.J.).

The present system is configured to image the spatial light modulator using a 2f1+2f2 configuration relay lens pair (FIG. 1A, "L3", "L4"; FIG. 8, "L1", "L2"), onto a first member of the pair of mirror galvanometers and then onto a second member of the pair of mirror galvanometers, where the first and second mirror galvanometers are spaced apart equidistant from the conjugate spatial light modulator plane. Each member of the pair of galvanometers controls the horizontal translation in either the x or y direction of the 3D multi-focal laser light pattern within the field of view of the microscope and the image detector.

The mirror galvanometer may be any suitable mirror galvanometer for use in the present system. Suitable mirror galvanometers include those used in scanning laser microscopes described in, e.g., U.S. Pat. No. 4,734,578; U.S. App. Pub. Nos. 20070171502, 20110279893, which are incorporated herein by reference.

A beam block (FIG. 1A and FIG. 8, "ZB") is positioned between lens f1 and f2 (FIG. 1A, L3, L4; FIG. 8, L1, L2) to block the undiffracted, zero order light from the spatial light modulator.

The image of the spatial light modulator relayed from the mirror galvanometers is directed onto the back aperture of the objective placed over the target tissue via a pair of relay lenses and a short pass dichroic mirror.

Fluorescent light emitted from the target tissue upon illumination with a laser light is directed through the emission path. The emission path may be configured in any suitable manner, such as that described in Broxton et al., 2013, Optics Express 21(21), 25418, which is incorporated herein by reference. The emitted light is directed through the microlens array (MLA) that is placed at the image plane. The emission path may further include a tube lens (FIG. 1A and FIG. 8, "TL") positioned between the objective and the microlens array. The image detector is placed to capture the image at a plane one microlens-focal length behind the microlens array.

The microlens array may be any suitable microlens array for use in the present system. The size of individual lenses in the microlens array may vary from array to array, and within an array may be 50 μm or more×50 μm or more, e.g., 70 μm or more×70 μm or more, 100 μm or more×100 μm or more, and may be 1000 μm or less×1000 μm or less, e.g., 500 μm or less×500 μm or less, including 200 μm or less×200 μm or less. In some embodiments, the size of individual lenses in the microlens array may be in the rages of 50-1000 μm×50-1000 μm, e.g., 80-500 μm×80-500 μm, including 100-200 μm×100-200 μm. The f/number (f/#) of the microlens array, defined as the ratio of the focal length to the distance between two parallel light beams incident on an individual lens of the microlens array at an angle perpendicular to the plane of the lens, may vary and may be 4 or more, e.g., 5 or more, including 8 or more, and may be 100 or less, e.g., 50 or less, including 20 or less. In some embodiments, the f/number of the microlens array may be in the range of 4 to 100, e.g., 5 to 50, including 8 to 15.

The image detector may be any suitable image detector for use in the present system. In some instances, the image detector is a digital camera, such as a CMOS detector, e.g., a scientific CMOS camera, or a charge-coupled device (CCD) detector, e.g., an electron-multiplying CCD (EM-CCD) camera.

The emission path may further include a photodetector, e.g., a photomultiplier tube (FIG. 1A and FIG. 8, "PMT"), configured to receive light emitted from the target tissue upon illumination with a laser light. A second removal mirror (FIG. 1A, "RM2") may be used to select whether the emitted light is directed onto the microlens array and thereby to the image detector, or to the photomultiplier tube.

The present system may include additional components extend the axial field of view. Thus, in some embodiments, the present system includes one or more tunable lenses, in the illumination path, the objective and/or the detection path of the microscope, where the tunable lenses are configured to extend the axial field of view. In some embodiments, the system includes one or more deformable mirrors, where the deformable mirrors are configured to extend the axial field of view.

As summarized above, aspects of the present disclosure include a controller, processor and computer readable medium that are configured or adapted to control or operate one or more components of the subject systems. In some embodiments, a system includes a controller that is in communication with one or more components of the systems, as described herein, and is configured to control aspects of the systems and/or execute one or more operations or functions of the subject systems. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein (e.g., cause the controller to control the spatial light modulator and thereby generate a 3D multi-focal light pattern to illuminate selected excitable cells, control the mirror galvanometers to spatially translate the field of view of the spatial light modulator, record the multiplexed 2D diffraction pattern, and/or cause the processor to resolve a recorded multiplexed 2D diffraction pattern, etc.).

In some embodiments, a system includes a user interface, such as a graphical user interface (GUI), that is adapted or configured to receive input from a user, and to execute one or more of the methods as described herein. In some embodiments, a GUI is configured to display data or information to a user.

In some embodiment, the present system is configured to enable a user to provide one or more inputs to the system to control the various components (e.g., the spatial light modulator, laser light source, galvanometer mirrors, etc.) and/or to set parameters that the processor may use to execute an algorithm for performing a method as described herein.

In certain embodiments, the present system is a closed-loop system for measuring and controlling the activity of one or more excitable cells, e.g., neurons in a target tissue. In such instances, the controller may be programmed to illuminate a first set of excitable cells in the target tissue in response to the measured activity of a second set of excitable cells, according to a method as described herein. The first set and second set of excitable cells may be the same, or different (including different but overlapping) set of cells. The first set of excitable cells (e.g., neurons) may be configured to modulate activity (e.g., neural activity) upon being illuminated by an appropriate light stimulus, by, e.g., expressing a light-responsive polypeptide, as described further herein. Where a laser light illumination (non-spatially modulated, or spatially modulated) is used to modulate activity of the first set of excitable cells and to measure activity of a second set of excitable cells, the system may be configured so that spectral overlap between the modulating and measuring laser light illuminations is minimized.

Methods

Figure 12:
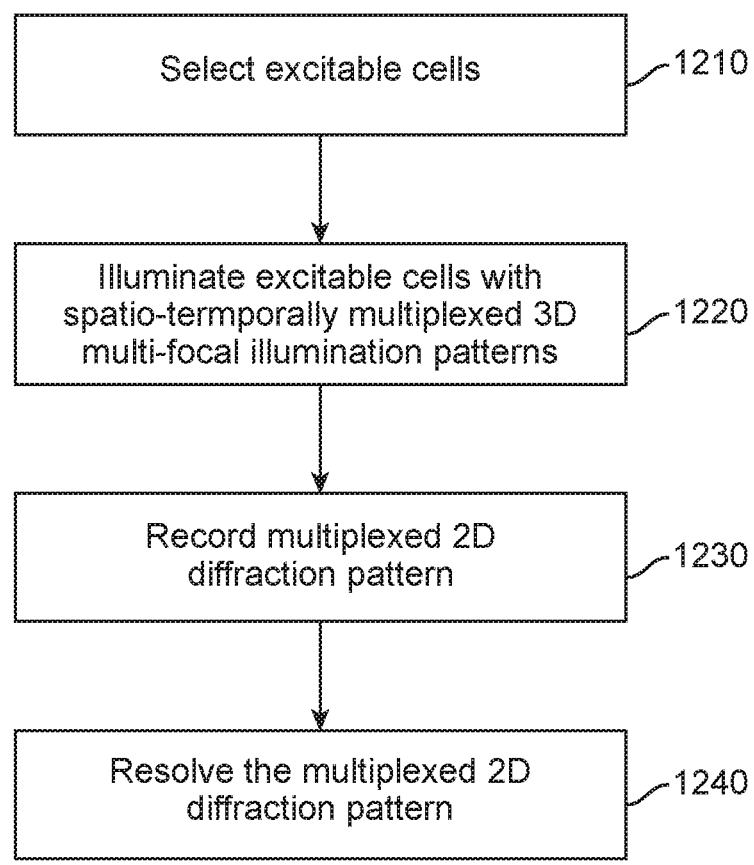
FIG. 12 is a schematic diagram depicting a method of measuring the activity of excitable cells in a target tissue, according to embodiments of the present disclosure.

Aspects of the present disclosure include methods that may be used for imaging and/or optogenetic control of excitable cells, e.g., neurons. With reference to FIG. 12, in general terms, a method of the present disclosure may include selecting 1210 a set of excitable cells, e.g., neurons, that are labeled with a cellular electrical activity-sensitive marker (e.g., a calcium indicator dye or protein) in a target tissue (e.g., a brain), and measuring the activity of each of the selected cells using a spatio-temporally multiplexed 3D holographic illumination 1220 and recording fluorescence signal from the illuminated cells that is further modified by a microlens array, as a multiplexed, 2D diffraction pattern 1230, and resolving the recorded 2D diffraction pattern 1240.

The 3D holographic illumination may be a 3D multi-focal light pattern generated by modifying light projected onto a target tissue using a spatial light modulator, where light is focused on a sub-volume of the total volume accessible within a field of the view of the spatial light modulator. The pattern of the 3D multi-focal light may be predetermined to match the location of excitable cells of interest preselected in the target tissue. Each excitable cell illuminated by the 3D multi-focal light pattern may be illuminated at any suitable portion of the excitable cell for measuring the electrical activity of the cell. Thus, in some cases, an excitable cell, such as a neuron, may be illuminated by the 3D multi-focal light pattern at the cell body (i.e., the region of the cell at and surrounding the location of the nucleus), and/or along an extension of the cell body, such as a neurite (e.g., axon, dendrite, etc.).

Spatio-temporally multiplexed 3D multi-focal light patterns are a collection of individual 3D multi-focal light patterns, each individual 3D multi-focal light pattern being generated by modulation of light projected onto the tissue using the spatial light modulator. The individual 3D multi-focal light patterns may generally have different patterns from each other. The individual 3D multi-focal light patterns may be sequentially (i.e., one after another) projected into the target tissue, and the field of view of the spatial light modulator may be spatially translated between any two or more of the individual 3D multi-focal light patterns, e.g., using a mirror galvanometer. As the field of view of the spatial light modulator is shifted between individual 3D multi-focal light patterns, a different subset of excitable cells, e.g., neurons, may become accessible for illumination by an individual 3D multi-focal light pattern. Thus, the spatio-temporally multiplexed 3D multi-focal light patterns can collectively illuminate excitable cells in a volume of the target tissue that is not accessible with an individual 3D multi-focal light pattern (i.e., without translating the field of view of the spatial light modulator).

The sets of excitable cells that are illuminated by individual 3D multi-focal light patterns at each field of view of the spatial light modulator may be different from each other. In some cases, overlapping but different sets of excitable cells are illuminated by individual 3D multi-focal light patterns as the spatial light modulator is translated across the target tissue and an individual 3D multi-focal light pattern is projected into the tissue at each position. The degree of overlap may be any suitable degree of overlap, and in some cases, may be 90% or less, e.g., 80% or less, 70% or less, 60% or less, 50% or less, 40% or less, 30% or less, 20% or less, 10% or less, 5% or less, including 1% or less, between any two sets of excitable cells illuminated by two different individual 3D multi-focal light patterns. In some cases, the sets of excitable cells illuminated by individual 3D multi-focal light patterns as the spatial light modulator is translated across the target tissue are non-overlapping sets.

The number of cells in each set of excitable cells that are illuminated by individual 3D multi-focal light patterns at each field of view of the spatial light modulator may vary depending on individual 3D multi-focal light pattern used to illuminate each set of cells. In general, each set of excitable cells illuminated by individual 3D multi-focal light patterns is smaller than the total number of excitable cells selected for illumination and/or measurement of activity. Thus, in some cases, a set of excitable cells illuminated by an individual 3D multi-focal light pattern has on average 90% or fewer, e.g., 80% or fewer, 70% or fewer, 60% or fewer, 50% or fewer, 40% or fewer, 30% or fewer, 20% or fewer, including 10% or fewer number of cells than the total number of excitable cells selected for illumination and/or measurement of activity. In some embodiments, the set of excitable cells illuminated by an individual 3D multi-focal light pattern has on average from 5% to 10%, from 10% to 20%, from 30% to 40%, from 40% to 50%, form 50% to 60%, from 60% to 70%, from 70% to 80%, or from 80% to 90% fewer number of cells than the total number of excitable cells selected for illumination and/or measurement of activity.

In some embodiments, the subject method involves selecting a first subset of excitable cells, e.g., a first subset of neurons, in a target tissue for analysis, wherein the target tissue is in a field of view of a microscope and wherein the target tissue includes a plurality of excitable cells that are adapted to emit fluorescence sensitive to cellular electrical activity, e.g., neuronal activity, obtaining individual two-dimensional (2D) diffraction patterns for each excitable cell in the first subset of excitable cells by a) contacting an excitable cell in the first subset with a laser light, thereby causing the excitable cell to emit fluorescence, b) directing the emitted fluorescence from the contacted excitable cell through a microlens array to create a 2D diffraction pattern, and c) recording the 2D diffraction pattern, and iii) measuring the activity of individual excitable cells in the first subset by a) projecting one or more three-dimensional (3D) multi-focal laser light patterns into the target tissue, thereby causing at least a subset of excitable cells in the first subset of excitable cells in the target tissue to emit fluorescence, b) directing the fluorescence emitted from the target tissue in response to the one or more 3D multi-focal laser light patterns through the microlens array to generate a multiplexed 2D diffraction pattern, c) recording the multiplexed 2D diffraction pattern, and d) resolving the multiplexed 2D diffraction pattern using the individual 2D diffraction patterns of each individual excitable cell in the at least a subset of excitable cells in the first subset to determine the activity of each individual excitable cell illuminated by the one or more 3D multi-focal laser light patterns. Aspects of the methods are now further described in greater detail below.

In general terms, excitable cells, e.g., neurons, whose activity patterns are of interest are first selected within a target tissue. To allow selection of the neurons, the target tissue may be in the field of view of a microscope, such as the microscope of the system described above, and the target tissue may contain neurons that are adapted to emit fluorescence so that they may be identified, e.g., by scanning the tissue using conventional scanning two-photon fluorescence microscopy and recording the emitted fluorescence with a photodetector (e.g., a photomultiplier tube), to generate a stack of full-frame 2D images. The fluorescence emitted by the neuron includes fluorescence sensitive to neuronal activity, e.g., intensity, wavelength, etc., of fluorescence changes in response to changes in membrane potential or intracellular calcium concentration. Fluorescent neurons suitable for use in the present method are described in further detail below.

For each excitable cell, e.g., each neuron, of interest, the cell may be illuminated with a laser light appropriate to cause the excitable cell to emit fluorescent light and the fluorescent light originating from the excitable cell and diffracted by the microlens array is captured on an image detector as an individual 2D diffraction pattern, which can be used to obtain an empirical measure of the point spread function of the excitable cell. In certain embodiments, the laser light is one or more 3D single-focal laser light patterns generated by the spatial light modulator. In some embodiments, the laser light is a plurality of 3D single-focal laser light patterns, temporally scanned across the excitable cell to generate an individual 2D diffraction pattern.

The activity of individual excitable cells, e.g., individual neurons, is then measured collectively for multiple excitable cells of interest in the field of view of the image detector by illuminating the excitable cells, or different subsets of excitable cells, using one or more 3D multi-focal laser light patterns. Measuring the activity of an excitable cell may include measuring the change in the activity level of the excitable cell over a time period. Thus, in such instances, the time period may be divided into multiple time points (e.g., exposure times of the image detector) at which the activity of the excitable cell is measured according to the method described herein. Thus, the activity of individual excitable cells may be measured collectively at each time point (e.g., single exposure of the image detector) for multiple excitable cells of interest in the target tissue by illuminating all the excitable cells, or excitable cells in one or more different subsets thereof, using one or more 3D multi-focal laser light patterns.

The 3D multi-focal laser light patterns may be generated, e.g., by splitting a seed laser beam into multiple beamlets using a spatial light modulator (in other words, spatially modulating the amplitude and/or phase of the seed laser beam using the spatial light modulator), and projecting the beamlets (i.e., the spatially modulated laser beam) into the target tissue as 3D multi-focal laser light patterns, where the 3D multi-focal laser light patterns may be configured such that excitable cells, e.g., neurons, of interest are specifically targeted for illumination by the beamlets of the 3D multi-focal laser light patterns (i.e., by the spatially modulated laser beam). The illumination may be spatio-temporally multiplexed within each time point (e.g., single exposure of an image detector) of the measurement such that each pattern of a plurality of 3D multi-focal laser light patterns are projected sequentially into the sample at one or more fields of view of the spatial light modulator. Thus in some cases, multiple 3D multi-focal laser light patterns may be projected into the sample at the same field of view of the spatial light modulator by switching the phase mask of the spatial light modulator. In some cases, a single 3D multi-focal laser light pattern may projected into the sample at multiple distinct fields of view of the spatial light modulator by horizontally translating the spatial light modulator field of view using the mirror galvanometers. In some cases, multiple 3D multi-focal laser light patterns may be projected into the sample in at least two distinct fields of view of the spatial light modulator by switching the phase mask of the spatial light modulator and horizontally translating the spatial light modulator field of view using the mirror galvanometers.

In certain embodiments, an individual excitable cell, e.g., an individual neuron whose activity is selected to be measured, is illuminated by the beamlets forming one or more 3D multi-focal laser light patterns at each time point (e.g., a single exposure of the image detector of, e.g., 100 milliseconds (ms)). In such cases, a spatio-temporally multiplexed 3D multi-focal laser light pattern is projected into the target tissue for a time point, and some of the beamlets of the spatio-temporally multiplexed 3D multi-focal laser light pattern collectively illuminates a volume corresponding to the position of the individual excitable cell with a scanned diffraction limited spot. Thus, in some embodiments, the method includes projecting a spatio-temporally multiplexed 3D multi-focal laser light pattern into the target tissue to illuminate a set of excitable cells in each time point. In some embodiments, the method includes projecting a plurality of spatio-temporally multiplexed 3D multi-focal laser light patterns into the target tissue to illuminate a plurality of sets of excitable cells in each time point.

The rate at which multiple distinct 3D multi-focal laser light patterns are sequentially projected into the target tissue may vary, depending on the desired level of multiplexing and/or signal strength. In some cases, the spatio-temporally multiplexed 3D multi-focal light patterns are projected into the target tissue by projecting a plurality of individual 3D multi-focal light patterns sequentially into the target tissue at a rate of at most about 0.75 times, e.g., at most about 0.7 times, at most about 0.65 times, at most about 0.6 times, at most about 0.55 times, including at most about 0.5 times the maximum switching rate of the spatial light modulator. In some embodiments, the rate may be in the range of about 0.3 times to about 0.8 times, e.g., about 0.35 times to about 0.75 times, about 0.4 times to about 0.7 times, including about 0.4 times to about 0.6 times the maximum switching rate of the spatial light modulator. In some embodiments, the rate at which distinct spatio-temporally multiplexed 3D multi-focal laser light patterns are sequentially projected into the target tissue may vary, and the rate may be in the range of about 0.3 to about 0.8, e.g., about 0.4 to about 0.7, including about 0.4 to about 0.6 times the maximum switching rate of the spatial light modulator.

The wavelength of the laser light used to contact or illuminate the excitable cells may be any suitable wavelength, depending on the fluorescence excitation wavelength of the cells. In some cases the present method employs two-photon excitation. Thus, in some cases, the wavelength of the laser light is in the near-infrared range (e.g., about 700 nm to about 2500 nm, 800 nm to 1500 nm, including 850 nm to 1000 nm).

Figure 1B:
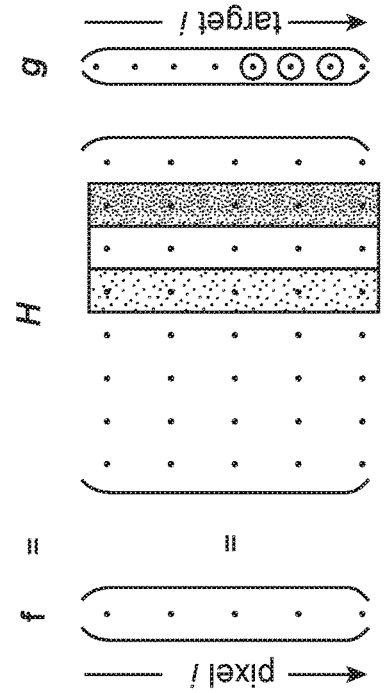
Figure 1C:
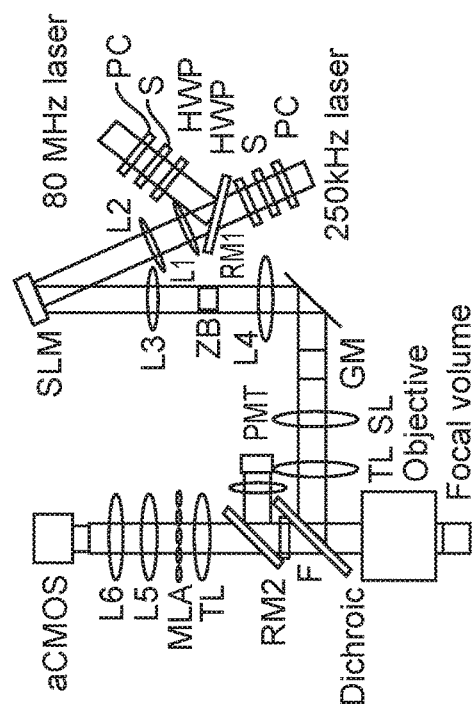
Figure 1D:
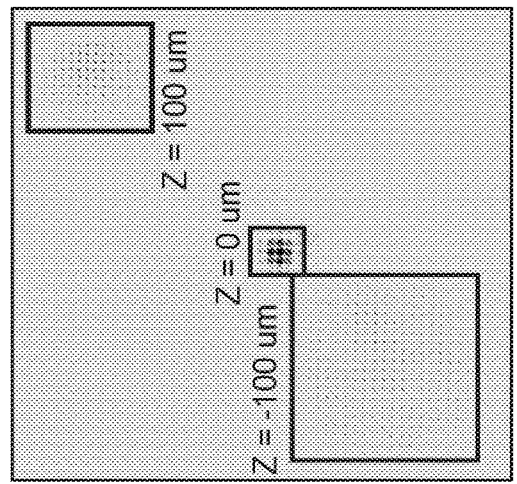

Fluorescence emitted by the excitable cells illuminated by the one or more 3D multi-focal laser light patterns is directed through the microlens array, thereby creating a diffracted fluorescence emission and the diffracted fluorescence emission is imaged by an image detector as a 2D diffraction pattern. The 2D diffraction pattern may be a multiplexed 2D diffraction pattern, containing an incoherent linear sum of the fluorescence emitted by multiple individual excitable cells in the target tissue upon illumination by the 3D multi-focal laser light pattern. The relationship between the observed multiplexed 2D diffraction pattern and the contribution of fluorescence from each individual excitable cell can be represented by the equation: $f=Hg$, where $f$ represents the observed fluorescence intensity at each pixel, $H$ is a measurement matrix constructed from the empirically-determined individual 2D diffraction patterns, and $g$ represents the contribution of fluorescence intensity from discrete volumes in the target tissue (FIG. 1D). Thus, the contribution of fluorescence emitted by each illuminated excitable cell to the multiplexed 2D diffraction pattern may be resolved by deconvolving the multiplexed 2D diffraction pattern using an optical model for light propagation through the emission path of the microscope, which, in some cases, may be the empirically-determined individual 2D diffraction patterns for each of the excitable cells. A suitable method is described in, e.g., Broxton et al., 2013, Optics Express 21(21), 25418, which is incorporated herein by reference. The optical model may be any suitable model for deconvolving the multiplexed 2D diffraction pattern, and in some cases, may be an analytical model, or an empirical model, such as that described above. In some cases, the analytical model is a wave optics model.

The target tissue may be any suitable excitable tissue for measuring the activity of one or more individual excitable cells therein. In some embodiments, the target tissue is a light-scattering target tissue. In some cases, light passing through the light-scattering target tissue may be diffracted differently depending on the path of passage. Thus, the light-scattering tissue may induce variable, non-homogeneous diffraction patterns depending on the location within the tissue volume from which light, e.g., fluorescence, originates. In some cases, the light-scattering target tissue has variable, non-homogeneous indices of refraction throughout the tissue volume. The target tissue may also absorb light passing through. Thus, the intensity of light may decrease as light passes through a scattering target tissue.

In some embodiments, the decrease in light intensity per unit thickness of tissue may be defined as a scatter coefficient, S, as described in Aravanis et al., J Neural Eng 2007 September; 4(3) S143-56, which is incorporated by reference. S may be estimated by the Kubelka-Munk model for diffuse scattering media: $T=1/(Sz+1)$, where T is the transmission fraction, and z is the thickness of the sample, assuming a planar, homogeneous, ideal diffuser illuminated from one side with diffuse monochromatic light, constant reflection and no absorption through the sample. The scatter coefficient, S, of the target tissue may vary, and may be in the range of about 5 mm$^{-1}$ to about 20 mm$^{-1}$, e.g., about 8 mm$^{-1}$ to about 15 mm$^{-1}$, including about 10 mm$^{-1}$ to 12 mm$^{-1}$.

In some embodiments, the target tissue, e.g., the light-scattering target tissue, can be imaged using the present system and method at a depth of up to about 500 μm, e.g., up to about 400 μm, up to about 350 μm, up to about 300 μm, including up to about 250 μm from the surface of the target tissue proximal to the objective.

The target tissue may be an in vivo neuronal tissue, a tissue slice preparation, a nerve fiber bundle, a neuromuscular junction, etc. The in vivo neuronal tissue may be neuronal tissue of an animal that is anesthetized or non-anesthetized, and is restrained or non-restrained, where the present system is configured so as to place the target tissue of interest in the field of view of the microscope. The target tissue of interest includes, but is not limited to, the neocortex, the hypothalamus, entorhinal and hippocampal formation cortex, mammillary bodies, septum, bed nucleus of stria terminalis, dorsal and ventral striatum, thalamus, amygdala, accumbens, brainstem, subcortical structures in general, muscle, spinal cord, cardiac tissue, etc.

In certain embodiments, the present method includes placing the target tissue in the field of view of the microscope of the present system, as described above. Placing the target tissue in the field of view of the microscope of the present system may be achieved by any suitable method known in the art. In some instances, when the target tissue is an in vivo neuronal tissue, the system may include an interface for implanting or fixing a device to the animal such that the target tissue is placed in the field of view of the microscope.

Any suitable part of an excitable cell may be used to illuminate and/or measure activity therein. Thus, a reference to a "cell" is intended to include a portion of the cell, such as the cell body, which may in general refer to the area of the cell that is at and surrounds the cell nucleus, or any cytoplasmic extension of the cell that is amenable to illumination and/or optical measurement by methods of the present disclosure. In some cases, two spatially distinct portions of a single cell (e.g., distinct neurites or distinct synaptic termini of a neuron) may be considered to be different "cells".

The number of excitable cells, e.g., neurons, illuminated by a single 3D multi-focal laser light pattern projected into the target tissue may be 10 or more excitable cells, e.g., 15 or more excitable cells, 20 or more excitable cells, 50 or more excitable cells, 80 or more excitable cells, including 100 or more excitable cells, and in some cases may be 1,000 or fewer excitable cells, e.g., 500 or fewer excitable cells, including 200 or fewer excitable cells. In some embodiments, the number of excitable cells, e.g., neurons, illuminated by a single 3D multi-focal laser light pattern projected into the target tissue may be in the range of 10 cells to 1,000 cells, e.g., 10 cells to 500 cells, 15 cells to about 500 cells, including 15 cells to 200 cells.

The number of excitable cells, e.g., neurons, whose activity-sensitive fluorescence is measured at each time point (e.g., collectively measured over each exposure of the image detector) may be 10 or more excitable cells, e.g., 15 or more excitable cells, 20 or more excitable cells, 50 or more excitable cells, 80 or more excitable cells, 100 or more excitable cells, 200 or more excitable cells and may be 5000 or fewer excitable cells, 1000 or fewer excitable cells, 500 or fewer excitable cells, including 200 or fewer excitable cells. In some embodiments, the number of excitable cells, e.g., neurons, whose activity-sensitive fluorescence is measured at each time point (e.g., collectively measured over each exposure of the image detector) may be in the range of 15 to 3000 excitable cells, e.g., 20 to 1000 excitable cells, 20 to 500 excitable cells, 50 to 300 excitable cells, including 100 to 250 excitable cells. In certain embodiments, the present method include selecting a subset of excitable cells in the target tissue and measuring the activity of all excitable cells in the subset at each time point by collectively illuminating each of the excitable cells with one or more 3D multi-focal laser light patterns.

In some embodiments, where multiple distinct 3D multi-focal laser light patterns are projected into the target tissue at each time point (e.g., each exposure of the image detector) of the measurement, the spatial light modulator phase mask for each 3D multi-focal laser light pattern is defined so that the one or more 3D multi-focal laser light patterns illuminate a subset of excitable cells whose individual 2D diffraction patterns are sufficiently different from one another so as to improve the precision and/or accuracy of resolving the multiplexed 2D diffraction pattern generated by the excitable cells. The difference between individual 2D diffraction patterns may be determined by any convenient method, e.g., Euclidian distance, percent similarity in pixels, etc. Thus, the excitable cells assigned to a subset of excitable cells that are illuminated by a spatio-temporally multiplexed 3D multi-focal laser light pattern may be chosen by setting a minimum threshold for differences between any two individual 2D diffraction patterns within the subset. In some instances, the excitable cells assigned to a subset of excitable cells that are illuminated by a spatio-temporally multiplexed 3D multi-focal laser light pattern may be chosen by maximizing the minimum difference between any two individual 2D diffraction patterns within the subset.

In certain embodiments, the present method includes calibrating the spatial light modulator coordinate system and the 3D two-photon imaging coordinate system using the 2D diffraction pattern of the fluorescence generated by the microlens array as the reference coordinate system. In certain embodiments, the calibrating includes placing a fluorescent sample volume in the field of view of the microscope, illuminating discrete spots within the volume to cause emission of fluorescence from each spot, directing the fluorescence through the microarray lens to generate a reference 2D diffraction pattern for each location, recording the reference 2D diffraction pattern on the image detector and reconstructing the location of the spots.

In certain embodiments, the laser beam that is used to seed the multiplexed 3D multi-focal laser light pattern is pulsed at a frequency of about 100 kHz or more, e.g., about 150 kHz or more, about 200 kHz or more, and in some cases, may be pulsed at a frequency of about 1 MHz or less, e.g., about 800 kHz or less, about 600 kHz, or less, about 500 kHz or less, including about 400 kHz or less. In certain embodiments, the laser beam that is used to seed the multiplexed 3D multi-focal laser light pattern is pulsed at a frequency in the range of about 100 kHz to about 1 MHz, e.g., about 100 kHz to about 700 kHz, about 100 kHz to about 500 kHz, about 150 kHz to about 350 kHz, including about 200 kHz to about 300 kHz.

In certain embodiments, the laser beam that is used to seed the multiplexed 3D multi-focal laser light pattern has an average power in the range of about 1.0 W to about 3.0 W, e.g., about 1.5 W to about 2.5 W, about 1.6 W to about 2.0 W, including about 1.7 W to about 1.9 W.

In certain embodiments, the laser beam that is used to seed the multiplexed 3D multi-focal laser light pattern has a pulse duration in the range of about 10 fs to about 1000 fs, e.g., about 50 fs to about 800 fs, about 80 fs to about 500 fs, about 100 fs to about 300 fs, including about 150 fs to about 250 fs.

In some embodiments, the spatio-temporal multiplexing of the illumination patterns on the spatial light modulator increases the two photon signal generation efficiency. In some embodiments, the spatio-temporal multiplexing of the illumination patterns on the spatial light modulator provides for a more uniform illumination of the field of view of the image detector within each time point (e.g., each exposure of the image detector) during measurement of neural activity.

The present methods and systems may provide for illuminating and/or measuring cellular electrical activity, e.g., neural activity, from cells in a volume that is larger than the maximum volume that can be illuminated or imaged using a stationary spatial light modulator at the same temporal resolution. In some cases, the volume of the target tissue that is illuminated and/or imaged by the present methods and systems has a horizontal dimension (i.e., width or length along a plane perpendicular to the axis of view of the microscope) of about 300 µm or more, e.g., about 350 µm or more, about 400 µm or more, about 450 µm or more, including about 500 µm or more. In some embodiments, the volume of the target tissue that is illuminated and/or imaged by the present methods and systems has a horizontal dimension in the range of about 300 µm to about 1,000 µm, e.g., about 350 µm to about 900 µm, about 400 µm to about 800 µm, including about 500 µm to about 700 µm. In some cases, the volume of the target tissue that is illuminated and/or imaged by the present methods and systems has a depth (i.e., along the axis of view of the microscope) of about 50 µm or more, e.g., about 75 µm or more, about 100 µm or more, about 150 µm or more, including about 200 µm or more. In some embodiments, the volume of the target tissue that is illuminated and/or imaged by the present methods and systems has a horizontal dimension in the range of about 50 µm to about 500 µm, e.g., about 75 µm to about 400 µm, about 100 µm to about 350 µm, including about 150 µm to about 300 µm.

In certain embodiments, horizontally translating the field of view of the spatial light modulator using the mirror galvanometers increases the volume in the target tissue that can be illuminated by the spatial light modulator and therefore increases the number of excitable cells, e.g., neurons, that can be collectively illuminated, e.g., illuminated within each time point (e.g., each exposure of the image detector) during measurement of neural activity, by the 3D multi-focal laser light patterns. In other words, the excitable cells which are illuminated by the spatio-temporally multiplexed 3D multi-focal laser light patterns collectively occupy a volume of the target tissue that is larger than the volume that can be illuminated with an individual 3D multi-focal light pattern (i.e., without spatially translating the field of view of the spatial light modulator). "Occupy" as used herein, may refer to at least the detectable presence of an excitable cell in a monolithic, contiguous volume (e.g., rectangular volume) of the target tissue. For measuring the activity of the excitable cell, the presence may be based on the portion of the cell body of the excitable cell in which the activity of the cell is to be measured (e.g., a rectangular volume of the target tissue in in which the cell body or a neurite of a neuron is present). Thus, a volume collectively occupied by a group of excitable cells (e.g., neurons) may not extend beyond a monolithic, contiguous volume (e.g., a rectangular volume) that includes the cell bodies or the neurites at which the excitable cells are illuminated, even if other portions of the excitable cells (e.g., neurites) may exist outside of the collectively occupied volume.

In some cases, the excitable cells illuminated by the spatio-temporally multiplexed 3D multi-focal laser light patterns occupy a volume of the target tissue that is at least about 1.5 times, e.g., at least about 2 times, at least about 3 times, at least about 5 times, at least about 8 times, at least about 9 times, and up to about 10 times larger than the volume that can be illuminated without horizontally translating the field of view of the spatial light modulator. In some embodiments, the excitable cells illuminated by the spatio-temporally multiplexed 3D multi-focal laser light patterns occupy a volume of the target tissue that is from about 1.5 times to about 20 times, e.g., from about 2 times to about 15 times, from about 5 times to about 12 times, including from about 8 times to about 10 times larger than the volume that can be illuminated without horizontally translating the field of view of the spatial light modulator.

In some embodiments, the 3D multi-focal laser light patterns illuminated into the sample by horizontally translating the field of view of the spatial light modulator collectively illuminate excitable cells in a volume of the target tissue that is at least about 1.5 times, e.g., at least about 2 times, at least about 3 times, at least about 5 times, at least about 8 times, at least about 9 times, and up to about 10 times larger than the volume that can be illuminated without horizontally translating the field of view of the spatial light modulator. In some embodiments, the 3D multi-focal laser light patterns illuminated into the sample by horizontally translating the field of view of the spatial light modulator collectively illuminate excitable cells in a volume of the target tissue that is in the range of about 1.5 times to about 20 times, e.g., about 2 times to about 15 times, about 5 times to about 12 times, including about 8 times to about 10 times larger than the volume that can be illuminated without horizontally translating the field of view of the spatial light modulator.

In certain embodiments, the present method may include measuring the activity of one or more individual excitable cells, e.g., one or more individual neurons, in a target tissue, as described above, and manipulating the target tissue or subject to which the target tissue belongs in response to the measured activity. The manipulation may include optical stimulation of light-responsive excitable cells, as described further below, or any other appropriate stimulation that produces a desired effect in response to the measured activity. In some embodiments, the method includes stimulating the target tissue and measuring the response, if any, of individual excitable cells to the stimulation. The stimulation may include, e.g., sensory stimulation of an animal when recording in vivo, electrical stimulation of different parts of the target tissue that may have direct or indirect functional connections to excitable cells in the field of view of the image detector or microscope, or optical stimulation of excitable cells in the field of view of the image detector or microscope where the excitable cells are adapted to hyperpolarize and/or depolarize in response to a laser light stimulus.

In any embodiment, the target tissue may include excitable cells, e.g., neurons, that are genetically modified to express a light-responsive polypeptide that hyperpolarizes or depolarizes the excitable cell in response to a laser light stimulus. The light-responsive polypeptide may include one or more various opsins that are known in the field, and are further described below.

Also provided herein is a method of illuminating a plurality of individual excitable cells, e.g., a plurality of individual neurons, in a target tissue, the method including i) selecting a first subset of excitable cells in a target tissue for analysis, wherein the target tissue is in a field of view of a microscope and wherein the target tissue contains a plurality of excitable cells that are adapted to emit fluorescence; and ii) sequentially projecting each 3D multi-focal laser light pattern of a plurality of 3D multi-focal laser light patterns generated by a spatial light modulator into the target tissue, wherein the plurality of 3D multi-focal laser light patterns is projected into at least two distinct sites in the target tissue, thereby collectively and specifically illuminating the plurality of excitable cells in the target tissue.

As described above, the plurality of 3D multi-focal laser light patterns may be one or more spatio-temporally multiplexed 3D multi-focal laser light patterns generated by switching the phase mask of the spatial light modulator and/or horizontally translating the field of view of the spatial light modulator using mirror galvanometers.

In certain embodiments, the excitable cells of the target tissue may contain a fluorescent dye or express a fluorescent protein. In certain embodiments, the fluorescent dye or fluorescent protein emit fluorescence in a cellular electrical activity-dependent manner, e.g., a neuronal activity-dependent manner, to enable measurement of cellular electrical activity, as described above.

The present disclosure also includes a method of measuring the activity of one or more individual excitable cells, e.g., one or more individual neurons, in a target tissue, as described above, and modulating the activity of a plurality of excitable cells in the target tissue in response to the measured activity of the plurality of activity-sensitive fluorescence-emitting excitable cells. The modulating may be done by any convenient method of activating or inhibiting the plurality of excitable cells in the target tissue, including, but not limited to, sensory stimulation of the host organism to which the target tissue belongs, electric stimulation of excitable cells that are functionally (directly or indirectly) connected to the measured excitable cells, or photostimulation of excitable cells in the field of view of the microscope and that are functionally (directly or indirectly) connected to the measured excitable cells where the photostimulated excitable cells are adapted to hyperpolarizes or depolarizes in response to a laser light stimulus. In some embodiments, optically stimulating the genetically modified excitable cells may include contacting the excitable cells adapted to respond to light and functionally connected to the measured excitable cells using one or more 3D multi-focal laser light pattern stimuli, wherein the one or more 3D multi-focal laser light pattern stimuli are controlled in response to the measured activity of the measured excitable cells. The one or more 3D multi-focal laser light pattern stimuli may be projected into the target tissue using the spatial light modulator and/or mirror galvanometers, as described above.

The one or more 3D multi-focal laser light pattern stimuli may be selected to specifically hyperpolarize or depolarize a set of excitable cells, e.g., a set of neurons, depending on the desired outcome. For example, if the measured activity of one or more excitable cells is higher than desired, the one or more 3D multi-focal laser light pattern stimuli may be configured to stimulate excitable cells in the field of view of the microscope to reduce activity of the one or more excitable cells by, e.g., stimulating a hyperpolarizing light-responsive polypeptide expressed in the one or more excitable cells, by stimulating a hyperpolarizing light-responsive polypeptide expressed in excitable cells that (directly or indirectly) functionally activate the one or more excitable cells, or by stimulating a depolarizing light-responsive polypeptide expressed in excitable cells that (directly or indirectly) functionally inhibit the one or more excitable cells. In some embodiments, the method includes computationally compensating for the effect of any optical cross-talk between the 3D multi-focal laser light pattern stimuli and the fluorescence measurement for neural activity.

In certain embodiments, the present system and method achieves high-speed, high-signal measurement and/or control of neuronal activity in a target tissue. Thus, in some embodiments, the method includes controlling the mirror galvanometers to project multiple 3D multi-focal laser light patterns generated by the spatial light modulator into the sample across multiple spatially distinct fields of view of the spatial light modulator. The maximum rate at which a sequence of 3D multi-focal laser light patterns is projected into the sample across multiple spatially distinct fields of view of the spatial light modulator may vary depending on the maximum switching speed of the spatial light modulator and the desired signal rate, as described above.

The rate at which neuronal activity is collectively measured by the present systems and methods may be in the range of about 1 Hz to about 200 Hz, e.g., about 5 Hz to about 150 Hz, including about 10 Hz to about 100 Hz. The rate at which neuronal activity is collectively measured by the present systems and methods may be 1 Hz or more, e.g., about 5 Hz or more, about 10 Hz or more, about 20 Hz or more, about 30 Hz or more, including about 40 Hz or more, and in some cases, may be about 200 Hz or less, about 150 Hz or less, including about 100 Hz or less. The rate at which neuronal activity is collectively measured by the present systems and methods, when using a spatio-temporally multiplexed 3D multi-focal light pattern, may be in the range of about 1 Hz to about 80 Hz, e.g., about 5 Hz to about 70 Hz, including about 10 Hz to about 50 Hz. In some embodiments, the rate at which neuronal activity is collectively measured by the present systems and methods, when using a spatio-temporally multiplexed 3D multi-focal light pattern, may be about 1 Hz or more, e.g., about 5 Hz or more, about 10 Hz or more, about 20 Hz or more, about 30 Hz or more, including about 40 Hz or more, and in some cases, may be about 80 Hz or less, about 70 Hz or less, including about 60 Hz or less. The rate at which neuronal activity is collectively measured by the present systems and methods, when using a 3D multi-focal light pattern that is not spatio-temporally multiplexed, may be in the range of about 50 Hz to about 150 Hz, e.g., about 70 Hz to about 130 Hz, including about 80 Hz to about 120 Hz. In some embodiments, the rate at which neuronal activity is collectively measured by the present systems and methods, when using a 3D multi-focal light pattern that is not spatio-temporally multiplexed, may be about 50 Hz or more, e.g., about 70 Hz or more, about 80 Hz or more, 90 Hz or more, about 100 Hz or more, and in some cases, may be about 200 Hz or less, about 150 Hz or less, including about 120 Hz or less.

The rate at which neuronal activity is collectively measured and stimulated by the present systems and methods may be in the range of about 1 Hz to about 200 Hz, e.g., about 5 Hz to about 150 Hz, including about 10 Hz to about 100 Hz. The rate at which neuronal activity is collectively measured and stimulated by the present systems and methods may be about 1 Hz or more, e.g., about 5 Hz or more, about 10 Hz or more, about 20 Hz or more, about 30 Hz or more, including about 40 Hz or more, and in some cases, may be about 200 Hz or less, about 150 Hz or less, including about 100 Hz or less. The rate at which neuronal activity is collectively measured and stimulated by the present systems and methods, when using a spatio-temporally multiplexed 3D multi-focal light pattern, may be in the range of about 1 Hz to about 80 Hz, e.g., about 5 Hz to about 70 Hz, including about 10 Hz to about 50 Hz. In some embodiments, the rate at which neuronal activity is collectively measured and stimulated by the present systems and methods, when using a spatio-temporally multiplexed 3D multi-focal light pattern, may be about 1 Hz or more, e.g., about 5 Hz or more, about 10 Hz or more, about 20 Hz or more, about 30 Hz or more, including about 40 Hz or more, and in some cases, may be about 80 Hz or less, about 70 Hz or less, including about 60 Hz or less. The rate at which neuronal activity is collectively measured and stimulated by the present systems and methods, when using a 3D multi-focal light pattern that is not spatio-temporally multiplexed may be in the range of about 50 Hz to about 150 Hz, e.g., about 70 Hz to about 130 Hz, including about 80 Hz to about 120 Hz. In some embodiments, the rate at which neuronal activity is collectively measured and stimulated by the present systems and methods when using a 3D multi-focal light pattern that is not spatio-temporally multiplexed may be about 50 Hz or more, e.g., about 70 Hz or more, about 80 Hz or more, about 90 Hz or more, about 100 Hz or more, and may be about 200 Hz or less, about 150 Hz or less, including about 120 Hz or less.

Also provided herein is a computer-implemented method of analyzing individual 2D diffraction patterns of plurality of excitable cells, e.g., plurality of neurons, and multiplexed 2D diffraction patterns, recorded according to the method described herein, to measure the activity of individual excitable cells, e.g. individual neurons. The computer-implemented method may include resolving the multiplexed 2D diffraction pattern based on the individual 2D diffraction patterns, as described herein. In some embodiments, the present computer-implemented method includes calculating the statistical significance of various parameters, e.g., statistical significance of the measured change in activity level of an excitable cell, statistical significance of the difference in the ensemble of excitable cells activated or inhibited by a manipulation, e.g., therapeutic manipulation, compared to an appropriate control condition, etc. In some embodiments, the present computer-implemented method includes compressing data and/or reducing the dimensionality of the data to facilitate analysis.

Additional Embodiments

Additional embodiments of systems and methods of the present disclosure are now described.

Extending the SLM Field of View with Conjugated Scanning Mirrors

In a coherent illumination system, a desired object space intensity distribution, $I(x,y)=|F\{H(u,v)\}|^2$ can be attained by controlling the complex electric field at the pupil plane, where $$H(u,v)=A(u,v)e^{i\phi(u,v)} \quad (1)$$

In holographic illumination systems with phase-only modulation, $A(u,v)$ is the fixed laser amplitude, typically uniform or Gaussian.

For a phase-only SLM with 0-2π modulation at wavelength λ at each of the N×N pixels, the $\phi(u,v)=\phi_{SLM}(u,v)$ for a given desired 2D or 3D intensity pattern can be computed. However, the area over which light can be steered, termed field of view (FOV) by, may be constrained by the pixel count of the SLM to $2x_{max} \times 2y_{max}$ where $$x_{max} = y_{max} = \frac{\lambda}{4NA}N, \quad (2)$$

and N is the numerical aperture of the objective lens. The image of the SLM is assumed to be optically magnified such that the width of the SLM matches the diameter of the objective pupil (to jointly maximize spatial resolution and light transmission).

Figure 6A:
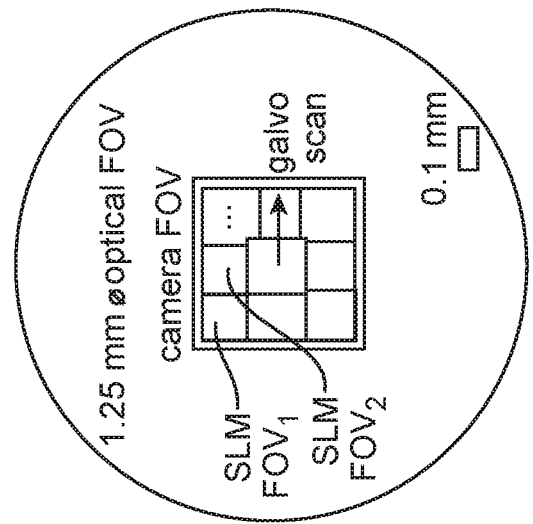
FIGS. 6A-6B are a collection of schematic diagrams showing a time-division multiplexing strategy for laterally extending the SLM field of view (FOV), according to embodiments of the present disclosure.

Often, the objective field of view is larger than the SLM-accessible field of view, as illustrated in FIGS. 5A and 6A. To address this, a pair of galvanometer scanning mirrors, conjugated to the SLM plane, may be used to apply a lateral shift of (Δx, Δy) by superimposing an additional linear phase term, $$\phi_{galvos}(u,v;\Delta x,\Delta y)=c(u\Delta x+v\Delta y), \quad (3)$$

where c depends on the wavelength and lens parameters. The total phase modulation is the sum of the two, $$\phi(u,v)=\phi_{SLM}(u,v)\pm\phi_{galvos}(u,v;\Delta x,\Delta y). \quad (4)$$

Figure 6B:
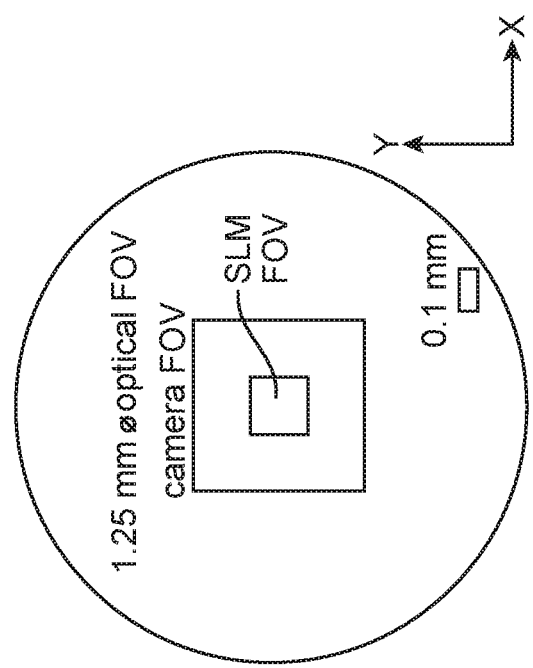

Rather than use the mirrors to enable smoother, continuous translation of a single hologram defining multiple optical traps, the time-sequential repositioning of the galvanometer mirrors and multiple different holograms may be used to achieve a larger effective FOV as shown in FIGS. 5B and 6B.

Figure 7B:
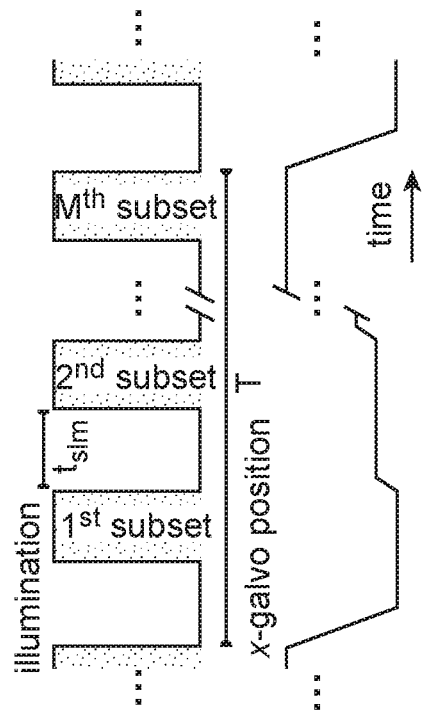
FIGS. 7A-7B are a collection of schematic diagrams and graphs showing timing considerations for SLM time-division multiplexing, according to embodiments of the present disclosure.
Figure 7A:
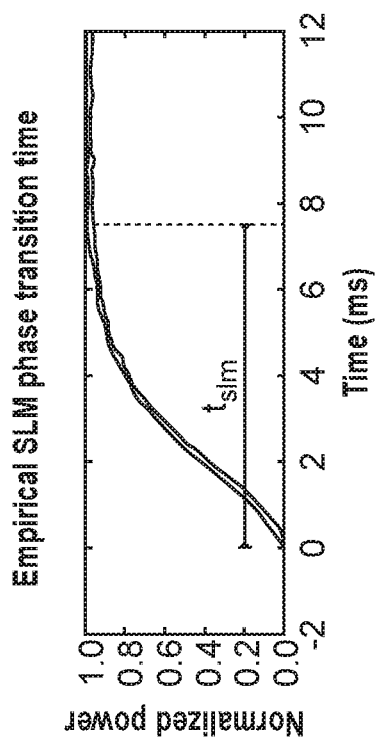

In a typical multiphoton microscope, the galvo positioning time is less than ~1 ms, so the area within the objective field of view tiled by the present approach in a given exposure time is determined by the SLM transition time, illustrated in FIGS. 7A and 7B.

FIGS. 7A and 7B: Timing considerations for SLM time-division multiplexing. (FIG. 7A) This particular SLM had an empirically measured 0 to ~97% transition time of 7.5 ms. (FIG. 7B) Timing diagram indicating SLM state throughout a given exposure time, T, for M sequentially illuminated subsets of focal spots. Each subset is laterally repositioned by galvanometer mirrors (y-galvo not shown).

Increasing Two-Photon Signal with Sequential Illumination

In two-photon excitation, signal rate depends quadratically on the average laser power P so the time-averaged signal integrated over a total period of exposure T is $$S \propto P^2 T. \quad (5)$$

For an illumination pattern that divides the average laser power equally to n excitation sites with equal focal volumes, the total time-averaged signal from the n volumes is $$S_{M=1} \propto n\left(\frac{P}{n}\right)^2 T, \quad (6)$$

which is a factor n times smaller than that in Eq. (5).

However, if the requirement for simultaneity of the illumination is relaxed, and M sets of n/M sites are allowed to be sequentially excited over the duration of the exposure time T, the total time-averaged signal may be $$S(M) \propto n\left(\frac{PM}{n}\right)^2 \left(\frac{T}{M} - t_{SLM}\right), \quad (7)$$

where $t_{SLM}$ is the time it takes the SLM to change the illumination pattern between each set of spots. This is greater than that in Eq. (6) by a factor of $$Z(M; t_{SLM}) = M\left(1 - M\frac{t_{SLM}}{T}\right). \qquad (8)$$

For a given $t_{SLM}$, Eq. (8) takes a maximum value of $M/2$ when $M=T/(2t_{SLM})$. Hence if the laser power is held fixed and the SLM transition time $t_{SLM}$ is known, the optimum number of subsets to scan may be determined in order to maximize the total two-photon excited signal for a given total experimental exposure time.

Excitable Cells

The present disclosure also provides excitable cells, e.g., neurons, that are adapted to emit fluorescence and excitable cells, e.g., neurons, that are adapted to hyperpolarize and/or depolarize in response to a laser light stimulus, suitable for use in the present method and system.

In some embodiments, the excitable cells, e.g., neurons, are associated with a fluorescent moiety, e.g., a fluorescent dye or a fluorescent protein, that enables the excitable cells to emit fluorescence in response to illumination with an appropriate stimulus (e.g., appropriate wavelength and intensity of illumination). In some embodiments, the excitable cells, e.g., neurons, comprise a fluorescent moiety, e.g., a fluorescent dye or a fluorescent protein, that enables the excitable cells to emit fluorescence in response to illumination with an appropriate stimulus (e.g., appropriate wavelength and intensity of illumination). An excitable cell may be associated with the fluorescent moiety by any suitable method, including being labeled directly or indirectly with a fluorescent dye or fluorescent protein, or expressing a genetically encoded fluorescent protein. Any suitable method may be used to indirectly label an excitable cell with a fluorescent moiety. In some cases, a binding member, e.g., an antibody, that specifically binds to a cell surface marker on the excitable cell may be conjugated with a fluorescent dye or protein, and the fluorescently conjugated binding member may be used to label the excitable cell indirectly.

The fluorescence emitted from excitable cells, e.g., neurons, that are adapted to emit fluorescence may be generally insensitive to cellular electrical activity, e.g., neuronal activity, of the excitable cell that emits the fluorescence. In such cases, fluorescent dyes of interest include fluorescein, fluorescein isothiocyanate (FITC), rhodamine, tetramethylenerhodamine isothiocyanate (TRITC), sulforhodamine 101 acid chloride (Texas Red®), phycoerythrin (PE), allophycocyanin, phycoerythrin-Texas Red® (PETR), 4-methylumbelliferone, etc. Fluorescent proteins of interest include green fluorescent protein, yellow fluorescent protein, cyan fluorescent protein, etc., and variants thereof.

The fluorescence emitted from excitable cells, e.g., neurons, that are adapted to emit fluorescence may be sensitive to cellular electrical activity, e.g., neuronal activity, of the excitable cell that emits the fluorescence. Fluorescent moieties whose fluorescence properties are sensitive to cellular electrical activity include ratiometric/non-ratiometric dyes and fluorescent proteins. Fluorescent moieties whose fluorescence properties are sensitive to cellular electrical activity may be a fluorescence resonance energy transfer (FRET)-based reporter. Fluorescent moieties whose fluorescence properties are sensitive to cellular electrical activity may be sensitive to changes in intracellular concentration of ions such as calcium, sodium and protons or to changes in membrane potential. In such cases, fluorescent dyes of interest include, but are not limited to, calcium indicator dyes (Indo-1, Fura-2, and Fluo-3, Calcium Green®, Fluo-4, etc.); sodium indicator dyes (sodium-binding benzofuran isophthalate (SBFI), Sodium Green™, CoroNa™ Green, CoroNa™ Red, etc.); and proton indicator dyes (2',7'-bis-(carboxyethyl)-5-(and-6)-carboxyfluorescein (BCECF), etc.). Cellular electrical activity-sensitive fluorescent proteins of interest include, but are not limited to, calcium indicators (Cameleon, GCaMP1, GCaMP2, GCaMP3, GCaMP6 and derivatives thereof, as well as those cited in U.S. Pat. No. 8,629,256, and Tian et al. 2012 Prog Brain Res, 196:79, which are incorporated herein by reference); and voltage indicators (QuasAr1, QuasAr2, VSFP, and derivatives thereof, as well as those cited in US App. Pub. No. 20130224756, Hochbaum et al., Nat Methods 2014 11:825, Baker et al. Brain Cell Biol 2008 36:53; and Mutoh et al., Exp Physiol 2011 96:13, which are incorporated herein by reference). In some cases, the fluorescent moiety may be sensitive to biochemical changes in the excitable cell, such as changes in enzymatic activity (e.g., activation of kinases); changes in binding interactions (e.g., binding of transcription factors to DNA); changes in subcellular localization of proteins; etc. Exemplary fluorescent moieties are further described in, e.g, Mehta et al., Annu Rev Biochem. 2011; 80: 375, which is incorporated herein by reference.

In some embodiments, the excitable cells, e.g., neurons, are adapted to hyperpolarize and/or depolarize in response to a laser light stimulus. In some embodiments, the tissue surrounding the excitable cells may contain a photo-sensitive caged compound, e.g., a caged neurotransmitter, that, when uncaged by a light stimulus, binds to a receptor on a excitable cell nearby and contributes to hyperpolarizing or depolarizing the excitable cell, depending on the neurotransmitter and the receptor. In some cases, the caged neurotransmitter may be glutamate, dopamine, serotonin, GABA, etc., available from, e.g., Tocris, as well as those caged neurotransmitters described in, e.g., U.S. Pat. No. 8,178,496, which is incorporated herein by reference. Suitable methods of using caged neurotransmitters to stimulate neurons is described in, e.g., Noguchi et al., J Physiol. 2011, 589:2447, which is incorporated herein by reference.

In some embodiments, the excitable cells (e.g., neurons) are genetically modified to express a light-responsive polypeptide that, when stimulated by an appropriate light stimulus, hyperpolarizes or depolarizes the stimulated excitable cell. In some instances, the light-responsive polypeptide is a light-activated ion channel polypeptide. The light-activated ion channel polypeptides are adapted to allow one or more ions to pass through the plasma membrane of a target cell when the polypeptide is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. In some embodiments, the light-responsive polypeptide depolarizes the excitable cell when activated by light of an activating wavelength. In some embodiments, the light-responsive polypeptide hyperpolarizes the excitable cell when activated by light of an activating wavelength.

In some embodiments, the light-responsive polypeptides are activated by blue light. In some embodiments, the light-responsive polypeptides are activated by green light. In some embodiments, the light-responsive polypeptides are activated by yellow light. In some embodiments, the light-responsive polypeptides are activated by orange light. In some embodiments, the light-responsive polypeptides are activated by red light.

In some embodiments, the light-responsive polypeptide expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive polypeptide. In some cases, the one or more amino acid sequence motifs which enhance light-responsive polypeptide transport to the plasma membranes of mammalian cells is fused internally within a light-responsive polypeptide. Optionally, the light-responsive polypeptide and the one or more amino acid sequence motifs may be separated by a linker. In some embodiments, the light-responsive polypeptide can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In some embodiments, the signal peptide sequence in the protein can be deleted or substituted with a signal peptide sequence from a different protein.

Exemplary light-responsive polypeptides and amino acid sequence motifs that find use in the present system and method are disclosed in, e.g., PCT App. Nos. PCT/US2011/028893 and PCT/US2015/23087. Representative light-responsive polypeptides that find use in the present disclosure are further described below.

In some embodiments, a depolarizing light-responsive polypeptide is a channelrhodopsin (ChR1—NCBI Gene ID: 5724518, ChR2—NCBI Gene ID: 5727376) derived from *Chlamydomonas reinhardtii*, wherein the polypeptide is capable of transporting cations across a cell membrane when the cell is illuminated with light. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization of the excitable cells, e.g., neurons, expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can comprise one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane.

In other embodiments, the light-responsive polypeptide is a step function opsin (SFO) protein or a stabilized step function opsin (SSFO) protein that can have specific amino acid substitutions at key positions in the retinal binding pocket of the amino acid sequence of ChR2. Further disclosure related to SFO or SSFO proteins can be found in International Patent Application Publication No. WO 2010/056970, the disclosure of which is hereby incorporated by reference in its entirety.

In some embodiments, a suitable light-responsive polypeptide is a cation channel derived from Volvox carteri (VChR1—NCBI Gene ID: 9619570) and is activated by illumination with light of a wavelength of from about 500 nm to about 600 nm, e.g., from about 525 nm to about 550 nm, e.g., 545 nm. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can comprise one or more conservative amino acid substitutions and/or one or more non-conservative amino acid substitutions. The light-responsive ion channel protein containing substitutions, deletions, and/or insertions introduced into the native amino acid sequence suitably retains the ability to transport ions across the plasma membrane of a excitable cell in response to light.

In other embodiments, the light-responsive polypeptide is a SFO or an SSFO based on VChR1. In some embodiments an SFO or SSFO protein is capable of mediating a depolarizing current in the cell when the cell is illuminated with blue light. In some embodiments, the light has a wavelength of about 560 nm. Additionally, in some embodiments the light is delivered as a single pulse of light or as spaced pulses of light due to the prolonged stability of SFO and SSFO photocurrents. In some embodiments, activation of the SFO or SSFO protein with single pulses or spaced pulses of light can cause depolarization of an excitable cell, e.g., neuron, expressing the SFO or SSFO protein. In some embodiments, each of the disclosed step function opsin and stabilized step function opsin proteins can have specific properties and characteristics for use in depolarizing the membrane of an excitable cell in response to light.

In other embodiments, the light-responsive cation channel protein is a C1V1 chimeric protein derived from the VChR1 protein of Volvox carteri and the ChR1 protein from *Chlamydomonas* reinhardti, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein further comprises a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein further comprises a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1.

In some embodiments, the C1V1 protein mediates a depolarizing current in the cell when the cell is illuminated with green light. In some embodiments, the light has a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, suitable light-responsive proteins include C1V1 chimeric light-responsive proteins that can have specific amino acid substitutions at key positions throughout the retinal binding pocket of the VChR1 portion of the chimeric polypeptide.

In other embodiments, the light-responsive cation channel protein is a C1C2 chimeric protein derived from the ChR1 and the ChR2 proteins from *Chlamydomonas reinhardtii*, wherein the protein is responsive to light and is capable of mediating a depolarizing current in the cell when the cell is illuminated with light. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein comprises one or more conservative amino acid substitutions and/or one or more non-conservative amino acid substitutions. The light-responsive proton pump protein containing substitutions, deletions, and/or insertions introduced into the native amino acid sequence suitably retains the ability to transport cations across a cell membrane.

In some aspects, a depolarizing light-responsive polypeptide is a red shifted variant of a depolarizing light-responsive polypeptide derived from *Chlamydomonas reinhardtii*; such light-responsive polypeptides are referred to herein as a "ReaChR polypeptide" or "ReaChR protein" or "ReaChR." The light used to activate the ReaChR polypeptide can have a wavelength between about 590 and about 630 nm or can have a wavelength of about 610 nm. The ReaChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the ReaChR protein can comprise one or more conservative amino acid substitutions and/or one or more non-conservative amino acid substitutions. The ReaChR containing substitutions, deletions, and/or insertions introduced into the native amino acid sequence suitably retains the ability to transport cations across a cell membrane.

In some aspects, a depolarizing light-responsive polypeptide is a SdChR polypeptide (Genbank Accession No.: AHH02138) derived from *Scherffelia dubia*, wherein the SdChR polypeptide is capable of transporting cations across a cell membrane when the cell is illuminated with light. The light used to activate the SdChR polypeptide can have a wavelength between about 440 and about 490 nm or can have a wavelength of about 460 nm. The SdChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the SdChR protein to regulate the polarization state of the plasma membrane of the cell. In some instances, the SdChR protein comprises one or more conservative amino acid substitutions and/or one or more non-conservative amino acid substitutions. The SdChR protein containing substitutions, deletions, and/or insertions introduced into the native amino acid sequence suitably retains the ability to transport cations across a cell membrane.

In some aspects, a depolarizing light-responsive polypeptide can be, e.g. CnChR2 (Genbank Accession No.: AHH02139), derived from *Chlamydomonas noctigama*, wherein the CnChR1 polypeptide is capable of transporting cations across a cell membrane when the cell is illuminated with light. The light used to activate the CnChR1 polypeptide can have a wavelength between about 560 and about 630 nm or can have a wavelength of about 600 nm. The CnChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the CnChR1 protein to regulate the polarization state of the plasma membrane of the cell. In some cases, the CnChR1 protein comprises one or more conservative amino acid substitutions and/or one or more non-conservative amino acid substitutions. The CnChR1 protein containing substitutions, deletions, and/or insertions introduced into the native amino acid sequence suitably retains the ability to transport cations across a cell membrane.

In other embodiments, the light-responsive cation channel protein is a CsChrimson chimeric protein derived from a CsChR (Genbank Accession No.: AHH02144) protein of *Chloromonas subdivisa* and CnChR1 protein from *Chlamydomonas noctigama*, wherein the N terminus of the protein comprises the amino acid sequence of residues 1-73 of CsChR followed by residues 79-350 of the amino acid sequence of CnChR1; is responsive to light; and is capable of mediating a depolarizing current in the cell when the cell is illuminated with light. The CsChrimson protein can additionally comprise substitutions, deletions, and/or insertions introduced into a native amino acid sequence to increase or decrease sensitivity to light, increase or decrease sensitivity to particular wavelengths of light, and/or increase or decrease the ability of the CsChrimson protein to regulate the polarization state of the plasma membrane of the cell. Additionally, the CsChrimson protein can comprise one or more conservative amino acid substitutions and/or one or more non-conservative amino acid substitutions. A CsChrimson protein containing substitutions, deletions, and/or insertions introduced into the native amino acid sequence suitably retains the ability to transport cations across a cell membrane.

In some aspects, a depolarizing light-responsive polypeptide can be, e.g. ShChR1 (Genbank Accession No.: AHH02106), derived from *Stigeoclonium helveticum*, wherein the ShChR1 polypeptide is capable of transporting cations across a cell membrane when the cell is illuminated with light. The light used to activate the ShChR1 protein derived from *Stigeoclonium helveticum* can have a wavelength between about 480 and about 510 nm or can have a wavelength of about 500 nm. The ShChR1 protein can additionally comprise substitutions, deletions, and/or insertions introduced into a native amino acid sequence to increase or decrease sensitivity to light, increase or decrease sensitivity to particular wavelengths of light, and/or increase or decrease the ability of the ShChR1 protein to regulate the polarization state of the plasma membrane of the cell. Additionally, the ShChR1 protein can comprise one or more conservative amino acid substitutions and/or one or more non-conservative amino acid substitutions. A ShChR1 protein containing substitutions, deletions, and/or insertions introduced into the native amino acid sequence suitably retains the ability to transport cations across a cell membrane.

In some embodiments, a suitable hyperpolarizing light-responsive polypeptide is an Archaerhodopsin (Arch-Genbank Accession No.: ADB03111) proton pump (e.g., a proton pump derived from *Halorubrum sodomense*) that can transport one or more protons across the plasma membrane of a cell when the cell is illuminated with light. The Arch protein can additionally have substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can comprise one or more conservative amino acid substitutions and/or one or more non-conservative amino acid substitutions. An Arch protein containing substitutions, deletions, and/or insertions introduced into the native amino acid sequence suitably retains the ability to transport ions across the plasma membrane of a target cell in response to light.

In some embodiments, a suitable light-activated protein is an Archaerhodopsin (ArchT-Genbank Accession No.: ABT17417) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can comprise one or more conservative amino acid substitutions and/or one or more non-conservative amino acid substitutions. The ArchT protein containing substitutions, deletions, and/or insertions introduced into the native amino acid sequence suitably retains the ability to transport ions across the plasma membrane of a target cell in response to light.

In some embodiments, the light-responsive polypeptide is responsive to blue light and is a proton pump protein derived from *Guillardia theta*, wherein the proton pump protein is capable of mediating a hyperpolarizing current in the cell when the cell is illuminated with blue light; such a protein is referred to herein as a "GtR3 protein" or a "GtR3 polypeptide". The GtR3 (NCBI Gene ID: 17301498) protein can additionally comprise substitutions, deletions, and/or insertions introduced into a native amino acid sequence to increase or decrease sensitivity to light, increase or decrease sensitivity to particular wavelengths of light, and/or increase or decrease the ability of the GtR3 protein to regulate the polarization state of the plasma membrane of the cell. Additionally, the GtR3 protein can comprise one or more conservative amino acid substitutions and/or one or more non-conservative amino acid substitutions. The GtR3 protein containing substitutions, deletions, and/or insertions introduced into the native amino acid sequence suitably retains the ability to hyperpolarize the plasma membrane of an excitable cell, e.g., neuron, in response to light.

In some embodiments, a light-activated protein is an *Oxyrrhis marina* (Oxy—Genbank Accession No.: ADY17806) proton pump that can transport one or more protons across the plasma membrane of a cell when the cell is illuminated with light. The light can have a wavelength between about 500 and about 560 nm or can have a wavelength of about 530 nm. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can comprise one or more conservative amino acid substitutions and/or one or more non-conservative amino acid substitutions. The Oxy protein containing substitutions, deletions, and/or insertions introduced into the native amino acid sequence suitably retains the ability to transport ions across the plasma membrane of a target cell in response to light.

In some embodiments, the light-responsive proton pump protein (referred to herein as "Mac protein"—NCBI Gene ID: 13287905) is responsive to light and is derived from *Leptosphaeria maculans*, wherein the Mac proton pump protein is capable of pumping protons across the membrane of a cell when the cell is illuminated with 520 nm to 560 nm light. The Mac protein can additionally comprise substitutions, deletions, and/or insertions introduced into a native amino acid sequence to increase or decrease sensitivity to light, increase or decrease sensitivity to particular wavelengths of light, and/or increase or decrease the ability of the Mac protein to regulate the polarization state of the plasma membrane of the cell. Additionally, the Mac protein can comprise one or more conservative amino acid substitutions and/or one or more non-conservative amino acid substitutions. A Mac protein containing substitutions, deletions, and/or insertions introduced into the native amino acid sequence suitably retains the ability to pump protons across the plasma membrane of an excitable cell, e.g., neuron, in response to light.

In some cases, a suitable light-responsive chloride pump protein is derived from *Natronomonas pharaonis*; such a protein is referred to herein as an "NpHR protein" or an "NpHR polypeptide." In some embodiments, the NpHR (NCBI Gene ID: 3702828) protein can be responsive to amber light as well as red light and can mediate a hyperpolarizing current in the excitable cell, e.g., the neuron, when the NpHR protein is illuminated with amber or red light. The wavelength of light that can activate the NpHR protein can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the NpHR protein can hyperpolarize a neural membrane for at least about 90 minutes when exposed to a continuous pulse of light. Additionally, the NpHR protein can comprise substitutions, deletions, and/or insertions introduced into a native amino acid sequence to increase or decrease sensitivity to light, increase or decrease sensitivity to particular wavelengths of light, and/or increase or decrease the ability of the NpHR protein to regulate the polarization state of the plasma membrane of the cell. In some embodiments, the NpHR protein comprises one or more conservative amino acid substitutions. In some embodiments, the NpHR protein comprises one or more non-conservative amino acid substitutions. An NpHR protein containing substitutions, deletions, and/or insertions introduced into the native amino acid sequence suitably retains the ability to hyperpolarize the plasma membrane of an excitable cell in response to light.

Further disclosure related to light-responsive chloride pump proteins can be found in U.S. Patent Application Publication Nos: 2009/0093403 and 2010/0145418 as well as in International Patent Application NO: PCT/US2011/028893, the disclosures of each of which are hereby incorporated by reference in their entireties.

In some embodiments, a suitable light-responsive ion channel protein is, e.g., a DsChR protein (Genbank Accession No.: AEY68833) derived from *Dunaliella salina*, wherein the ion channel protein is capable of mediating a hyperpolarizing current in the cell when the cell is illuminated with light. The light can have a wavelength between about 470 nm and about 510 nm or can have a wavelength of about 490 nm. The DsChR protein can additionally comprise substitutions, deletions, and/or insertions introduced into a native amino acid sequence to increase or decrease sensitivity to light, increase or decrease sensitivity to particular wavelengths of light, and/or increase or decrease the ability of the DsChR protein to regulate the polarization state of the plasma membrane of the cell. Additionally, the DsChR protein can comprise one or more conservative amino acid substitutions and/or one or more non-conservative amino acid substitutions. A DsChR protein containing substitutions, deletions, and/or insertions introduced into the native amino acid sequence suitably retains the ability to transport ions across the plasma membrane of an excitable cell, e.g., a neuron, in response to light.

In some embodiments, a hyperpolarizing light-responsive ion channel is based on a depolarizing light-responsive ion channel, as described in, e.g., PCT App. No. PCT/US2015/23087, which is incorporated herein by reference. In some embodiments, a light-responsive anion channel polypeptide is based on a C1C2 protein (Genbank Accession No.: AHA49646). In some embodiments, a suitable hyperpolarizing light-responsive polypeptide is based on the amino acid sequence of the protein ChR2 (Genbank Accession No.: AER29835). In some embodiments, a suitable hyperpolarizing light-responsive polypeptide is based on the amino acid sequence of the protein C1V1 (Genbank Accession No.: AEL28924). In some embodiments, a subject hyperpolarizing light-responsive polypeptide is based on the amino acid sequence of the protein ReaChR (Genbank Accession No.: AGT48260).

Also provided herein is a fluorescent moiety or light-responsive polypeptide encoded in a nucleic acid, e.g., encoded as part of an expression vector. In such instances, the excitable cells, e.g., neurons, may be genetically modified with the nucleic acid to adapt the excitable cells to emit fluorescence and/or to hyperpolarize and/or depolarize in response to a laser light stimulus. Any suitable nucleic acid and expression vector may be used to encode the fluorescent moiety.

In some embodiments, a portion of a nucleic acid encoding a fluorescent protein or light-responsive polypeptide is operably linked to a promoter sequence. Any suitable promoter that functions in the excitable cell of interest in the target tissue can be used for expression of the subject nucleic acids. In certain embodiments, a promoter sequence can be a promoter that is specific to a particular target cell type or to a particular tissue type, such as a particular excitable cell, a particular muscle cell, a particular neuron or a pan-neuronal promoter. Initiation control regions of promoters, which are useful to drive expression of nucleic acids in a specific animal cell, are numerous and familiar to those skilled in the art. Virtually any promoter capable of driving expression of the subject nucleic acids can be used. In some embodiments, the promoter used to drive expression of a subject protein can be the Thy1 promoter (See, e.g., Llewellyn, et al., 2010, Nat. Med., 16(10):1161-1166). In some embodiments, the promoter used to drive expression of a subject protein can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the a subject nucleic acid sequence in a target cell.

In some embodiments, a promoter may be an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some embodiments, a light-activated polypeptide-encoding nucleic acid may include a ribosomal skip sequence that can be used to generate two separate proteins from the same transcript. In such embodiments, a light-activated polypeptide-encoding nucleic acid will typically include a coding sequence that encodes a light-responsive protein as well as an activity-sensitive fluorescent protein, e.g., a neuronal activity-sensitive fluorescent protein. In these embodiments, a ribosomal skip sequence may be placed between the two coding sequences to produce two distinct proteins (namely, the light-responsive protein and the cellular electrical activity-sensitive fluorescent protein) from the same transcript.

Also provided herein are recombinant expression vectors containing a light-activated polypeptide-encoding nucleic acid or any variant thereof as described herein. Vectors according to the present disclosure also include vectors containing a nucleotide sequence that encodes an RNA (e.g., an mRNA) that when transcribed from the vector will result in the accumulation of a subject protein in the on excitable cells, e.g., neurons, in the target tissue, including accumulation of light-responsive ion channels on the plasma membrane. Vectors which may be used include, without limitation, lentiviral, HSV, adenoviral, and adeno-associated viral (AAV) vectors. Lentiviruses include, but are not limited to HIV-1, HIV-2, SIV, FIV and EIAV. Lentiviruses may be pseudotyped with the envelope proteins of other viruses, including, but not limited to VSV, rabies, Mo-MLV, baculovirus and Ebola. Such vectors may be prepared using standard methods in the art.

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore. M E Bloom, R M Linden, C R Parrish, Eds.) p 5-14, Hudder Arnold, London, UK (2006); and D E Bowles, J E Rabinowitz, R J Samulski "The Genus Dependovirus" (J R Kerr, S F Cotmore. M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the system and method of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596,535, the disclosure of which is hereby incorporated by reference in its entirety.

In some embodiments, the subject light-responsive proteins can be combined with various promoters and/or fluorescent proteins (XFP) for targeting specific neuronal populations in mammalian brains. For example, the following adeno associated vectors (AAVs) and components thereof may be used without limitation: AAV-CamKII-X-XFP, AAV-hSyn-X-XFP, AAV-mThy1-X-XFP, AAVmThy1-X-XFP, AAV-GFAP-X-XFP, AAV-VGAT-X-XFP, AAV-PET1-X-XFP, AAV-NPY-X-XFP, AAV-SST-X-XFP, AAV-AVP5.5-X-XFP, AAV-Ef1a-X-XFP, AAV-FLEX-rev-X-XFP, AAV-CAG-X-XFP, AAV-CAG-FLEX-X-XFP, where X is a light-responsive protein. Other AAV vectors that may be used in association with the polynucleotides include those with double floxed inverted reading frames (DIO) which allow expression of proteins under the control of recombinases such as as Cre and Flp: AAV-Ef1a-DIO(Cre)-X-XFP (Cre-dependent expression), AAV-Ef1a-DIO(Flp)-X-XFP (Flp-dependent expression), AAV-Ef1a-DIO(Cre)-DIO(Flp)-X-XFP (Cre and Flp dependent expression), where X is a light-responsive protein.

Another major viral transduction system utilizes lentivirus including the following potential expression vectors: pLenti-CamKII-X-XFP, pLenti-Ef1a-X-XFP, pLenti-mThy1-X-XFP, pLenti-hThy1-X-XFP, pLenti-hSyn-X-XFP, pLenti-VGAT-X-XFP, pLenti-Hcrt-X-XFP, where X is a light-responsive protein. Herpes simplex virus (HSV) can be utilized to transport proteins of interest over synapses (anterograde) which includes the following expression vectors: HSV-EF1a-X-XFP and HSVEF1a-DIO-X-XFP, where X is a light-responsive protein. Rabies and pseudorabies virus can be utilized for retrograde transports over synapses using the following expression vector: SAD(delta)G-X-XFP and SAD(delta)G-DIO-X-XFP. Other mammalian expression vectors include: pcDNA3.1-CMV-X-XFP and pCAGGS-X-XFP, where X is a light-responsive protein.

Neuron-specific promoters and other control elements (e.g., enhancers) are known in the art. Suitable neuron-specific control sequences include, but are not limited to, a neuron-specific enolase (NSE) promoter (see, e.g., EMBL HSENO2, X51956; see also, e.g., U.S. Pat. Nos. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn et al. (2010) Nat. Med. 16:1161); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) Gene Therapy 11:52-60); a motor neuron-specific gene Hb9 promoter (see, e.g., U.S. Pat. No. 7,632,679; and Lee et al. (2004) Development 131:3295-3306); and an alpha subunit of Ca($^{2+}$)-calmodulin-dependent protein kinase II (CaMKIIα) promoter (see, e.g., Mayford et al. (1996) Proc. Natl. Acad. Sci. USA 93:13250). Other suitable promoters include EF1α and DAT.

In some embodiments, a non-human animal in which the target tissue is present is genetically engineered to express a fluorescent protein or a light-responsive polypeptide, as described herein, by using any suitable method of genetically engineering the animal, e.g., via genetic manipulation of embryonic stem cells. In some cases, a cell in a target tissue is genetically modified to express a fluorescent protein or a light-responsive polypeptide, as described herein. A genetically modified cell present in a target tissue can be present in a mammal, e.g., a human, a non-human primate, a rodent, a lagomorph, etc.

Any suitable method may be used to adapt excitable cells, e.g., neurons, to emit fluorescence and/or to hyperpolarize and/or depolarize in response to a laser light stimulus. In some embodiments, excitable cells may be contacted with a fluorescent moiety (e.g., a fluorescent dye or a fluorescent dye conjugated to a specific binding member), or a photo-sensitive caged compound, or a viral vector containing a nucleic acid encoding a light-responsive polypeptide and/or fluorescent protein, by delivering the fluorescent moiety, photo-sensitive caged compound, or the viral vector into the target tissue, locally or systemically. Any suitable composition for delivering the fluorescent moiety to a target tissue of interest may be used. Where compositions are to be delivered to a site in the brain, stereotactic injection can be used; see, e.g., Stein et al., J. Virol, 73:34243429, 1999; Davidson et al., PNAS, 97:3428-3432, 2000; Davidson et al., Nat. Genet. 3:219-223, 1993; and Alisky & Davidson, Hum. Gene Ther. 11:2315-2329, 2000, the contents of each of which are hereby incorporated by reference herein in their entireties.

Applications

Using the subject method and system, the ordinarily skilled artisan will be able to perform in vivo recording of the activity of excitable cells, such as neurons, in scattering tissue volumes using multifocal two photon illumination from a phase spatial light modulator. In some embodiments, the microlens array and sCMOS detector on the emission path of the microscope allows for high speed encoding of the detected emission from multiple sites, and the use of a computational deconvolution process allows reconstruction of the activity traces at each focal point. In some embodiments, in vivo calcium imaging may be performed substantially simultaneously on 100 or more neurons at 30 Hz or more for each neuron.

The present system and method also find use in multifocal stimulation of neurons in a large volume of the target tissue by spatio-temporal multiplexing the field of view of the spatial light modulator using the mirror galvanometers.

The present system and method also find use in analyzing or mapping the connectivity of neurons in target tissues, such as the brain. For example, the present system and method may be used to measure the individual activity of a plurality of neurons in a target tissue volume in response to a stimulus, either to one or more neurons in the local area of the target tissue that is being analyzed, or to sites distal to the measurement site. The stimulus may be a sensory stimulation, an electrical stimulation through an electrode, or an optical stimulation. By observing the pattern of activity of the measured neurons in response to various stimuli and other manipulations, one may deduce the connectivity of the neurons in the observed area of the target tissue.

In some embodiments, the neuronal region targeted for measurement or stimulation by the present system and method include any neocortical region. With proper tissue exposure, the target neural region includes: the hypothalamus, entorhinal and hippocampal formation cortex, mammillary bodies, septum, bed nucleus of stria terminalis, dorsal and ventral striatum, thalamus, amygdala, accumbens, brainstem, and subcortical structures in general. The target location may include: a cell, a portion of a cell, a plurality of cells, a bundle of nerve fibers, a neuromuscular junction, a central nervous system (CNS) tissue, a peripheral nervous system (PNS) tissue, muscle or cardiac tissue, or an anatomical region.

In some embodiments, the present system and method find use in screening in vitro/in vivo animal models of disease for neuronal circuit elements diagnostic of or causative for neuropsychiatric disease. Neuropsychiatric disease of interest may include disorders of mood and affect, anxiety, psychosis, personality, etc. The animal model may be any suitable model, including, but not limited to, rodents, cats, dogs, monkeys, and non-human primates. Perturbations used to model a neuropsychiatric disease include genetic models of neurological or psychiatric disease, such as autism; chronically induced models as with kainate or pilocarpine-induced epilepsy or chronic stress-induced depression; and acutely induced models as with hallucinogens or psychotogenic agents such as ketamine or phencyclidine (PCP). By comparing the difference in activity pattern between neurons in normal target tissue and neurons in abnormal target tissue, neural correlates of the neuropsychiatric disorder may be identified. Optical control of neurons in the target tissue may then allow identification of causative neuronal activity patterns for a particular neuropsychiatric disorder. These manipulations may potentially provide novel treatment targets.

In some embodiments, the present system and method find use in methods for identifying a treatment, e.g., a therapeutic treatment, with a desired activity on a group of neurons. If the desired outcome is known, then the present system and method may be used to screen for treatments, including, but not limited to, pharmacological agents, nonchemical based therapeutic treatment; behavioral treatment; electrical, magnetic, or optical based neural-modulation treatment; etc., that will bring about the desired neuronal activity pattern. The screening may be performed in any suitable animal model, either normal, or a model for a neurological disorder, such as Alzheimer's and Parkinson's disease, mild cognitive impairment, other dementias, and Down's Syndrome, as well as schizophrenia, autism, mood, affective, anxiety, and personality/developmental disorders.

In some embodiments, the present system and method find use in the treatment of a condition or disorder, such as a neurological or psychiatric condition using optogenetic control (closed loop control). As real time activity of neurons is monitored using the present system and method, a controller may be configured to modulate the activity of neurons in response to the imaged activity signals in such a way as to treat or reduce symptoms of the condition or disorder, at the behavioral and/or physiological levels.

Notwithstanding the appended claims, the present disclosure is also defined by the following clauses:

1. A method for measuring the activity of excitable cells in a target tissue, the method comprising:
    i) selecting a first plurality of excitable cells in a target tissue for measuring activity, wherein the excitable cells are adapted to emit fluorescence in a cellular electrical activity-sensitive manner; and
    ii) measuring the activity of each of the excitable cells by:
        a) illuminating the first plurality of excitable cells with spatio-temporally multiplexed three-dimensional (3D) multi-focal light patterns, thereby causing the excitable cells to emit fluorescence, wherein the 3D multi-focal light patterns are generated using a spatial light modulator and a pair of mirror galvanometers to spatially translate a field of view of the spatial light modulator on the target tissue, and wherein different subsets of excitable cells from the first plurality are illuminated among at least some of the 3D multi-focal light patterns;
        b) recording, using an image detector, a multiplexed 2D diffraction pattern of the emitted fluorescence diffracted by a microlens array; and
        c) resolving the multiplexed 2D diffraction pattern to determine the activity of each excitable cell illuminated by the plurality of 3D multi-focal light patterns.

2. The method according to clause 1, wherein the illuminating comprises projecting a plurality of 3D multi-focal light patterns sequentially into the target tissue at a rate of at most about 0.75 times a maximum switching rate of the spatial light modulator.

3. The method according to clause 1 or 2, wherein the illuminating comprises using a mirror galvanometer.

4. The method according to any one of clauses 1 to 3, wherein the first plurality of excitable cells comprises at least 40 cells.

5. The method according to any one of clauses 1 to 4, wherein the different subsets of excitable cells comprise on average 90% or fewer cells than the first plurality of excitable cells.

6. The method according to any one of clauses 1 to 5, wherein the spatio-temporally multiplexed 3D multi-focal light patterns collectively have a power at the target tissue of about 500 mW or less.

7. The method according to any one of clauses 1 to 6, wherein measuring the activity of an individual excitable cell is performed at a frequency of from about 5 Hz to about 100 Hz.

8. The method according to any one of clauses 1 to 7, wherein resolving the multiplexed 2D diffraction pattern comprises deconvolving the multiplexed 2D diffraction pattern using an optical model for light propagation through an emission path from the target tissue to the image detector.

9. The method according to clause 8, wherein the optical model comprises an analytical model.

10. The method according to clause 9, wherein the optical model comprises a wave optics model.

11. The method according to clause 8, wherein the optical model comprises an empirical model.

12. The method according to clause 11, wherein the optical model comprises individual 2D diffraction patterns for fluorescence emitted by the first plurality of excitable cells and diffracted by the microlens array.

13. The method according to clause 12, further comprising obtaining individual 2D diffraction patterns for each of the first plurality of excitable cells in the target tissue, by a) contacting an excitable cell of the first plurality with a laser light, thereby causing the contacted excitable cell to emit fluorescence; and
b) recording, using the image detector, a 2D diffraction pattern of the emitted fluorescence diffracted by the microlens array.

14. The method according to clause 13, wherein the contacting comprises two-photon 2D laser scanning.

15. The method according to any one of clauses 12 to 14, wherein the deconvolving comprises determining individual point spread functions (PSFs) for each of the individual 2D diffraction patterns and using the individual PSFs to deconvolve the multiplexed 2D diffraction pattern.

16. The method according to any one of clauses 12 to 15, further comprising selecting members of the different subsets of the first plurality of excitable cells based on the individual 2D diffraction patterns.

17. The method according to clause 16, wherein the selecting members of the different subsets comprises:
    comparing the individual 2D diffraction patterns among each other; and
    selecting members of the different subset such that a minimum difference in the individual 2D diffraction patterns between excitable cells in any pair of the different subsets is at or above a threshold difference.

18. The method according to clause 17, wherein the threshold difference maximizes the minimum difference.

19. The method according to any one of clauses 1 to 18, wherein the 3D multi-focal laser light patterns are generated by spatially modulating a laser beam using the spatial light modulator.

20. The method according to clause 19, wherein the laser beam is pulsed at a frequency of from about 100 to about 500 kHz.

21. The method according to clause 19 or 20, wherein the laser beam has an average power of about 1.0 to about 3.0 W.

22. The method according to any one of clauses 19 to 21, wherein the laser beam has a pulse duration of about 100 to about 500 fs.

23. The method according to any one of clauses 1 to 22, wherein the selecting comprises:
    scanning the target tissue using a focused laser light, to generate an image of the target tissue; and
    identifying excitable cells in the image.

24. The method according to clause 23, wherein the focused laser light is pulsed at a frequency of about 10 to about 200 MHz.

25. The method according to clause 23 or 24, wherein the focused laser light is generated using a spatial light modulator.

26. The method according to any one of clauses 1 to 25, the image detector is a Complementary Metal Oxide Semiconductor (CMOS) detector.

27. The method according to any one of clauses 1 to 26, wherein the excitable cells comprise neurons.

28. The method according to any one of clauses 1 to 27, wherein the target tissue is an in vivo neuronal tissue.

29. The method according to any one of clauses 1 to 28, wherein the target tissue is a light-scattering tissue.

30. The method according to any one of clauses 1 to 29, wherein the excitable cells are adapted to emit fluorescence in a calcium- or voltage-sensitive manner.

31. The method according to clause 30, wherein the excitable cells comprise an activity-sensitive fluorescent dye.

32. The method according to clause 30, wherein the excitable cells comprise a genetically encoded, activity-sensitive fluorescent protein.

33. The method according to any one of clauses 1 to 32, wherein the 3D multi-focal light patterns comprise light having a wavelength in the near-infrared range.

34. The method according to any one of clauses 1 to 33, wherein the method further comprises:
   stimulating the target tissue; and
   measuring the activity of the first plurality of excitable cells in response to the stimulation.

35. The method according to clause 34, wherein the target tissue comprises a second plurality of excitable cells that are adapted to hyperpolarize and/or depolarize in response to a laser light stimulus, and the stimulating comprises contacting the second plurality of excitable cells with a laser light stimulus.

36. The method according to clause 35, wherein an excitable cell that is adapted to hyperpolarize and/or depolarize in response to a laser light stimulus is genetically modified to express one or more light-responsive polypeptides that hyperpolarize or depolarize the excitable cell when contacted by a laser light.

37. A method of regulating the activity of a plurality of excitable cells in a target tissue, comprising:
   i) measuring the activity of a first plurality of activity-sensitive fluorescence-emitting excitable cells in a target tissue comprising a second plurality of excitable cells, according to the method of any one of clauses 1 to 33; and
   ii) modulating the activity of the second plurality of excitable cells in the target tissue in response to the measured activity of the first plurality of activity-sensitive fluorescence-emitting excitable cells.

38. The method of clause 37, wherein excitable cells of the second plurality are genetically modified to hyperpolarize and/or depolarize in response to a laser light stimulus, and the modulating comprises contacting the genetically modified excitable cells of the second plurality with a light stimulus using one or more 3D multi-focal light pattern stimuli, wherein the one or more 3D multi-focal light pattern stimuli are controlled in response to the measured activity of one or more of the plurality of activity-sensitive fluorescence-emitting excitable cells.

39. A system comprising:
   i) a light microscope defining an excitation path and an emission path with respect to a target tissue, wherein the excitation path comprises:
      a spatial light modulator configured to modify a first light generated by a light source, and to thereby project a 3D multi-focal laser light pattern into the target tissue; and
      a pair of mirror galvanometers configured to spatially translate a field of view of the spatial light modulator on the target tissue,
      and wherein the emission path comprises a microlens array configured to modify fluorescence emitted by the target tissue such that a 2D diffraction pattern is projected onto an image detector;
   ii) a controller; and
   iii) a processor configured to execute instructions that cause:
      the controller to:
         illuminate the target tissue with spatio-temporally multiplexed 3D multi-focal light patterns, thereby causing the excitable cells to emit fluorescence, and record a multiplexed 2D diffraction pattern of the emitted fluorescence; and
      the processor to resolve the recorded multiplexed 2D diffraction pattern.

40. The system according to clause 39, wherein the light source is configured to generate a second light, and wherein the excitation path comprises a first movable mirror configured to direct
   the first light onto the spatial light modulator when the first movable mirror is in a first position, and
   the second light onto the spatial light modulator when the first movable mirror is in a second position.

41. The system according to clause 39 or 40, wherein the light source is a laser light source and the light is a laser beam.

42. The system according to clause 41, wherein the laser light source comprises a regenerative amplifier configured to modify the first laser beam.

43. The system according to any one of clauses 39 to 42, wherein the emission path comprises a photodetector, and wherein the emission path comprises a second movable mirror configured to direct the fluorescence emitted by the target tissue to:
   the microlens array when the second movable mirror is in a first position, and
   the photodetector when the second movable mirror is in a second position.

44. The system according to any one of clauses 39 to 43, wherein the emission path comprises an achromatic doublet configured to expand the first laser beam or the second laser beam directed onto the spatial light modulator.

45. The system according to any one of clauses 39 to 44, wherein the spatial light modulator has a maximum switching rate of at least about 40 Hz.

46. The system according to any one of clauses 39 to 45, wherein the spatial light modulator has a resolution of at least 256 pixels×at least 256 pixels.

47. The system according to any one of clauses 39 to 46, wherein the first light has a wavelength in the near-infrared range.

48. The system according to any one of clauses 39 to 47, wherein the excitation path comprises a Pockels cell configured to reduce power of the first light such that the spatio-temporally multiplexed 3D multi-focal light patterns has an average power at the target tissue of about 500 mW or less.

49. The system according to any one of clauses 39 to 48, wherein the image detector is a CMOS detector.

50. A method for collectively and specifically illuminating a plurality of excitable cells in a target tissue, the method comprising:
   i) selecting a plurality of excitable cells in a target tissue, wherein excitable cells of the plurality are adapted to emit fluorescence; and
   ii) sequentially projecting into the target tissue each 3D multi-focal light pattern of spatio-temporally multiplexed 3D multi-focal light patterns generated using a spatial light modulator and a pair of mirror galvanometers to spatially translate a field of view of the spatial light modulator on the target tissue, wherein the 3D multi-focal light patterns illuminate different subsets of the plurality of excitable cells, thereby collectively and specifically illuminating the plurality of excitable cells in the target tissue.

51. The method according to clause 50, wherein the 3D multi-focal light patterns are sequentially projected into the target tissue at a rate of at most about 0.75 times a maximum switching rate of the spatial light modulator.

52. The method according to clause 50 or 51, wherein the different subsets of excitable cells comprise on average 90% or fewer cells than the plurality of excitable cells.

53. The method according to any one of clauses 50 to 52, wherein the excitable cells are neurons.

54. The method according to clause 53, wherein the target tissue is an in vivo neuronal tissue.

55. The method according to any one of clauses 50 to 54, wherein the target tissue comprises a population of excitable cells that are adapted to hyperpolarize and/or depolarize in response to a light stimulus.

56. The method according to clause 55, wherein excitable cells of the population are genetically modified to express one or more light-responsive polypeptides that hyperpolarize or depolarize the excitable cell when illuminated by the light stimulus.

57. The method according to any one of clauses 50 to 56, wherein the 3D multi-focal light patterns collectively have a power at the target tissue of about 500 mW or less.

58. The method according to any one of clauses 50 to 57, wherein excitable cells of the plurality are adapted to emit fluorescence in a cellular electrical activity-sensitive manner, and wherein the sequentially projecting each of the 3D multi-focal light patterns is sufficient to cause the excitable cells of the first plurality in the target tissue to emit fluorescence when illuminated by a 3D multi-focal laser light pattern.

59. The method according to clause 58, further comprising iii) measuring the activity of excitable cells in the plurality by:
    recording, using an image detector, a multiplexed 2D diffraction pattern of the emitted fluorescence diffracted by a microlens array; and
    resolving the multiplexed 2D diffraction pattern to determine the activity of each excitable cell illuminated by the plurality of 3D multi-focal light patterns.

60. The method according to clause 59, wherein the resolving comprises deconvolving the multiplexed 2D diffraction pattern using an optical model for light propagation through an emission path from the target tissue to the image detector.

61. The method according to clause 60, wherein the optical model comprises an analytical model.

62. The method according to clause 61, wherein the optical model comprises a wave optics model.

63. The method according to clause 60, wherein the optical model comprises an empirical model.

64. The method according to clause 63, wherein the optical model comprises individual 2D diffraction patterns for fluorescence emitted by the plurality of excitable cells and diffracted by the microlens array.

65. The method according to clause 63 or 64, wherein the individual 2D diffraction patterns are obtained by
    a) contacting an excitable cell in the plurality of excitable cells with a laser light, thereby causing the excitable cell to emit fluorescence;
    b) directing the emitted fluorescence from the contacted excitable cell through a microlens array to create a 2D diffraction pattern; and
    c) recording the 2D diffraction pattern.

66. The method according to clause 65, wherein the contacting comprises two-photon 2D laser scanning.

67. The method according to any one of clauses 63 to 66, further comprising selecting members of the different subsets of the plurality of excitable cells based on the individual 2D diffraction patterns.

68. The method according to clause 67, wherein the selecting members of the different subsets comprises:
    comparing the individual 2D diffraction patterns among each other; and
    selecting members of the different subset such that a minimum difference in the individual 2D diffraction patterns between excitable cells in any pair of the different subsets is at or above a threshold difference.

69. The method according to clause 68, wherein the threshold difference maximizes the minimum difference.

70. The method according to any one of clauses 59 to 69, wherein measuring the activity of an excitable cell is performed at a frequency of from about 5 Hz to about 100 Hz.

71. The method according to any one of clauses 59 to 70, wherein the image detector is a CMOS detector.

72. The method according to any one of clauses 59 to 71, wherein the excitable cells are adapted to emit fluorescence in a calcium- or voltage-sensitive manner.

73. The method according to any one of clauses 59 to 72, wherein the excitable cells comprise an activity-sensitive fluorescent dye.

74. The method according to any one of clauses 59 to 72, wherein the excitable cells comprise a genetically encoded, activity-sensitive fluorescent protein.

75. The method according to any one of clauses 59 to 74, wherein the method further comprises:
    stimulating the target tissue; and
    measuring the activity of individual excitable cells in the plurality of excitable cells in response to the stimulation.

76. The method according to any one of clauses 50 to 75, wherein the target tissue is a light-scattering tissue.

77. The method according to any one of clauses 50 to 76, wherein the first subset comprises 10 or more excitable cells.

78. The method according to any one of clauses 50 to 77, wherein the 3D multi-focal light pattern is generated by spatially modulating an amplitude and/or phase of a laser beam using the spatial light modulator.

79. The method according to clause 78, wherein the laser beam is pulsed at a frequency of from about 100 to about 500 kHz.

80. The method according to clauses 78 or 79, wherein the laser beam has an average power of from about 1.0 to about 3.0 W.

81. The method according to any one of clauses 78 to 80, wherein the laser beam has a pulse duration of from about 100 to about 500 fs.

82. The method according to any one of clauses 78 to 81, wherein the laser beam has a wavelength in the near-infrared range.

83. The method according to any one of clauses 50 to 82, wherein the selecting comprises:
    scanning the target tissue using a focused laser light, to generate an image of the target tissue; and
    identifying excitable cells in the image.

84. The method according to clause 83, wherein the focused laser light is pulsed at a frequency of from about 10 to about 200 MHz.

85. The method according to clause 83 or 84, wherein the focused laser light is generated using a spatial light modulator.

EXAMPLES

As can be appreciated from the disclosure provided above, the present disclosure has a wide variety of applications. Accordingly, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Example 1

Multisite Random Access Two-Photon Three-Dimensional In Vivo Optical Recording of Neural Activity Materials and Methods
Scanless Three-Dimensional Two-Photon Imaging The microscope included a multifocal near-infra-red (NIR) excitation path and a visible detection path (FIG. 1A). In the two-photon excitation path, pulses from a 2 Watt, 80 MHz, 150 fs, Ti:Sapphire laser (Coherent, Chameleon®) tuned to 920 nm were either sent directly to the rest of the microscope optics through a Pockels cell (Conoptics) for intensity control, or used as a seed laser for a regenerative amplifier (Coherent RegA® 9000) customized to produce 1.8 W at 250 kHz, 150 fs pulses which are sent to a separate Pockels cell (Conoptics). Both beams were passed through half wave plates (Thorlabs) used to match the beam polarizations to that required by the spatial light modulator (SLM). One of the two lasers were selected using a motorized mirror (Newport) and were expanded using NIR achromatic doublets (Thorlabs) to a $1/e^2$ diameter of 10 mm before reflecting off a 19.2 mm×19.2 mm, 512×512, 0-2*n phase spatial light modulator (Meadowlark) at a 15 degree angle from the normal. The SLM was imaged using a 2f1+2f2 configuration relay lens pair on to a 6-mm galvanometer mirror (Cambridge Technology) and a 6-mm y-galvo spaced 1 cm apart, equidistant from the conjugate SLM plane. In between lens f1 and lens f2, a beam block (2 mm steel pin inserted at center of glass window, Thorlabs) was used to block the zero order undiffracted light from the SLM. Finally, another pair of relay lenses (Leica scan lens, Nikon tube lens) relayed the image of the SLM through a short pass dichroic (Chroma) and onto the back aperture of the objective.

One arm of the emission path followed the light field microscope configuration. On the emission path, light went through the short pass dichroic, through a tube lens (Nikon) and onto a microlens array (RPC Photonics, 125 um pitch, f/10) placed at the image plane. A pair of relay lenses (Nikon 35 mm, Nikon 50 mm) set to infinity focus and with aperture wide open were used to image the camera (Hamamatsu Orca™ Flash4.0 V2) to a plane one microlens focal length behind the microlens array (1.25 mm). This path was used to simultaneously record emission from multiple focal points, and for three dimensional (3D) calibration of the microscope.

The second arm of the emission path, realized by a removable mirror before the tube lens in the previous illumination path, sent the emission through another separate tube lens (Nikon) through a focusing lens and onto a photo multiplier tube (Hamamatsu).
Calibration A calibration procedure was used to ensure the cell locations defined by coordinates in the reference 3D stack of dense image frames can be accurately illuminated by the SLM excitation path. In order to achieve this, spots in a fluorescent volume (Sharpie® highlighter dye in a cuvette (Thorlabs) with coverslip) were illuminated and the 3D location of those spots was reconstructed using the light field microscope as a reference coordinate system. This calibration was done for the Chameleon® SLM path, the RegA® SLM path, and the Chameleon® SLM galvo paths. For each calibration, a 2 dimensional (2D) affine transform was fitted at one of two z-depths, and linear interpolation was used to determine the affine transform for other z-depths. With the same fluorescent volume, the position of the wave plates and the grating in the dispersion compensation unit could be optimized to maximize signal. This procedure was repeated once at the beginning of each experiment day.
Data Acquisition First, a 3D stack of dense image frames was acquired by scanning with the galvanometer mirrors a single laser point focused to a given z-depth by the SLM and recording the emission onto the PMT. ScanImage software was used to analyze the emissions. Cells were then hand selected for imaging.

Next, each cell was illuminated one at a time, and the emission was recorded through the light field microscope emission path onto the camera. These empirical measurements of the optical model were later used for deconvolution.

All the cells to non-overlapping subsets can be assigned by maximizing the minimum similarity between two cells in any given subset.

Finally, for actual recording, a set of phase masks were pre-computed, where each mask illuminates one subset of cells.
Control Electronics and Timing A computer running Windows® 7, 64-bit and custom MATLAB® software was used to control all hardware. Analog and digital control signals were generated using DAQ cards (NI DAQ). The camera was operated with external triggering. ScanImage software was used to control the galvanometer mirrors for acquiring the 3D stack of dense image frames.
Results A combination of simultaneous multi-focal two-photon excitation, simultaneous 3D imaging and the use of regenerative amplifier, in conjunction with an empirically measured optical model and computational deconvolution, were utilized to enable fast recording of neuronal activity with genetically-encoded calcium indicators with single cell resolution deep in tissue (FIGS. 1A-1D). A regenerative amplifier was used to generate over an order of magnitude more two photon fluorescence signal compared with a conventional Ti:Saph laser, both operating at 920 nm for GCaMP6.

FIGS. 1A-1D: Design of a multisite random access targeting microscope. (FIG. 1A) Schematics of microscope setup. PC, Pockels cell; S, shutter; HWP, half-wave plate; RM1-2, removable mirrors; L1-6, lenses; SLM, spatial light modulator; ZB, zero order beam block; GM, galvanometer mirrors; SL, scan lens; TL, tube lens; F, filter; PMT, photomultiplier tube; MLA, microlens array. (FIG. 1B) A phase spatial light modulator generates simultaneous 3D multifocal illumination patterns which are positioned and dithered by galvanometer mirrors on sites of interest pre-specified from a 3D two-photon image stack. (FIG. 1C) The resultant two-photon excited fluorescence emission is imaged through a microlens array onto an image sensor, where the emission from each target has a unique diffraction pattern (FIG. 1D) A measurement matrix constructed from individually illuminated targets is used to solve for the fluorescence at each target for each sensor image.

Cycling through illuminating subsets of targets at exactly half the maximum SLM switching speed was the optimal speed for maximizing signal rate (FIG. 2).

Figure 3:
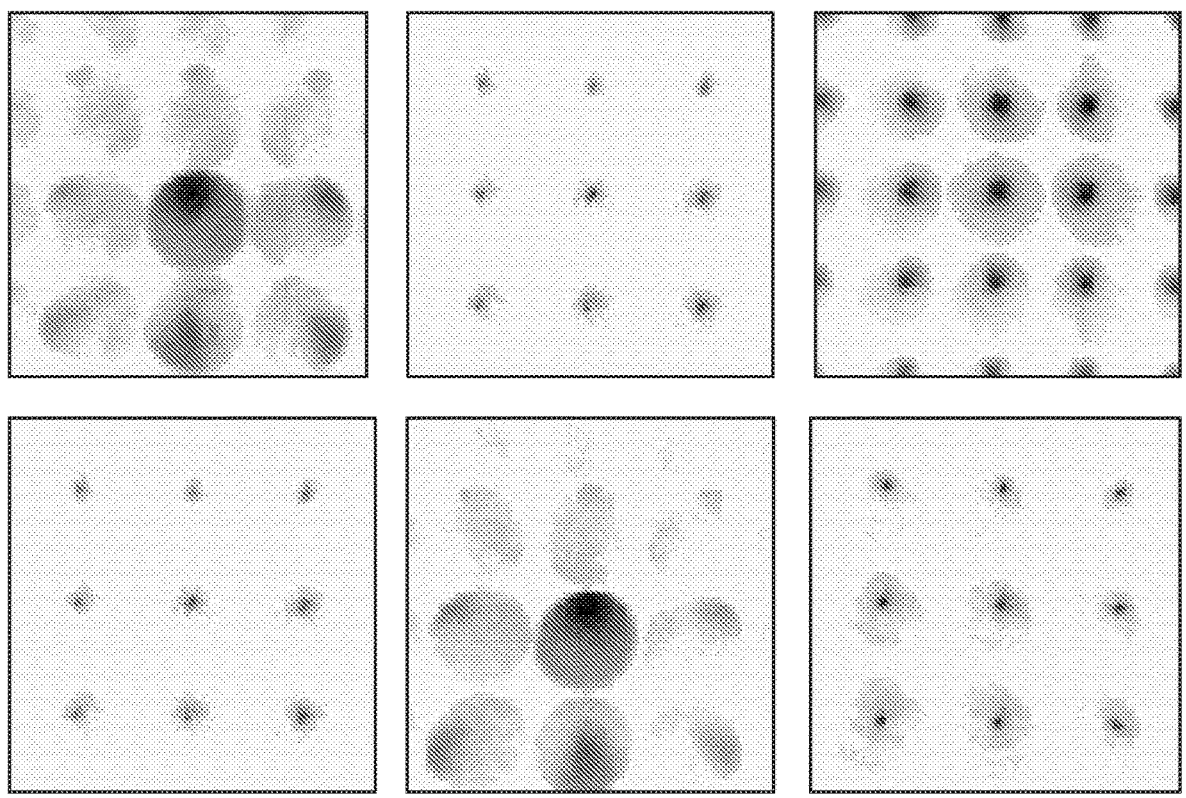
FIG. 3 is a collection of images showing the difference in the point spread functions obtained from empirical measurements in a target tissue and in a control sample.

The output of this laser system was focused into a multifocal 3D excitation pattern using a phase spatial light modulator at an optical plane conjugate to the back aperture of the microscope objective with a phase pattern computed using the Gerchberg Saxton algorithm. The resulting time varying fluorescence from multiple locations in the sample in 3D was imaged through the detection configuration used in a microlens array positioned at a conjugate image plane, onto a sCMOS image sensor placed via relay optics at exactly one microlens focal length behind the microlens array. Each recorded camera frame was an incoherent linear sum of the unique but potentially overlapping diffraction patterns from the various 3D locations, and the individual time traces for each point in 3D could be recovered by solving a least squares deconvolution problem. In order to accurately account for tissue aberrations of the visible wavelength emission though, rather than use an analytically calculated diffraction pattern for each point from a wave optics model of light propagation in an aberration free medium, the diffraction pattern from each point in a sample was explicitly measured during a calibration procedure before each recording experiment (FIGS. 1B and 1C; FIG. 3). This empirically measured optical model enabled the faithful reconstruction of sources even in the presence of refractive index heterogeneities (FIG. 1D).

Figure 2A:
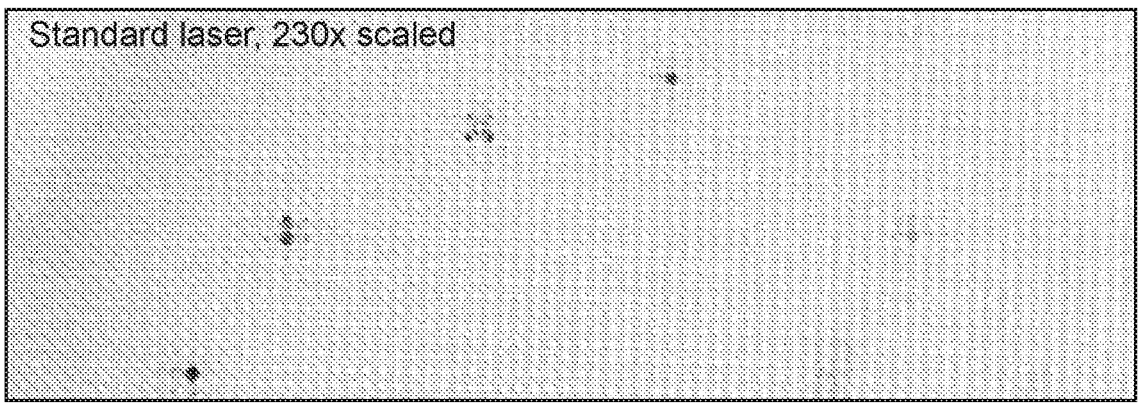
FIGS. 2A-2B are collection of images depicting the optimum laser beam frequency for us in the method according to embodiments of the present disclosure.
Figure 2B:
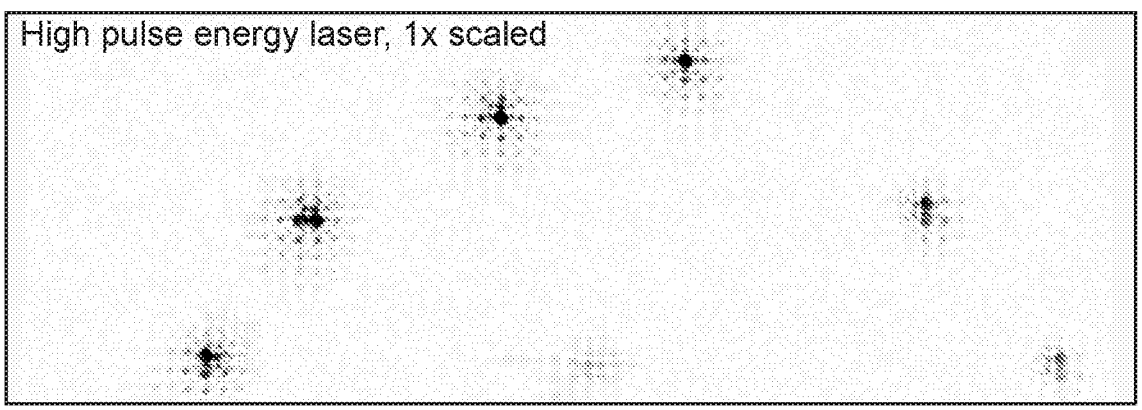

FIGS. 2A-2B: Laser repetition rate and signal rate. For the same average power, the 250 kHz repetition rate (FIG. 2B) yields approximately 230 times higher signal rate than the standard laser at 80 MHz repetition rate (FIG. 2A). This agrees well with the theoretical 240 times higher signal, where the difference may be attributable to differences in pulse duration.

FIG. 3: Necessity for using empirically measured point spread functions for deconvolution. Actual point spread functions measured in mouse cortex (magenta) are broader and often shifted from those measured in a scattering free (green) control sample (fluorescent dye in water).

The capabilities of this approach were demonstrated by in vivo imaging of mouse cortex neurons using a genetically encoded calcium indicator (FIGS. 4A-4E). After first acquiring full-frame 2D images across 51 z-depths spanning a volume of 700 µm by 700 µm by 200 µm using standard laser scanning two photon microscopy (with standard Ti:Saph laser) in a process of a few minutes, 106 cells from which to record were hand selected (FIG. 4B). In another process requiring several minutes, each cell was illuminated for a single focal point, and its unique diffraction pattern recorded on the image sensor (FIG. 1B). All of the cells were then illuminated simultaneously and images recorded at 10 Hz for spontaneous activity and stimulus-evoked activity (FIGS. 4C-4E).

FIGS. 4A-4E: 3D in vivo calcium imaging in an awake mouse responding to a whisker deflection stimulus (FIG. 4A) In vivo experiment setup. (FIG. 4B) Target recording sites are selected from a 3D two-photon image stack. Scale bar, 50 µm. (FIG. 4C) Spontaneous activity measured in 106 neurons. (FIG. 4D) Whisker deflection evoked responses measured in 106 neurons. (FIG. 4E) Representative traces from adjacent cells demonstrating single cell recording resolution.

Next, the requirement for simultaneity was relaxed, and a subset of 21 cells were illuminated each for 10 ms, to record from 106 cells at 10 Hz. This recording strategy, although not truly simultaneous, allows one to record from both more cells and to more easily separate the various sources, and may be considered as simultaneous within the limits of the particular calcium sensor in the present experiments. Reducing the number of cells illuminated to a subset that is smaller by a factor M allows one to record from the same number of cells but with sqrt(M) power, or to use the same total laser power to record from sqrt(M) more cells.

The SLM field of view could be increased by temporally multiplexing using galvanometer mirrors (FIGS. 5A-5B). Using temporal multiplexing of illumination patterns on the SLM can also increase two photon signal generation efficiency (FIGS. 5A-5B).

FIGS. 5A-5B: Improving signal rate and extending the field of view using spatio-temporal multiplexing. Without spatio-temporal multiplexing (FIG. 5A), the field of view is limited by the SLM resolution and diffraction efficiency. With spatio-temporal multiplexing (FIG. 5B), galvanometer mirrors are used to time division multiplex the illumination to various spatial regions, allowing for both more uniform illumination and higher signal rate.

The current limitations on number of cells that can be recorded from with reasonable SNR could be improved through a combination of using better lasers, faster spatial light modulators and faster cameras. In addition, real time motion correction methods could be used compensate for residual brain motion even in head fixed imaging settings.

Example 2

Extended Field-of-View and Increased-Signal 3D Holographic Illumination with Time-Division Multiplexing Experimental Setup The time-division multiplexing illumination approach was implemented on a microscope equipped with a SLM-based illumination system and galvanometer scanning mirrors, as illustrated in FIG. 8. A single-snapshot 3D imaging system (light field microscope) and a single-beam laser scanning two-photon imaging system were additionally incorporated to enable quantification of the two-photon excitation efficiency and 3D in vivo calcium imaging.

FIG. 8: Optical layout. The SLM, illuminated by a 920 nm femtosecond laser through a beam expander (BE), is imaged through lenses (L1, L2) and zero-order beam block (ZB) to the midpoint between two galvanometer scanning mirrors, and then to the objective pupil plane through a scan lens (SL), tube lens (TL) and short-pass dichroic mirror (D). Excited fluorescence filtered by an emission filter (F) is captured by either a photomultiplier tube (PMT) or light field microscope (LFM) with sCMOS camera, enabling single-snapshot 3D visualization of the excited fluorescence.

Optical Setup

In the excitation path, 920 nm pulses from a 80 MHz Ti:Sapphire laser (Coherent Chameleon® Ultra II) seeded a regenerative amplifier (Coherent RegA® 9000) producing 1.8 W at 250 kHz with 170 fs pulses. A Pockels cell (Conoptics 350-80-LA-02-RP KD*P) both reduced power and served as a high-speed shutter. The beam passed through a half wave plate (Thorlabs AHWP10M-980) and was expanded using achromatic doublets (Thorlabs) to slightly overfill a 6.14 mm×6.14 mm, 256×256 resolution, 0-2π phase SLM (Meadowlark HSP256-1064-P8) at a ~15 degree angle from the normal. The SLM was imaged ($f_1$=300 mm, $f_2$=200 mm) onto the midpoint between two 5-mm galvanometer mirrors (Cambridge Technology 6215H), spaced ~1 cm apart. A beam block (2 mm ø steel pin in a glass window, Thorlabs WG12012-B) blocked zero order undiffracted light. Finally, two lenses (Leica scan lens VIS-IR-TCS-SP2, f=39 mm and Thorlabs tube lens ITL200, f=200 mm) brought the conjugated SLM and scanning mirrors through a dichroic (Semrock FF670-SDi01-25×36) and onto the objective pupil (Nikon 16×0.8 NA), after which ~20% of the total laser power remained.

The fluorescence emission path followed the light field microscope configuration in Broxton et al., supra. Emission passed through a filter (Semrock FF01-535/50), an identical tube lens, microlens array (RPC Photonics, 125 μm pitch, f/10), two relay lenses (Nikon 35 mm, Nikon 50 mm), and an sCMOS camera (Hamamatsu Orca™ Flash4.0 V2). A MATLAB® program (MathWorks) controlled all hardware with a data acquisition card (National Instruments PCIe-6343).

3D holograms computed with the multi-plane Gerchberg-Saxton method were used. For calibration and characterization experiments, a green fluorescent dye (Sharpie® highlighter) in a cuvette (Thorlabs CV10Q3500) capped with a 0.17 mm coverslip was used. The amplifier compressor stage was adjusted to compensate for pulse dispersion from the optics.

Calibration

The SLM transition time was determined to be $t_{SLM}$=7.5 ms by steering a single focal spot between two photodiodes placed just after ZB in FIG. 8 and measuring power as a function of time, plotted as the solid line in FIG. 7A, where the surrounding shaded region illustrates one standard deviation from three measurements.

With the geometric calibration procedure in Quirin et al. (Optics express 21(13), 16007-16021 (2013)), the 2D affine transforms between each z-depth of the light field microscope and SLM field of view was determined for each of 9 galvanometer mirror positions. For each mirror position at two z-depths, the 2D transform was measured by illuminating multiple focal spots in fluorescent dye and recording the resulting 3D light field coordinates; the transforms for the other z-depths were linearly interpolated.

Modifications for 3D Two-Photon In Vivo Calcium Imaging with Time-Division Multiplexing To enable 3D in vivo calcium imaging, two flip mirrors (Newport 8892-K) were used to switch between the 80 MHz and 250 kHz lasers, and between a photomultiplier tube (Hamamatsu H10770P A-40) and the sCMOS camera/microlens array, enabling single-beam 2D laser-scanning two-photon microscopy. The geometric calibration procedure described above ("Calibration") was extended to include this third coordinate system by registering the corners of the 2D scanned field of view in dye with the light field microscope coordinates at each z-depth.

A 512×512 resolution, but slower ($t_{SLM}$=10 ms), SLM (Meadowlark HVHSPDM512-532) was used, and to match the larger 19.2 mm SLM size to the objective pupil, the beam expansion (BE) was adjusted accordingly using $f_1$=750 mm and $f_2$=150 mm.

Imaging was performed 6 months after a chronic cranial window was implanted. Briefly, mice were sedated with isoflurane and a 5 mm diameter, #1 thickness cover slip (Warner) was implanted over barrel cortex after injection of 1000 μL of AAVdj-Camk2a-GCaMP6m virus. In addition, a plate for head-fixation during imaging was affixed to the skull using dental cement (Parkell). The Stanford University Institutional Animal Care and Use Committee approved all experimental protocols.

Results

Figure 9:
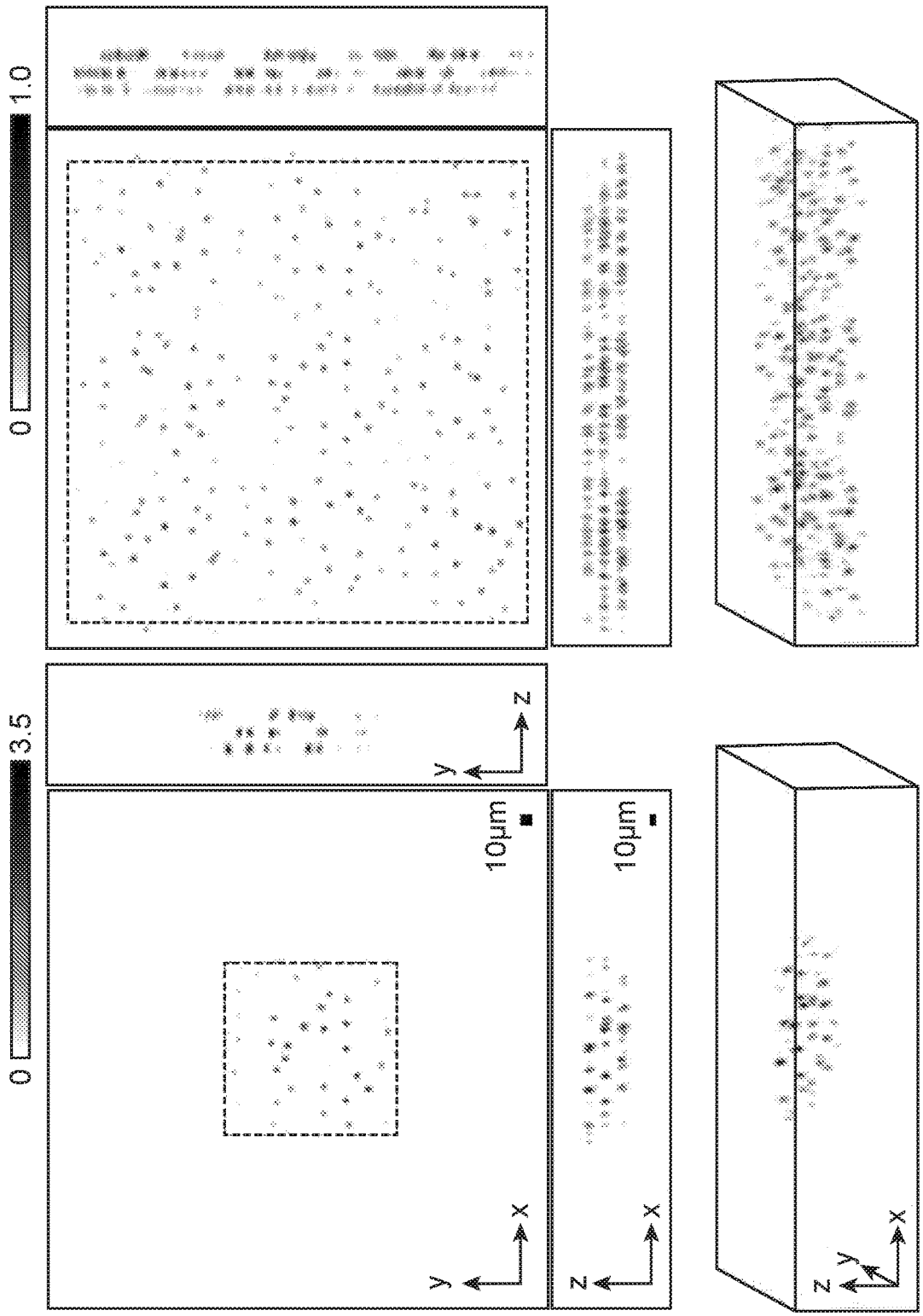
FIGS. 9A-9B are a collection of images showing experimentally measured increase in SLM field of view, according to embodiments of the present disclosure.

Extending Field of View 3D-reconstructed volumes of a fluorescent dye solution illuminated with and without an extended field of view were analyzed. In each case, the same 324 focal points in a 420 μm×420×200 μm volume were illuminated within a single camera exposure of T=100 ms using 36 mW (at the sample) to avoid saturation. In FIG. 9A, all focal points were illuminated simultaneously with the galvanometer mirrors in a fixed position. The lateral extent of the xy maximum projection after applying a 5% intensity threshold was 140 μm, matching the theoretical value of 140 μm as described by Eq. (2) above.

FIGS. 9A and 9B: Experimentally measured increase in SLM field of view during T=100 ms exposure. Measured 3D illumination patterns in a fluorescent dye solution (maximum intensity projections shown) illustrate the field of view increase, denoted by dashed lines, from (FIG. 9A) 140 μm×140 μm without, to (FIG. 9B) 380 μm×380 μm with, time-sequential galvanometer scanning.

In FIG. 9B time-division multiplexing of 9 SLM fields of view with 9 galvanometer positions was used to extend the field of view to 380 μm, an increase in area of 7.4 times. In addition, it should be possible to address the spatially varying diffraction efficiency visible in FIG. 9A by choosing the time-sequentially scanned fields of view to overlap further.

Increasing Two-Photon Signal

To quantify the two-photon signal gain from time-division multiplexing empirically, the illumination in a fluorescent dye solution was restricted to the same 33 focal points within the same single SLM field of view (as in FIG. 6A), to control for excitation and emission path vignetting effects, and measured the total detected counts on the image sensor as a function of the multiplexing factor, M, again with fixed laser power and camera exposure time of T=100 ms. A pockels cell shuttered the laser during the SLM transition periods in FIG. 7B. Measurements for each M were normalized with M=1, and compared with Eq. (8) in FIG. 10.

FIGS. 6A and 6B: Illustration of time-division multiplexing strategy for laterally extending the SLM field of view (FOV) of a holographic illumination system (FIG. 6A), where a pair of galvanometer mirrors at a conjugate pupil plane enable lateral time-sequential scanning of one of 9 different holograms to each of 9 regions (FIG. 6B). Drawings are to scale for the Nikon 16×0.8 NA objective lens (assuming 20 mm field number) and 256×256 SLM used in the experiments.

Figure 10:
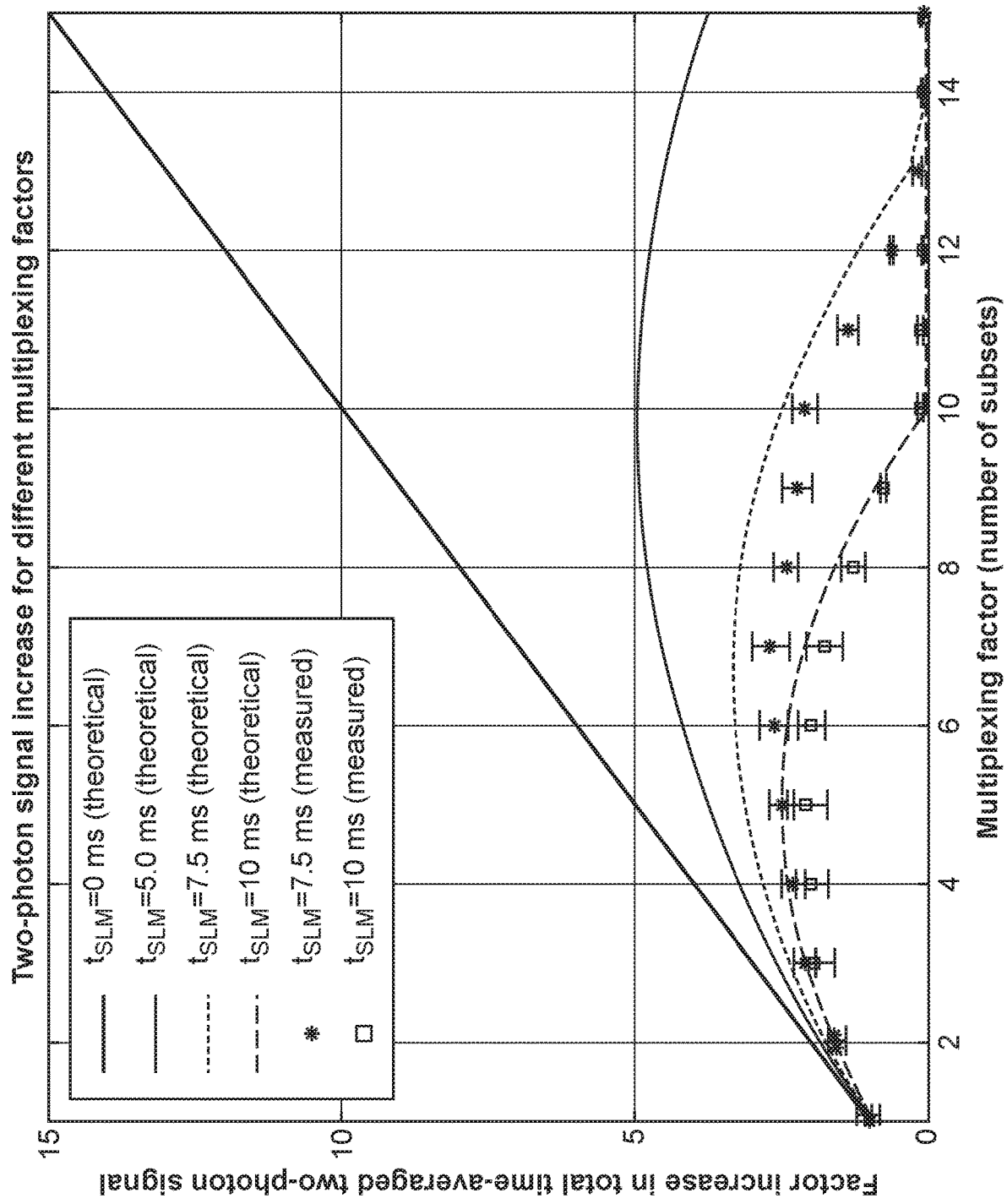
FIG. 10 is a graph showing theoretically computed and experimentally measured signal increase with SLM time-division multiplexing, according to embodiments of the present disclosure.

FIG. 10: Theoretically computed and experimentally measured signal increase with SLM time-division multiplexing, for fixed average laser power, total number of illuminated sites and exposure time (T=100 ms was used). SLMs with faster transition times may enable larger increases in total time-averaged two-photon signal with a greater number of subsets of focal sites illuminated sequentially. Error bars indicate one standard deviation.

For $t_{SLM}$=7.5 ms and $t_{SLM}$=10 ms, the maximum signal occurs at M=7 and M=5, respectively, compared with M=6.7 and M=5 predicted by Eq. (8). The slower $t_{SLM}$=10 ms SLM was approximated by keeping the pockels cell shuttered for this longer duration. The fact that the experimentally measured traces are slightly lower than the theoretically predicted curves might be explained by the limited precision with which the hardware can be synchronized, including the SLM, pockels cell and camera.

Finally, Eq. (8) plotted in FIG. 10 suggested that recent SLMs with even shorter transition times may approach the limit where $t_{SLM}$ tends toward 0 ms, where the increase in signal should scale exactly linearly with the number of multiplexed subsets.

Two-Photon 3D In Vivo Calcium Imaging with Time-Division Multiplexing

The 3D in vivo neuronal calcium imaging was applied using the microlens array in the light field microscope.

Figure 11A:
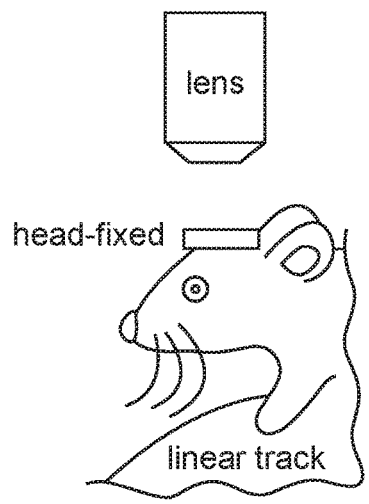
FIGS. 11A-11D are a collection of schematic diagrams, graphs and images showing 3D two-photon in vivo calcium imaging using 3D Holographic Illumination with Time-Division Multiplexing, according to embodiments of the present disclosure.
Figure 11B:
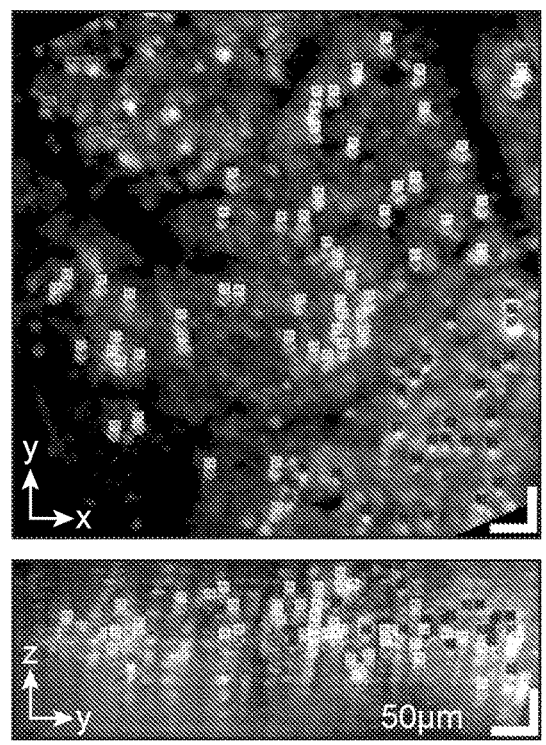

Briefly, fluorescence representing calcium activity of the neurons in an awake, head-fixed mouse, shown in FIG. 11A, was imaged through the cranial window using the following approach. In the first step, lasting several minutes, single-beam 2D laser scanning two-photon imaging yielded high-spatial resolution images identifying the locations of neurons at each of 51 z-depths defined by an SLM-implementation of a quadratic phase. 104 neurons of interest spanning 600 μm×600 μm×200 μm from this 3D image stack were then select for high-speed recording and were grouped into M=5 subsets. Next, the time-division multiplexing approach was used with 250 kHz laser with 71 mW (at the sample) to excite fluorescence at all sites, which was recorded through the microlens array and in a single T=100 ms camera exposure. From each camera image the fluorescence contribution from each of the illuminated sites were extracted (more below), and by recording an image sequence, the underlying calcium activity was sampled at each site at a rate of 10 Hz, for a total duration of 50 seconds, as shown in FIG. 11C.

Figure 11C:
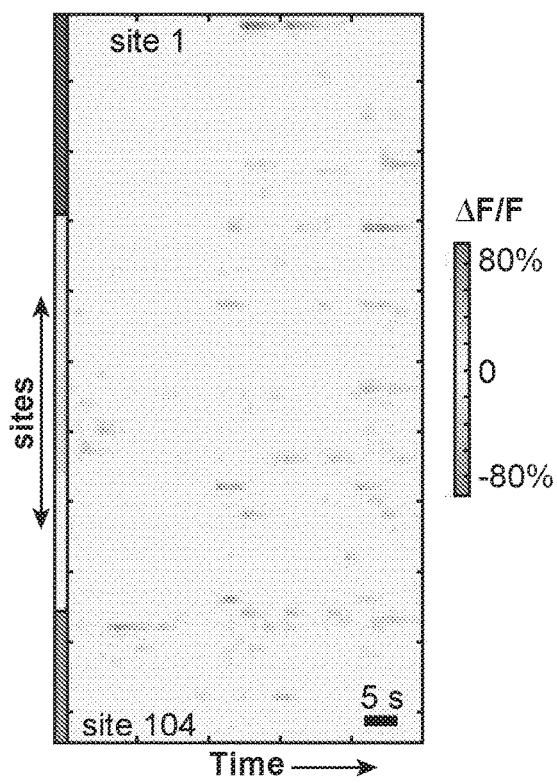
Figure 11D:
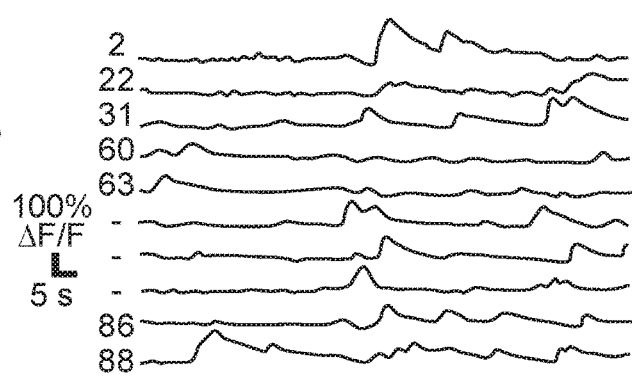

FIGS. 11A-D: 3D two-photon in vivo calcium imaging. (FIG. 11A) Neuronal activity in barrel cortex of an awake, head-fixed mouse is recorded. (FIG. 11B) 104 recording sites, centered on neurons, divided into M=5 subsets (annotated by number and subset) and spanning 600 μm×600 μm×200 μm, are selected from a single-beam raster-scanned two-photon image stack, and then illuminated using the present time-division multiplexing approach, enabling the sampling of (FIG. 11C) calcium signals across all sites at a rate of 10 Hz (T=100 ms). (FIG. 11D) Top 10 largest magnitude responses from (FIG. 11C).

In total, the M=5 illuminated sub-regions spanned an area about 4 times larger than the original SLM field of view of 300 μm×300 μm, and FIG. 11C demonstrated that spontaneous neural activity was observed in sites within every region. Additionally, the signal increase from multiplexing, in combination with other efficiency improvements, enabled in vivo mouse cortex recording using only 71 mW. Importantly, the limited kinetics of the GCaMP6m calcium sensor enabled time-division multiplex sampling of the sites with T=100 ms without sampling any less information than if all sites were had been sampled simultaneously.

For completeness, the following describes how the calcium measurements shown in FIG. 11C were extracted from raw camera images of the illuminated sites. The light field microscope projected fluorescence from each site in 3D to a unique image sensor diffraction pattern, which was calibrated empirically by recording an image of each site illuminated in isolation. (The unique image sensor diffraction pattern may also be determined analytically.) Because each raw camera image represents a linear superposition of the known, possibly overlapping, diffraction patterns of each of the illuminated sites, Richardson-Lucy deconvolution was used to solve for the fluorescence at each site. The AF/F, a normalized measure of activity, of each site plotted in FIG. 11C was this computed fluorescence across all camera frames divided by the baseline fluorescence, estimated using the $25^{th}$ percentile.

Example 3

Method of Implementing Closed-Loop Control of Neural Activity in a Target Tissue The present system and method to spatially resolve and detect fluorescence in conjunction with temporal multiplexing is used for implementing closed-loop 2D and 3D control. The system is adapted with an interface that allows implantation or fixation to a living and/or moving subject at a target location. The subject is a patient diagnosed with a neurological disorder, and the closed-loop control is configured to deliver feedback to the target tissue in response to an action taken either by the device, the software, the patient or by a caregiver. Real-time activity in defined excitable-tissue cells and circuit elements is imaged using chemical or genetically-encoded reporters of activity (such as $Ca^{2+}$, voltage, or biochemical signals) in conjunction with a real-time system for modulating the membrane potential or activity level of cells in response to imaged activity signals. The system also includes circuit elements containing optical control tools, such as microbial opsins, and the present system configured to illuminate and observe responses in target locations with light, and to modulate the wave length and/or the intensity of the light, frequency and/or the duration of the pulses of light. The system is configured to illuminate the target spot location in response to a user input, and to minimize spectral overlap between light used for control and light used for imaging.

The subject methods and systems may be used to treat a patient for a condition or disorder, such as a neurological or psychiatric condition or disorder, wherein closed-loop principles involve action taken either by the device, the software, the patient or by a caregiver) to deliver feedback to the target tissue.

Example 4

Method of Determining the Anatomical and Neural Activity Correlates of Neuropsychiatric Diseases The present system and method to spatially resolve and detect fluorescence in conjunction with temporal multiplexing is used for circuit screening in animal models for endophenotypes of neuropsychiatric disease. The system is adapted with an interface that allows implantation or fixation to a living and/or moving subject, e.g., a model organism, at a target location. Neural activity is assessed in a neural region having multiple subfields by observing a cellular response in at least one subfield or circuit element or ensemble thereof, in conjunction with or due to neural activity in another region or set of regions, in response to a behavioral event, a sensory stimulus, or a circuit intervention (e.g. electrical or optical). For optical control of the circuit, the cells in the target region express a light-activated channel/pump, and the cellular electrical response is evoked by optical stimulation of the light-activated channel/pump protein. Captured image data of the ensemble response is at a level sufficiently detailed in space and time to differentiate between portions of the subfield.

Identification of abnormalities or dysfunction is assessed in normal tissue and animals as well as in genetically, pharmacologically or physiologically perturbed tissues and animals Novel classes of events, motif, or ensemble activity are detected and observed with joint statistics across the 3D volume representing a crucial novel feature, allowing detection of volumetric motifs representing or encoding dysfunction. Highly novel treatment targets may be identified at the circuit or tissue ensemble level.

Example 5

Method of Screening for or Monitoring the Effects of Therapeutic Treatments for Neurological Disease The present system and method to spatially resolve and detect fluorescence in conjunction with temporal multiplexing is used for assessing effects of a treatment on endophenotypes or other readouts of physiological activity of the neural region or different subfields within the region. Readouts of physiological activity are compared with and without a treatment for the neural region. Endophenotypes and their response to intervention are assessed with respect their predictive value relative to a disorder's occurrence/magnitude and the extent of the treatment response.

Although the foregoing disclosure has been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims.

Accordingly, the preceding merely illustrates the principles of the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the present disclosure and the concepts contributed by the inventors to furthering the art, and are to be construed as being without limitation to such specifically recited examples and conditions. Moreover, all statements herein reciting principles, aspects, and embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A method for measuring the activity of excitable cells in a target tissue, the method comprising:
   i) selecting a first plurality of excitable cells in a target tissue for measuring activity, wherein the excitable cells are adapted to emit fluorescence in a cellular electrical activity-sensitive manner; and
   ii) measuring the activity of each of the excitable cells by:
      a) illuminating the first plurality of excitable cells with spatio-temporally multiplexed three-dimensional (3D) multi-focal light patterns, thereby causing the excitable cells to emit fluorescence, wherein the 3D multi-focal light patterns are generated using a spatial light modulator and a pair of mirror galvanometers to spatially translate a field of view of the spatial light modulator on the target tissue, and wherein different subsets of excitable cells from the first plurality are illuminated among at least some of the 3D multi-focal light patterns;
      b) recording, using an image detector, a multiplexed 2D diffraction pattern of the emitted fluorescence diffracted by a microlens array;
      c) resolving the multiplexed 2D diffraction pattern to determine the activity of each excitable cell illuminated by the plurality of 3D multi-focal light patterns, wherein resolving the multiplexed 2D diffraction pattern comprises deconvolving the multiplexed 2D diffraction pattern using an optical model for light propagation through an emission path from the target tissue to the image detector, wherein the optical model comprises individual 2D diffraction patterns for fluorescence emitted by the first plurality of excitable cells and diffracted by the microlens array; and
      d) selecting members of the different subsets of the first plurality of excitable cells based on the individual 2D diffraction patterns.

2. The method according to claim 1, wherein the illuminating comprises projecting a plurality of 3D multi-focal light patterns sequentially into the target tissue at a rate of at most about 0.75 times a maximum switching rate of the spatial light modulator.

3. The method according to claim 1, wherein the illuminating comprises using a mirror galvanometer.

4. The method according to claim 1, wherein the first plurality of excitable cells comprises at least 40 cells.

5. The method according to claim 1, wherein the different subsets of excitable cells comprise on average 90% or fewer cells than the first plurality of excitable cells.

6. The method according to claim 1, wherein the spatio-temporally multiplexed 3D multi-focal light patterns collectively have a power at the target tissue of about 500 mW or less.

7. The method according to claim 1, wherein measuring the activity of an individual excitable cell is performed at a frequency of from about 5 Hz to about 100 Hz.

8. The method according to claim 1, further comprising obtaining individual 2D diffraction patterns for each of the first plurality of excitable cells in the target tissue, by
   a) contacting an excitable cell of the first plurality with a laser light, thereby causing the contacted excitable cell to emit fluorescence; and
   b) recording, using the image detector, a 2D diffraction pattern of the emitted fluorescence diffracted by the microlens array.

9. The method according to claim 8, wherein the contacting comprises two-photon 2D laser scanning.

10. The method according to claim 1, wherein the deconvolving comprises determining individual point spread functions (PSFs) for each of the individual 2D diffraction patterns and using the individual PSFs to deconvolve the multiplexed 2D diffraction pattern.

11. The method according to claim 1, wherein the selecting members of the different subsets comprises:
   comparing the individual 2D diffraction patterns among each other; and selecting members of the different subset such that a minimum difference in the individual 2D diffraction patterns between excitable cells in any pair of the different subsets is at or above a threshold difference.

12. The method according to claim 11, wherein the threshold difference maximizes the minimum difference.

13. The method according to claim 1, wherein the plurality of 3D multi-focal laser light patterns are generated by spatially modulating a laser beam using the spatial light modulator.

14. The method according to claim 13, wherein the laser beam is pulsed at a frequency of from about 100 MHz to about 500 kHz.

15. The method according to claim 13, wherein the laser beam has an average power of about 1.0 W to about 3.0 W.

16. The method according to claim 13, wherein the laser beam has a pulse duration of about 100 fs to about 500 fs.

17. The method according to claim 1, wherein the selecting comprises:
scanning the target tissue using a focused laser light, to generate an image of the target tissue; and
identifying excitable cells in the image.

18. The method according to claim 17, wherein the focused laser light is pulsed at a frequency of about 10 MHz to about 200 MHz.

19. The method according to claim 17, wherein the focused laser light is generated using a spatial light modulator.

20. The method according to claim 1, the image detector is a Complementary Metal Oxide Semiconductor (CMOS) detector.

21. The method according to claim 1, wherein the excitable cells comprise neurons.

22. The method according to claim 1, wherein the target tissue is an in vivo neuronal tissue.

23. The method according to claim 1, wherein the target tissue is a light-scattering tissue.

24. The method according to claim 1, wherein the excitable cells are adapted to emit fluorescence in a calcium- or voltage-sensitive manner.

25. The method according to claim 24, wherein the excitable cells comprise an activity-sensitive fluorescent dye.

26. The method according to claim 24, wherein the excitable cells comprise a genetically encoded, activity-sensitive fluorescent protein.

27. The method according to claim 1, wherein the 3D multi-focal light patterns comprise light having a wavelength in the near-infrared range.

28. The method according to claim 1, wherein the method further comprises:
stimulating the target tissue; and
measuring the activity of the first plurality of excitable cells in response to the stimulation.

29. The method according to claim 28, wherein the target tissue comprises a second plurality of excitable cells that are adapted to hyperpolarize and/or depolarize in response to a laser light stimulus, and the stimulating comprises contacting the second plurality of excitable cells with a laser light stimulus.

30. The method according to claim 29, wherein an excitable cell that is adapted to hyperpolarize and/or depolarize in response to a laser light stimulus is genetically modified to express one or more light-responsive polypeptides that hyperpolarize or depolarize the excitable cell when contacted by a laser light.

31. A method of regulating the activity of a plurality of excitable cells in a target tissue, comprising:
i) measuring the activity of a first plurality of activity-sensitive fluorescence-emitting excitable cells in a target tissue comprising a second plurality of excitable cells, according to the method of claim 1; and
ii) modulating the activity of the second plurality of excitable cells in the target tissue in response to the measured activity of the first plurality of activity-sensitive fluorescence-emitting excitable cells.

32. The method of claim 31, wherein excitable cells of the second plurality are genetically modified to hyperpolarize and/or depolarize in response to a laser light stimulus, and the modulating comprises contacting the genetically modified excitable cells of the second plurality with a light stimulus using one or more 3D multi-focal light pattern stimuli, wherein the one or more 3D multi-focal light pattern stimuli are controlled in response to the measured activity of one or more of the plurality of activity-sensitive fluorescence-emitting excitable cells.

33. A system comprising:
i) a light microscope defining an excitation path and an emission path with respect to a target tissue, wherein the excitation path comprises:
a spatial light modulator configured to modify a first light generated by a light source, and to thereby project a 3D multi-focal laser light pattern into the target tissue; and
a pair of mirror galvanometers configured to spatially translate a field of view of the spatial light modulator on the target tissue,
and wherein the emission path comprises a microlens array configured to modify fluorescence emitted by the target tissue such that a 2D diffraction pattern is projected onto an image detector;
ii) a controller; and
iii) a processor configured to execute instructions that cause:
the controller to:
illuminate the target tissue with spatio-temporally multiplexed 3D multi-focal light patterns, thereby causing the excitable cells to emit fluorescence, and
record a multiplexed 2D diffraction pattern of the emitted fluorescence;
resolve the recorded multiplexed 2D diffraction pattern, wherein resolving the multiplexed 2D diffraction pattern comprises deconvolving the multiplexed 2D diffraction pattern using an optical model for light propagation through an emission path from the target tissue to the image detector, wherein the optical model comprises individual 2D diffraction patterns for fluorescence emitted by the first plurality of excitable cells and diffracted by the microlens array; and
select members of the different subsets of the first plurality of excitable cells based on the individual 2D diffraction patterns.

* * * * *